(12) United States Patent
Chia

(10) Patent No.: US 10,787,483 B2
(45) Date of Patent: Sep. 29, 2020

(54) ANTIMICROBIAL PEPTIDOMIMETICS

(71) Applicant: Agency for Science, Technology and Research, Singapore (SG)

(72) Inventor: Brian Cheng San Chia, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 73 days.

(21) Appl. No.: 16/038,603

(22) Filed: Jul. 18, 2018

(65) Prior Publication Data

US 2018/0354989 A1  Dec. 13, 2018

Related U.S. Application Data

(62) Division of application No. 15/104,186, filed as application No. PCT/SG2015/050006 on Jan. 22, 2015, now Pat. No. 10,053,490.

(30) Foreign Application Priority Data

Jan. 22, 2014 (GB) .................................. 1401036.7
Oct. 16, 2014 (SG) .......................... 10201406683W

(51) Int. Cl.

| | | |
|---|---|---|
| *A61K 38/06* | (2006.01) | |
| *C07K 5/087* | (2006.01) | |
| *C07K 5/117* | (2006.01) | |
| *C07K 1/00* | (2006.01) | |
| *C07K 1/06* | (2006.01) | |
| *C07K 1/10* | (2006.01) | |
| *C07K 5/02* | (2006.01) | |
| *C07K 5/065* | (2006.01) | |
| *C07K 5/072* | (2006.01) | |
| *A61K 38/00* | (2006.01) | |

(52) U.S. Cl.
CPC .............. *C07K 5/0812* (2013.01); *C07K 1/00* (2013.01); *C07K 1/061* (2013.01); *C07K 1/10* (2013.01); *C07K 5/0212* (2013.01); *C07K 5/06078* (2013.01); *C07K 5/06095* (2013.01); *C07K 5/1024* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,776,939 | A | 7/1998 | Kroin et al. |
| 7,056,942 | B2 | 6/2006 | Hildesheim et al. |
| 10,053,490 | B2 | 8/2018 | Chia |
| 2008/0071706 | A1 | 3/2008 | Honda et al. |
| 2016/0333048 | A1 | 11/2016 | Chia |

FOREIGN PATENT DOCUMENTS

| | | |
|---|---|---|
| DE | 102009035593 A1 | 5/2010 |
| EP | 2436390 A1 | 4/2012 |
| WO | WO-2001/066147 A2 | 9/2001 |
| WO | WO-2001/074844 A2 | 10/2001 |
| WO | WO-2005/072295 A2 | 8/2005 |
| WO | WO-2006/058436 A1 | 6/2006 |
| WO | WO-2010/038040 A1 | 4/2010 |
| WO | WO-2012/045822 A1 | 4/2012 |
| WO | WO-2012/174117 A2 | 12/2012 |
| WO | WO-2013/086020 A1 | 6/2013 |

OTHER PUBLICATIONS

Murugan et al. ('De novo design and synthesis of ultra-short peptidomimetic antibiotics having dual antimicrobial and anti-inflammatory activities' PLOS ONE Nov. 2013 v8(11) pp. 1-15). (Year: 2013).*
Blast search of FRFR, 11 pages (2017). Retrieved Sep. 11, 2017 from URL: https://blast.ncbi.nlm.nih.gov/Blast.cgi.
Butler, M.S. and Cooper, M.A., Antibiotics in the clinical pipeline in 2011, Journal of Antibiotics, 37: 413-425 (2011).
CAS Registry No. 1054645-73-6, STN Entry Date Sep. 29, 2008.
CAS Registry No. 1222484-50-5, STN Entry Date May 12, 2010.
CAS Registry No. 131084-91-8, STN Entry Date Dec. 21, 1990.
CAS Registry No. 1348903-27-4, STN Entry Date Dec. 5, 2011.
CAS Registry No. 1349381-88-9, STN Entry Date Dec. 6, 2011.
CAS Registry No. 1350055-79-6, STN Entry Date Dec. 7, 2011.
CAS Registry No. 187942-95-6, STN Entry Date Apr. 3, 1997.
CAS Registry No. 869878-82-0, STN Entry Date Dec. 14, 2005.
CAS Registry No. 869878-83-1, STN Entry Date Dec. 14, 2005.
CAS Registry No. 959381-74-9, STN Entry Date Dec. 21, 2007.
Chan, A.H. et al., Discovery of *Staphylococcus aureus* Sortase a Inhibitors Using Virtual Screening and the Relaxed Complex Scheme, Chemical Biology and Drug Design, 82: 418-428 (2013).
Cooper, M.A. and Shlaes, D., Fix the antibiotics pipeline, Nature, 472: 32 (2011).
Elliott, J.T. et al., Photoactivatable peptides based on BMS-197525: a potent antagonist of the human thrombin receptor (PAR-1), Bioorganic & Medicinal Chemistry Letters, 9(2): 279-284 (1999).
Haug, B.E. et al., Bulky nonproteinogenic amino acids permit the design of very small and effective cationic antibacterial peptides, J Med Chem., 47: 4159-4162 (2004).
Huang, M.L. et al., A Comparison of Linear and Cyclic Peptoid Oligomers as Potent Antimicrobial Agents, ChemMedChem, 7:114-122 (2012).

(Continued)

*Primary Examiner* — Ronald T Niebauer
(74) *Attorney, Agent, or Firm* — Brian E. Reese; Dana M. Daukss; Choate, Hall & Stewart LLP

(57) ABSTRACT

The present invention relates to peptidomimetics of the formula (I) or (I)c wherein $L_1$, $L_2$, $L_3$, $R_1$, $R_2$, $R_3$, $R_4$, $R_5$, $R_6$, n, m, Q, X, $Z_1$ and $Z_2$ are defined as mentioned in the description and to salts and solvates of each of these compounds and to processes for the preparation thereof, compositions containing them and the uses of such compounds. It has been found that the compounds have a high microbicide activity and are suited to combat resistant bacteria, such as meticillin-resistant *Staphylococcus aureus* (MRSA) strains, at very low concentrations.

11 Claims, 24 Drawing Sheets

(56) References Cited

OTHER PUBLICATIONS

International Search Report for PCT/SG2015/050006, 8 pages (dated Aug. 28, 2015).
Murugan, R.N. et al., De Novo Design and Synthesis of Ultra-Short Peptidomimetic Antibiotics Having Dual Antimicrobial and Anti-Inflammatory Activities, PLOS One, 8(11):e80025 (2013).
Pages, J.M. et al., New Peptide-Based Antimicrobials for Tackling Drug Resistance in Bacteria: Single-Cell Fluorescence Imaging, ACS Med. Chem. Lett., 4(6):556-559 (2013).
Projan, S.K., Whither antibacterial drug discovery?, Drug Discovery Today, 13(7/8): 279-280 (2008).
Strøm, M.B. et al., The Pharmacophore of Short Cationic Antibacterial Peptides, Journal of Medicinal Chemistry, 46(9):1567-1570 (2003).
Taniguchi, K., et al., Complete Nucleotide Sequence of the Gene Encoding VP4 of a Human Rotavirus (Strain K8) which has a Unique VP4 Neutralization Epitopes, Journal of Virology, 63(9): 4101-4106 (1989).
Vippagunta, S.R. et al., Crystalline solids, Advanced Drug Delivery Reviews, 48: 3-26 (2001).
Wright, G.D., Antibiotics: A New Hope, Chemistry & Biology, 19: 3-10 (2012).
Written Opinion for PCT/SG2015/050006, 9 pages (dated Aug. 28, 2015).

* cited by examiner

Intermediate target for cpd 10 & 11

Compound No.1

Compound No.2

Compound No. 3

Compound No.4

Compound No.5

Compound No.6

Compound No.7

Compound No.8

Compound No. 9

Compound No. 10

Compound No. 11

Compound No. 12

Compound No. 13

Compound No. 14

Compound No. 15

Compound No. 16

Compound No.17

Compound No. 18

Compound No. 19

Compound No. 20

Compound No. 21

Compound No. 22

Compound No. 23

Compound No. 24

Compound No. 25

Compound No. 26

Compound No. 27

Compound No.28

Compound No. 29

ANTIMICROBIAL PEPTIDOMIMETICS

CROSS-REFERENCE TO RELATED APPLICATIONS

This patent application is a Divisional of U.S. patent application Ser. No. 15/104,186 filed on Jun. 13, 2016, which is a National Stage Entry of International Patent Application No. PCT/SG2015/050006, filed on Jan. 22, 2015, which claims priority to GB 1401036.7, filed on Jan. 22, 2014, and SG 10201406683W, filed on Oct. 16, 2014, the entire contents of each are hereby incorporated by reference herein.

TECHNICAL FIELD

The present invention relates to compounds, compositions, and methods for treating diseases and conditions. In particular, the invention relates to compounds, compositions, and methods for treating bacterial infections, disorders and conditions. The invention further relates to a compound of the formula (I)

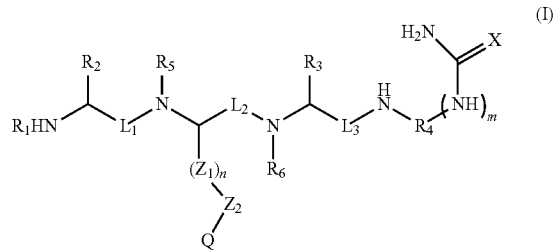

wherein
$L_1$ represents —CO—, alkandiyl, -alkyl-CO— or —CO-alkyl-;
$L_2$ represents —CO—, alkandiyl, -alkyl-CO— or —CO-alkyl-;
$L_3$ represents —CO—, alkandiyl, -alkyl-CO— or —CO-alkyl-;
$R_1$ represents hydrogen, acyl, carbamoyl, alkylaminocarbonyl, dialkylaminocarbonyl, arylcarbonyl, cycloalkylcarbonyl or heterocyclylcarbonyl;
$R_2$ represents optionally substituted alkyl, aralkyl or heteroaralkyl;
$R_3$ represents hydrogen, or represents optionally substituted alkyl, aralkyl or heteroaralkyl;
$R_4$ represents optionally substituted alkandiyl, alkendiyl, alkyndiyl, cycloalkyldiyl, alkylcycloalkyldiyl, alkylcycloalkylalkyldiyl, aryldiyl, alkylaryldiyl, alkylarylalkyldiyl;
$R_5$ represents hydrogen, or represents optionally substituted alkyl, aralkyl or heteroaralkyl;
$R_6$ represents hydrogen, or represents optionally substituted alkyl, aralkyl or heteroaralkyl;
provided that at least two of the substituents $R_2$, $R_3$, $R_5$ and $R_6$ are optionally substituted aralkyl or heteroaralkyl;
n is 0, 1, 2, 3 or 4; and
m is 0 or 1;
Q is —NH$_2$, —NH—C(NH)—NH$_2$ or —NH—C(N-alkyl)-NH-alkyl;
X is NH, O or S;
$Z_1$ is —CH$_2$—;
$Z_2$ is a direct bond, alkandiyl, cycloalkyldiyl or aryldiyl;

and to salts and solvates of each of these compounds and to processes for the preparation of, compositions containing and the uses of such compounds.
The invention also relates to their analogues of formula (Ic)

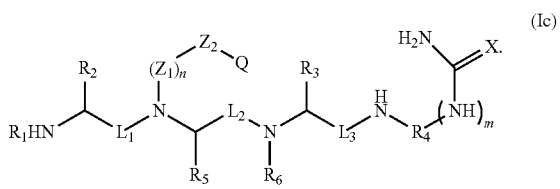

BACKGROUND

In 2011, there were 80,000 cases of invasive meticillin-resistant *Staphylococcus aureus* (MRSA) infections in the United States, resulting in 11,000 fatalities (Chan et al. Chemical Biology and Drug Design. 2013, 82, 418-428). The emergence of multi-drug-resistant bacteria and the lack of new antibiotics in the drug development pipelines of pharmaceutical companies is a major health concern (Butler et al., Journal of Antibiotics. 2011, 37, 413-425). Since 2000, only four antibiotics with new chemical scaffolds were launched; the (i) oxazolidinone Linezolid (2000), (ii) lipopeptide Daptomycin (2003), (iii) pleuromutilin Retapamulin (2007) and (iv) macrocycle Fidaxomicin (2011) (Wright, Chemistry & Biology. 2012, 19, 3-10). Hence, there is an urgent need to develop new classes of antibacterials, especially those against emerging multi-drug-resistant bacteria (Projan. Drug Discovery Today. 2008, 13, 279-280; Cooper and Shlaes. Nature. 2011, 472, 32).

SUMMARY

Novel compounds have now been found with potent bactericidal activities with an unknown mechanism of action.
Advantageously, according to the present invention there is provided a compound of formula (I):

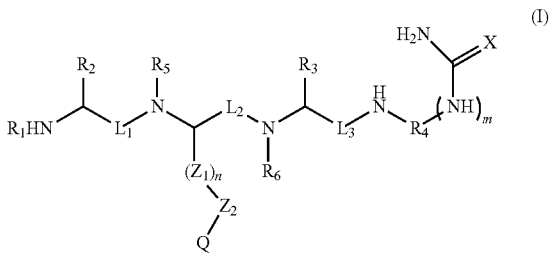

wherein
$L_1$ represents —CO—, alkandiyl, -alkyl-CO— or —CO-alkyl-;
$L_2$ represents —CO—, alkandiyl, -alkyl-CO— or —CO-alkyl-;
$L_3$ represents —CO—, alkandiyl, -alkyl-CO— or —CO-alkyl-;
$R_1$ represents hydrogen, acyl, carbamoyl, alkylaminocarbonyl, dialkylaminocarbonyl, arylcarbonyl, cycloalkylcarbonyl or heterocyclylcarbonyl;
$R_2$ represents optionally substituted alkyl, aralkyl or heteroaralkyl;

R₃ represents hydrogen, or represents optionally substituted alkyl, aralkyl or heteroaralkyl;

R₄ represents optionally substituted alkandiyl, alkendiyl, alkyndiyl, cycloalkyldiyl, alkylcycloalkyl, alkylcycloalkylalkyl, aryl, alkylaryl, alkylarylalkyl;

R₅ represents hydrogen, or represents optionally substituted alkyl, aralkyl or heteroaralkyl;

R₆ represents hydrogen, or represents optionally substituted alkyl, aralkyl or heteroaralkyl;

provided that at least two of the substituents R₂, R₃, R₅ and R₆ are aralkyl or heteroaralkyl;

n is 0, 1, 2, 3 or 4; and m is 0 or 1;

Q is —NH₂, —NH—C(NH)—NH₂ or —NH—C(N-alkyl)-NH-alkyl;

X is NH, O or S;

Z₁ is —CH₂—;

Z₂ is a direct bond, alkandiyl, cycloalkyldiyl or aryldiyl;

and to salts and solvates of each of these compounds and to processes for the preparation of, compositions containing and the uses of such compounds.

There is also provided a compound of the formula (Ic)

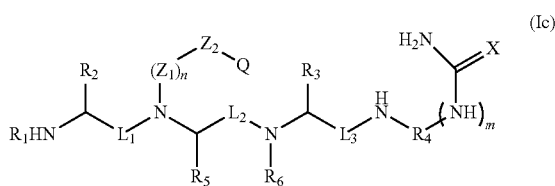

(Ic)

wherein

L₁, L₂, L₃, R₁, R₂, R₃, R₄, R₅, R₆, n, m, Q, X, Z₁ and Z₂ are defined as in formula (I), provided that at least two of the substituents R₂, R₃, R₅ and R₆ are optionally substituted aralkyl or heteroaralkyl, and to salts and solvates of each of these compounds, compositions containing the compounds and the uses of such compounds.

In the following it is mentioned how the compounds of formula (I) can be obtained.

Compounds of the formula (I')

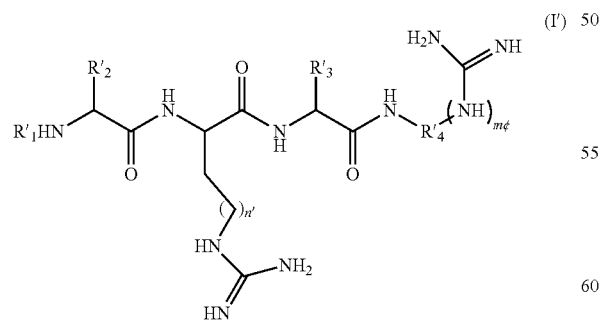

(I')

in which R'₁ to R'₄, m' and n' have the following meaning:

R'₁ represents hydrogen, acyl, carbamoyl, alkylaminocarbonyl, dialkylaminocarbonyl, arylcarbonyl, cycloalkylcarbonyl or heterocyclylcarbonyl;

R'₂ represents optionally substituted alkyl, aralkyl or heteroaralkyl;

R'₃ represents optionally substituted alkyl, aralkyl or heteroaralkyl;

R'₄ represents optionally substituted alkandiyl, alkendiyl, alkyndiyl, cycloalkyldiyl, alkylcycloalkyl, alkylcycloalkylalkyl or alkylaryl;

n' is 0, 1, 2, 3 or 4; and m' is 0 or 1;

are obtained when compounds of the formula (II')

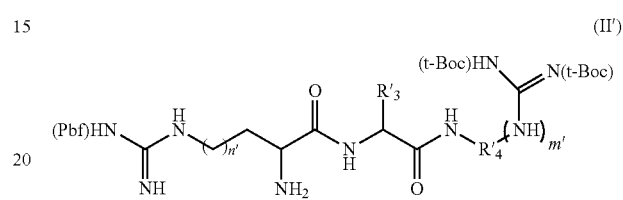

(II')

in which R'₃, R'₄, m and n have the meaning given above are reacted in the presence of an amide/peptide coupling reagent with compounds of the formula (III')

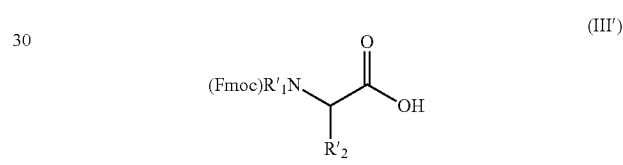

(III')

wherein R'₁ and R'₂ are defined as mentioned above, and deprotection with an acid.

Compounds of the formula (II') are obtained by reacting compounds of the formula (IV')

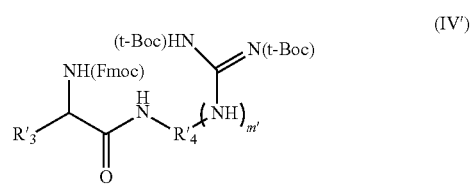

(IV')

wherein R'₃, R'₄ and m' are defined as mentioned above are reacted with a compound of the formula (V')

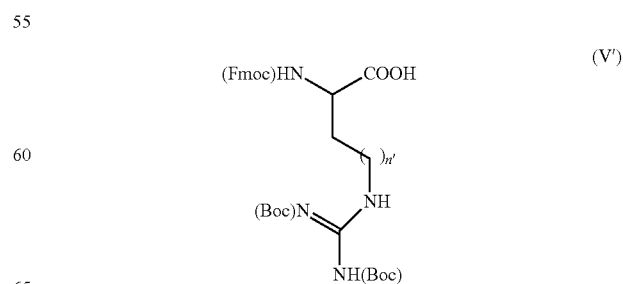

(V')

which can exist in two forms:

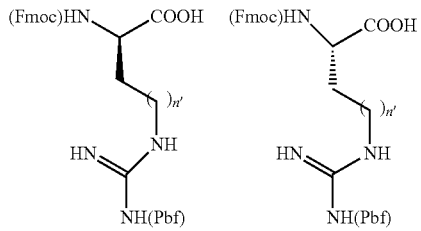

wherein n' is defined as mentioned above in the presence of a an amide/peptide coupling reagent.

Compounds of the formula (IV') are obtained when compounds of the formula (VI')

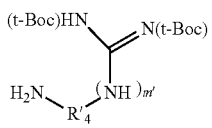

(VI')

wherein R'$_4$ and m' are defined as mentioned above, are reacted in the presence of an amide/peptide coupling reagent with compounds of the formula (VII')

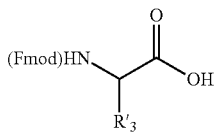

(VII')

wherein R'$_3$ is defined as mentioned above.

Compounds of the formula (VI') are obtained when a diamine of the formula (VIII')

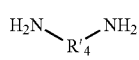

(VIII')

wherein R'$_4$ is defined as mentioned above and m' is 1 is reacted with N,N'-di-Boc-S-methylisothiourea.

R'$_1$, R'$_2$, R'$_3$, R'$_4$, n' and m' have the preferred meaning as mentioned for R$_1$, R$_2$, R$_3$, R$_4$, n and m.

Compounds of the formula (VI') wherein m' is 0 can be obtained as known from the chemical literature.

The other compounds according to formula (I) and (Ic) can be made analogously, as mentioned in the examples or according to methods known from the literature in view of the examples.

Advantageously, according to the present invention there is also provided a compound of formula (Ia) which is a selected compound of the formula (I):

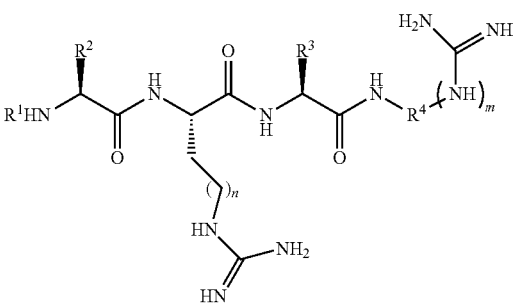

(Ia)

wherein

R$^1$ represents hydrogen, acyl, carbamoyl, alkylaminocarbonyl or dialkylaminocarbonyl;

R$^2$ represents optionally substituted alkyl, aralkyl or heteroaralkyl;

R$^3$ represents optionally substituted alkyl, aralkyl or heteroaralkyl;

R$^4$ represents optionally substituted alkandiyl, alkendiyl, alkyndiyl, cycloalkyldiyl, alkylcycloalkyl, alkylcycloalkylalkyl or alkylaryl;

n is 0, 1, 2, 3 or 4; and m is 0 or 1;

and to pharmaceutically acceptable salts and solvates of each of these compounds, compositions containing the compounds and the uses of such compounds.

It has been found that the compounds of formula (Ia) are obtained by the following process:

Compounds of the formula (Ia)

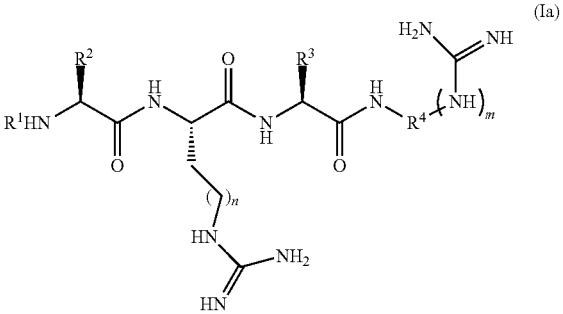

(Ia)

in which R$^1$ to R$^4$, m and n have the meaning as in formula (Ia) are obtained when compounds of the formula (IIa)

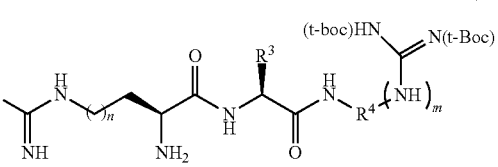

(IIa)

in which R$^3$, R$^4$, m and n have the meaning in formula (Ia) are reacted in the presence of an amide/peptide coupling reagent with compounds of the formula (IIIa)

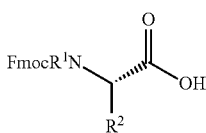
(IIIa)

wherein R¹ and R² are defined as in formula (Ia),
and deprotection with an acid.

Compounds of the formula (IIa) are obtained by reacting compounds of the formula (IVa)

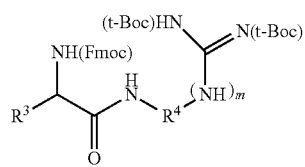
(IV)

wherein $R^3$, $R^4$ and m are defined as in formula (Ia) are reacted with a compound of the formula (Va)

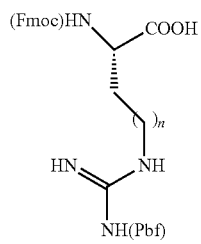
(Va)

wherein n is defined as in formula (Ia) in the presence of a an amide/peptide coupling reagent.

Compounds of the formula (IVa) are obtained when compounds of the formula (VIa)

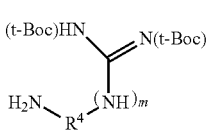
(VIa)

wherein $R^4$ and m are defined as in formula (Ia) above,
are reacted in the presence of an amide/peptide coupling reagent with compounds of the formula (VIIa)

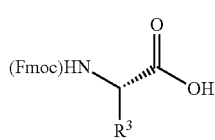
(VIIa)

wherein $R^3$ is defined as in formula (Ia).

Compounds of the formula (VIa) are obtained when a diamine of the formula (VIIIa)

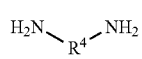
(VIIIa)

wherein $R^4$ is defined as in formula (Ia) above and m is 1 is reacted with N,N'-di-Boc-S-methylisothiourea.

According to a third aspect of the invention it has been found that the novel compounds of Formula (I) or (Ic) according to the invention are very effective as antibacterials, advantageously also showing potent bactericidal activities against MRSA. The invention provides a method of treating a disease, disorder or condition, wherein the disease, disorder or condition is a bacterial infection, such as for instance a skin infection (e.g. boils), a respiratory disease (e.g. sinusitis, pneumonia), food poisoning or any other life-threatening systemic disease, in a subject in need of such treatment, comprising administering to said subject a compound of the formula (I) or (Ic) or pharmaceutically acceptable salts and solvates thereof.

In a fourth aspect of the invention, the present invention is directed to the use of a compound of formula (I) or (Ic) or pharmaceutically acceptable salts or solvates thereof in the manufacture of a medicament for the treatment of a disease, disorder or condition selected from any bacterial infection, such as for instance a skin infection (e.g. boils), a respiratory disease (e.g. sinusitis, pneumonia), food poisoning or any other life-threatening systemic disease.

In a fifth aspect of the invention, the invention is directed to the use of a compound of formula (I) or (Ic) or pharmaceutically acceptable salts and solvates thereof for use in treating a bacterial infection.

The invention is directed in another aspect to the use of a compound of formula (I) or (Ic) or pharmaceutically acceptable salts and solvates thereof in the manufacture of a medicament for the treatment of a bacterially caused disease, disorder or condition.

Another aspect of the invention is directed to a pharmaceutical composition comprising a compound of formula (I) or (Ic) or pharmaceutically acceptable salts and solvates thereof, and a pharmaceutically acceptable excipient.

Other and further aspects will occur to those skilled in the art in light of this disclosure.

Definitions

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features. As used herein, the term "alkyl group" includes within its meaning monovalent ("alkyl") and divalent ("alkylene") straight chain or branched chain saturated aliphatic groups having from 1 to 10 carbon atoms, eg, 1, 2, 3, 4, 5, 6, 7, 8, 9, or 10 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, and the like.

The term "alkenyl group" includes within its meaning monovalent ("alkenyl") and divalent ("alkenylene") straight or branched chain unsaturated aliphatic hydrocarbon groups having from 2 to 10 carbon atoms, e.g., 2, 3, 4, 5, 6, 7, 8, 9, or 10 carbon atoms and having at least one double bond, of either E, Z, cis or trans stereochemistry where applicable, anywhere in the alkyl chain. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pententyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptentyl, 3-heptenyl, 1-octenyl, 1-nonenyl, 1-decenyl, and the like.

The term "alkynyl group" as used herein includes within its meaning monovalent ("alkynyl") and divalent ("alkynylene") straight or branched chain unsaturated aliphatic hydrocarbon groups having from 2 to 10 carbon atoms and having at least one triple bond anywhere in the carbon chain. Examples of alkynyl groups include but are not limited to ethynyl, 1-propynyl, 1-butynyl, 2-butynyl, 1-methyl-2-butynyl, 3-methyl-1-butynyl, 1-pentynyl, 1-hexynyl, methylpentynyl, 1-heptynyl, 2-heptynyl, 1-octynyl, 2-octynyl, 1-nonyl, 1-decynyl, and the like.

The term "cycloalkyl" as used herein refers to cyclic saturated aliphatic groups and includes within its meaning monovalent ("cycloalkyl"), and divalent ("cycloalkylene"), saturated, monocyclic, bicyclic, polycyclic or fused polycyclic hydrocarbon radicals having from 3 to 10 carbon atoms, e.g., 3, 4, 5, 6, 7, 8, 9, or 10 carbon atoms. Examples of cycloalkyl groups include but are not limited to cyclopropyl, 2-methylcyclopropyl, cyclobutyl, cyclopentyl, 2-methylcyclopentyl, 3-methylcyclopentyl, cyclohexyl, and the like.

The term "aryl" as used herein refers to monovalent ("aryl") and divalent ("arylene") single, polynuclear, conjugated and fused residues of aromatic hydrocarbons having from 6 to 10 carbon atoms. Examples of such groups include phenyl, biphenyl, naphthyl, phenanthrenyl, and the like.

The term "acyl" is intended to mean a —C(O)—R radical, wherein R is an optionally substituted $C_1$-$C_{20}$-alkyl, $C_2$-$C_{20}$-alkenyl, cycloalkyl having 3 to 7 carbon atoms, or aryl having or 10 carbon atoms, or a 5 to 6 ring membered heterocycloalkyl or heteroaryl group having 1 to 3 hetero atoms select from N, S, or O.

The term "heteroaromatic group" and variants such as "heteroaryl" or "heteroarylene" as used herein, includes within its meaning monovalent ("heteroaryl") and divalent ("heteroarylene"), single, polynuclear, conjugated and fused aromatic radicals having 6 to 20 atoms wherein 1 to 6 atoms are heteroatoms selected from O, N, NH and S. Examples of such groups include pyridyl, 2,2'-bipyridyl, phenanthrolinyl, quinolinyl, thiophenyl, and the like.

The term "halogen" or variants such as "halide" or "halo" as used herein refers to fluorine, chlorine, bromine and iodine.

The term "heteroatom" or variants such as "hetero-" as used herein refers to O, N, NH and S.

The term "aralkyl" as used herein, includes within its meaning ("aryl") and divalent ("arylene"), single, polynuclear, conjugated and fused aromatic hydrocarbon radicals attached to divalent, saturated, straight and branched chain $C_1$-$C_6$-alkylene radicals.

The term "heteroaralkyl" as used herein, includes within its meaning monovalent ("heteroaryl") and divalent ("heteroarylene"), single, polynuclear, conjugated and fused aromatic hydrocarbon radicals attached to divalent saturated, straight and branched chain $C_1$-$C_6$-alkylene radicals.

Preferably the aryl or arylene in the aralkyl has 6 or 10 carbon atoms. Preferably the heteroaryl or heteroarylene in the heteroaralkyl forms a five or six membered ring having 1 to 3 hetero atoms selected from N, S or O. The term "optionally substituted" as used herein means the group to which this term refers may be unsubstituted, or may be substituted with one or more groups independently selected from $C_1$-$C_6$-alkyl, $C_2$-$C_6$-alkenyl, $C_2$-$C_6$-alkynyl, thio-$C_1$-$C_6$-alkyl, $C_3$-$C_8$-cycloalkyl, $C_3$-$C_8$-cycloalkenyl, five to six membered heterocycloalkyl, halo, —COOH, —CONH$_2$, $C_1$-$C_6$-carboxyl, halo-$C_1$-$C_6$-alkyl, halo-$C_2$-$C_6$-alkynyl, hydroxyl, $C_1$-$C_6$-alkoxy, thio-$C_1$-$C_6$-alkoxy, $C_2$-$C_6$-alkenyloxy, halo-$C_1$-$C_6$-alkoxy, halo-$C_2$-$C_6$-alkenyloxy, nitro, amino, nitro-$C_1$-$C_6$-alkyl, nitro-$C_2$-$C_6$-alkenyl, nitro-$C_2$-$C_6$-alkynyl, five to six ring membered nitro-heterocyclyl, $C_1$-$C_6$-alkylamino, di-$C_1$-$C_6$-alkylamino, $C_2$-$C_6$-alkenylamine, $C_2$-$C_6$-alkynylamino, $C_1$-$C_6$-acyl, $C_2$-$C_6$-alkenoyl, $C_2$-$C_6$-alkynoyl, $C_1$-$C_6$-acylamino, di-$C_1$-$C_6$-acylamino, $C_1$-$C_6$-acyloxy, $C_1$-$C_6$-alkylsulfonyloxy, five to six ring membered heterocycloxy, five to six ring membered heterocycloamino, five to six ring membered haloheterocycloalkyl, $C_1$-$C_6$-alkylsulfenyl, $C_1$-$C_6$-alkylcarbonyloxy, $C_1$-$C_6$-alkylthio, $C_1$-$C_6$-acylthio, phosphorus-containing groups such as phosphono and phosphinyl, aryl having 6 to 10 carbon atoms, five to six ring membered heteroaryl, $C_1$-$C_4$-alkylaryl having 6 or 10 carbon atoms in the aryl, five to six ring membered $C_1$-$C_6$-alkylheteroaryl, cyano, cyanate, isocyanate, —C(O)NH($C_1$-$C_6$-alkyl), and —C(O)N($C_1$-$C_6$-alkyl)$_2$. If the term "optionally substituted" is used it refers to all substituents listed after this term, e.g. "optionally substituted methyl or ethyl" means "optionally substituted methyl" or optionally substituted ethyl".

The present invention includes within its scope all isomeric forms of the compounds disclosed herein, including all diastereomeric isomers, racemates and enantiomers, unless the stereochemistry is fixed in the formula drawing. Thus, formula (I) or (Ic) should be understood to include, for example, E, Z, cis, trans, (R), (S), (L), (D), (+), and/or (−) forms of the compounds, as appropriate in each case, unless the stereochemistry is fixed in the formula drawing.

The term "Fmoc" or "fmoc" in the formulas and description refers to a typical fluorenylmethyloxycarbonyl protecting group.

The term "t-Boc" or "Boc" in the formulas and description refers to a typical t-butoxycarbonyl protecting group.

The term "Pbf" stands for a 2,2,4,6,7-pentamethyldihydrobenzofuran-5-sulfonyl protecting group.

The term "a compound of formula (I) or (Ic) or salts or solvates thereof" or "a compound of formula (I) or a pharmaceutically acceptable salt or solvate thereof" is intended to identify a compound selected from the group consisting of: a compound of the formula (I) or (Ic), a salt of a compound of formula (I) or (Ic), a pharmaceutically acceptable solvate of a compound of formula (I) or (Ic) or a pharmaceutically acceptable solvate of a pharmaceutically acceptable salt of a compound of formula (I) or (Ic).

The term "therapeutically effective" is intended to qualify the amount of compound or pharmaceutical composition, or the combined amount of active ingredients in the case of combination therapy.

The term "treatment" as used herein to describe the present invention and unless otherwise qualified, means administration of the compound, pharmaceutical composition or combination to effect preventive, palliative, supportive, restorative or curative treatment.

The term "preventive treatment" as used herein to describe the present invention, means that the compound, pharmaceutical composition or combination is administered to a subject or member of a population that is significantly predisposed to the relevant condition.

The term "palliative treatment" as used herein to describe the present invention, means that the compound, pharmaceutical composition or combination is administered to a subject to remedy signs and/or symptoms of a condition, without necessarily modifying the progression of, or underlying etiology of, the relevant condition. Non-limiting examples include reduction of pain, discomfort, swelling or fever.

The term "supportive treatment" as used herein to describe the present invention, means that the compound, pharmaceutical composition or combination is administered to a subject as part of a regimen of therapy, but that such therapy is not limited to administration of the compound, pharmaceutical composition or combination.

The term "restorative treatment" as used herein to describe the present invention, means that the compound, pharmaceutical composition or combination is administered to a subject to modify the underlying progression or etiology of a condition.

The term "preventive treatment" as used herein to describe the present invention, means that the compound, pharmaceutical composition or combination is administered to a subject for the purpose of bringing the disease or disorder into complete remission, or that the disorder is undetectable after such treatment.

The term "MIC" as used herein, means the minimum inhibitory concentration (MIC) is the lowest concentration of an antimicrobial that will inhibit the visible growth of a microorganism after overnight incubation.

The term "compounds of the invention" or "a compound of the invention" as used herein unless otherwise specified, means a compound of formula (I) or (Ic) or a pharmaceutically acceptable salts or solvents thereof.

BRIEF DESCRIPTION OF THE DRAWING

FIG. 3a shows the mass spectra for compounds of formula (Ia) as defined by No. 2a.

FIG. 3b shows the mass spectra for compounds of formula (Ia) as defined by No. 3a.

FIG. 3c shows the mass spectra for compounds of formula (Ia) as defined by No. 4a.

FIG. 3d shows the mass spectra for compounds of formula (Ia) as defined by No. 5a.

FIG. 3e shows the mass spectra for compounds of formula (Ia) as defined by No. 6a.

FIG. 3f shows the mass spectra for compounds of formula (Ia) as defined by No. 7a.

FIG. 3g shows the mass spectra for compounds of formula (Ia) as defined by No. 8a.

FIG. 3h shows the mass spectra for compounds of formula (Ia) as defined by No. 9a.

FIG. 3i shows the mass spectra for compounds of formula (Ia) as defined by No. 10a.

FIG. 3j shows the mass spectra for compounds of formula (Ia) as defined by No. 11a.

DETAILED DESCRIPTION OF THE INVENTION

Figure 1A:
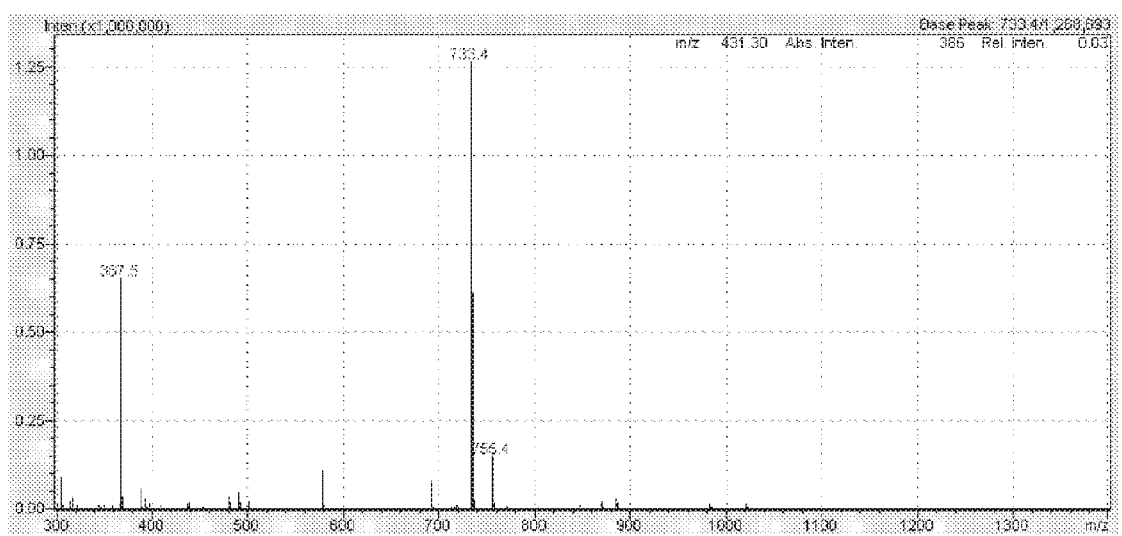
FIG. 1a shows the mass spectrum of compound 1a (Bip-Arg-Bip-agmantine).

Non-limiting examples of the above compounds according to the first aspect will now be disclosed.

The compounds of the invention may exist in a continuum of solid states ranging from fully amorphous to fully crystalline. Compounds of the invention may also exist in both unsolvated and solvated forms. The term "solvate" is used herein to describe a molecular complex comprising the compound of the invention and a stoichiometric amount of one or more pharmaceutically acceptable solvent molecules. The term "hydrate" is employed when said solvent is water. A pharmaceutically acceptable acid addition salt may be readily prepared by using a desired acid as appropriate. Typically a pharmaceutically acceptable acid addition salt can be formed by reaction of a compound of formula (I) or (Ic) with a suitable inorganic or organic acid (such as hydrobromic, hydrochloric, formic, sulfuric, nitric, phosphoric, succinic, maleic, acetic, fumaric, citric, tartaric, benzoic, p-toluensulfonic, methanesulfonic or naphthalenesulfonic acid), optionally in a suitable solvent such as an organic solvent, to give the salt which is usually isolated for example by crystallisation and filtration. Thus, a pharmaceutically acceptable acid addition salt of a compound of formula (I) can be for example a hydrobromide, hydrochloride, formate, sulfate, nitrate, phosphate, succinate, maleate, acetate, fumarate, citrate, tartrate, benzoate, p-toluenesulfonate, methanesulfonate or naphthalenesulfonate salt.

Other non-pharmaceutically acceptable salts, e.g. oxalates or trifluoroacetates, may be used, for example in the isolation of compounds of the invention, and are included within the scope of this invention. The invention includes within its scope all possible stoichiometric and non-stoichiometric forms of the salts of the compounds of formula (I) or (Ic) and is not limited to those specifically mentioned.

Compounds of the present invention can form addition salts, reaction of the amino substituent of formula (I) or (Ic) with a suitable acid. Pharmaceutically acceptable salts of the compounds of formula (I) or (Ic) include the acid salts addition of them.

It has now been found that a compound of the formula (I) or (Ic) or a pharmaceutically acceptable salt and solvate thereof is particular useful for the treatment of diseases, disorders or conditions caused by bacteria.

Examples of such diseases or disorders are mentioned above. The compounds of the invention show a particular surprising high activity against the bacteria selected from

*Staphylococcus aureus*
*Streptococcus pyogenes*, and
*Streptococcus pneumoniae.*

The activity is also high against strains that are resistant to penicillin-type antibiotics, such as methicillin, and even vancomycin. The compounds are effective in combating the bacteria at surprisingly low micro molar levels such as 25 µM or less measured as MIC values. MIC values of about 1 µM have been obtained.

The compounds are bactericidal against Gram-positive bacteria including *Staphylococcus aureus* strains ATCC 33591, ATCC 29213 RN 4220, ATCC-BAA-44, ATCC-1720, ATCC-2094, ATCC-33591, ATCC-BAA-1680, ATCC-BAA-1681 and ATCC-700699.

For administration to human patients, the total daily dose of a compound of the invention is typically in the range of 0.5 to 2 grams, but is not limited to that range depending on the mode of administration. The total daily dose may be administered in single or divided doses, and may at the physicians discretion, fall outside of the typical range.

Administration can be oral or parenteral or otherwise. In the pharmaceutical composition of the compounds of the invention excipients can be used. The term "excipient" encompasses diluents, carriers and adjuvants.

If the compounds are administered in tablets such as for example disclosed in Tablets, Vol. 1, by H. Liberman and L. Lachman (Marcel Dekker, New York, 1980).

The compounds of the invention may also be administered directly into the blood stream, into muscle or into an internal organ. Suitable means for parenteral administration include intravenous, intraarterial, intraperitoneal, intrathecal, intraventricular, intraureathral, intrasternal, intracranial, intramuscular and subcutaneous. Suitable devices for parenteral administration include needle injectors, needle free injectors and infusion techniques.

The compounds may also be administered topically to the skin or mucosa, that is, dermally or transdermal. According to the invention it has been found that the compounds of formula (I) or (Ic) are especially useful in such topical applications where they can combat methicillin resistant *Staphylococcus aureus* strains.

The compounds of the invention may also be administered directly to the eye or ear, typically in the form of drops of micronized suspension or solution in isotonic, pH-adjusted, sterile saline.

The compounds can also be inhaled to treat infection of the respiratory tract. Typical inhalers and inhalation formulations can be used. The formula (I) or (Ic) provides general definitions of the compounds according to the invention.

The formula (I) or (Ic) provides general definitions of the compounds according to the invention. Preferred substituents or ranges of the radicals given in the formula (I) or (Ic) are illustrated in the following:

$L_1$ preferably represents —CO—, $C_1$-$C_3$-alkandiyl, —$C_1$-$C_2$-alkyl-CO— or —CO—$C_1$-$C_2$-alkyl-.

$L_2$ preferably represents —CO—, $C_1$-$C_3$-alkandiyl, —$C_1$-$C_2$-alkyl-CO— or —CO—$C_1$-$C_2$-alkyl-.

$L_3$ preferably represents —CO—, $C_1$-$C_3$-alkandiyl, —$C_1$-$C_2$-alkyl-CO— or —CO—$C_1$-$C_2$-alkyl-.

$R_1$ preferably represents hydrogen, $C_1$-$C_{20}$-alkyl-CO—, $C_2$-$C_{20}$-alkenyl-CO—, $C_1$-$C_{20}$-alkyl-NH—CO—, ($C_1$-$C_{20}$-alkyl)$_2$-N—CO—, arylcarbonyl having 6 or 10 carbon atoms in the aryl moiety, $C_3$-$C_7$-cycloalkylcarbonyl or heterocyclylcarbonyl having 1 to 3 hetero atoms selected from N, O and S in the 3 to 6 membered ring.

$R_2$ preferably represents optionally substituted $C_1$-$C_{12}$-alkyl, phenyl-$C_1$-$C_4$-alkyl, biphenyl-$C_1$-$C_4$-alkyl or naphthyl-$C_1$-$C_4$-alkyl.

$R_3$ preferably represents hydrogen or preferably represents optionally substituted $C_1$-$C_{12}$-alkyl, phenyl-$C_1$-$C_4$-alkyl, biphenyl-$C_1$-$C_4$-alkyl or naphthyl-$C_1$-$C_4$-alkyl.

$R_4$ preferably represents optionally substituted $C_1$-$C_{12}$-alkandiyl, $C_2$-$C_{12}$-alkendiyl, $C_2$-$C_{12}$-alkyndiyl, $C_3$-$C_7$-cycloalkyldiyl, —$C_1$-$C_6$-alkyl-$C_3$-$C_7$-cycloalkyl-, —$C_1$-$C_6$-alkyl-$C_3$-$C_7$-cycloalkyl-$C_1$-$C_6$-alkyl-, —$C_1$-$C_6$-alkyl-phenyl- or —$C_1$-$C_6$-alkyl-naphthyl-.

$R_5$ preferably represents hydrogen or preferably represents optionally substituted $C_1$-$C_{12}$-alkyl, phenyl-$C_1$-$C_4$-alkyl, biphenyl-$C_1$-$C_4$-alkyl or naphthyl-$C_1$-$C_4$-alkyl.

$R_6$ preferably represents hydrogen or preferably represents optionally substituted $C_1$-$C_{12}$-alkyl, phenyl-$C_1$-$C_4$-alkyl, biphenyl-$C_1$-$C_4$-alkyl or naphthyl-$C_1$-$C_4$-alkyl.

n preferably is 0, 1, 2 or 3;
m preferably is 0 or 1.
Q preferably is —$NH_2$, —NH—C(NH)—$NH_2$ or —NH—C(N—$C_1$-$C_2$-alkyl)-NH—$C_1$-$C_2$-alkyl.
X preferably is NH or O;
$Z_1$ preferably is —$CH_2$—;
$Z_2$ preferably is a direct bond, $C_1$-$C_3$-alkandiyl, cyclohexyldiyl or phenyldiyl.

$L_1$ more preferably represents —CO—, —$CH_2$—, —$CH_2$—$CH_2$—, —$CH_2$—CO— or —CO—$CH_2$—.
$L_2$ more preferably represents —CO—, —$CH_2$—, —$CH_2$—$CH_2$—, —$CH_2$—CO— or —CO—$CH_2$—.
$L_3$ more preferably represents —CO—, —$CH_2$—, —$CH_2$—$CH_2$—, —$CH_2$—CO— or —CO—$CH_2$—.
$R_1$ more preferably represents hydrogen, $C_1$-$C_{16}$-alkyl-CO—, $C_2$-$C_{16}$-alkenyl-CO—, ($C_1$-$C_{16}$-alkyl-NH—CO—, ($C_1$-$C_{16}$-alkyl)$_2$-N—CO—; phenylcarbonyl or heterocyclylcarbonyl having 1 to 2 hetero atoms selected from N, O and S in the 3 to 6 membered ring.

$R_2$ more preferably represents optionally halogen or $C_1$-$C_4$-alkyl substituted $C_1$-$C_{12}$-alkyl, phenyl-$C_1$-$C_2$-alkyl, biphenyl-$C_1$-$C_2$-alkyl or naphthyl-$C_1$-$C_2$-alkyl.

$R_3$ more preferably represents hydrogen or more preferably represents optionally halogen or $C_1$-$C_4$-alkyl substituted $C_1$-$C_{12}$-alkyl, phenyl-$C_1$-$C_2$-alkyl, biphenyl-$C_1$-$C_2$-alkyl or naphthyl-$C_1$-$C_2$-alkyl.

$R_4$ more preferably represents $C_2$-$C_6$-alkandiyl, $C_2$-$C_6$-alkendiyl, $C_2$-$C_6$-alkyndiyl, $C_3$-$C_7$-cycloalkyldiyl, —$C_1$-$C_6$-alkyl-$C_3$-$C_7$-cycloalkyl-, —$C_1$-$C_6$-alkyl-$C_3$-$C_7$-cycloalkyl-$C_1$-$C_6$-alkyl-, —CH(COOH)—$C_1$-$C_6$-alkyl-, —CH(CONH$_2$)—$C_3H_6$— or —$C_1$-$C_6$-alkyl-phenyl-.

$R_5$ more preferably represents hydrogen or more preferably represents optionally halogen or $C_1$-$C_4$-alkyl substituted $C_1$-$C_{12}$-alkyl, phenyl-$C_1$-$C_2$-alkyl, biphenyl-$C_1$-$C_2$-alkyl or naphthyl-$C_1$-$C_2$-alkyl.

$R_6$ more preferably represents hydrogen or more preferably represents optionally halogen or $C_1$-$C_4$-alkyl substituted $C_1$-$C_{12}$-alkyl, phenyl-$C_1$-$C_2$-alkyl, biphenyl-$C_1$-$C_2$-alkyl or naphthyl-$C_1$-$C_2$-alkyl.

n more preferably is 0, 1, 2 or 3;

m more preferably is 0 or 1.

Q more preferably is —NH$_2$, —NH—C(NH)—NH$_2$ or —NH—C(N—CH$_3$)—NH—CH$_3$.

X more preferably is NH or O.

$Z_1$ more preferably is —CH$_2$—.

$Z_2$ more preferably is a direct bond, —CH$_2$—, cyclohexyldiyl or phenyldiyl;

$L_1$ most preferably represents —CO— or —CH$_2$—.

$L_2$ most preferably represents —CO— or —CH$_2$—.

$L_3$ most preferably represents —CO— or —CH$_2$—.

$R_1$ most preferably represents hydrogen, methylcarbonyl, ethylcarbonyl, nonylcarbonyl or heterocyclylcarbonyl having 1 to 2 hetero atoms selected from N and O in the 3 to 6 membered ring;

$R_2$ most preferably represents optionally halogen or $C_1$-$C_4$-alkyl substituted benzyl, biphenylmethyl or naphthylmethyl.

$R_3$ most preferably represents hydrogen or represents optionally halogen or $C_1$-$C_4$-alkyl substituted benzyl, biphenylmethyl or naphthylmethyl.

$R_4$ most preferably represents propandiyl, butandiyl, pentandiyl, butendiyl, butyndiyl, cyclohexyldiyl, —CH(COOH)—$C_3H_6$—, —CH(CONH$_2$)—$C_3H_6$— or —CH$_2$-phenyl-.

$R_5$ most preferably represents hydrogen or represents optionally halogen or $C_1$-$C_4$-alkyl substituted benzyl, biphenylmethyl or naphthylmethyl.

$R_6$ most preferably represents hydrogen or represents optionally halogen or $C_1$-$C_4$-alkyl substituted methyl, benzyl, biphenylmethyl or naphthylmethyl.

n most preferably is 0, 1 or 2.

m most preferably is 0 or 1.

Q most preferably is —NH$_2$, —NH—C(NH)—NH$_2$ or —NH—C(N—CH$_3$)—NH—CH$_3$.

X most preferably is NH or O.

$Z_1$ most preferably is —CH$_2$—.

$Z_2$ most preferably is a direct bond, —CH$_2$— or phenyldiyl.

The formula (Ia) provides general definitions of some selected compounds according to the invention. Preferred substituents or ranges of the radicals given in the formula (Ia) are illustrated in the following:

$R^1$ preferably represents hydrogen, $C_1$-$C_{20}$-alkyl-CO—, $C_2$-$C_{20}$-alkenyl-CO—, $C_1$-$C_{20}$-alkyl-NH—CO—, or ($C_1$-$C_{20}$-alkyl)$_2$-N—CO—.

$R^2$ preferably represents optionally substituted $C_1$-$C_{12}$-alkyl, phenyl-$C_1$-$C_4$-alkyl, biphenyl-$C_1$-$C_4$-alkyl or naphthyl-$C_1$-$C_4$-alkyl;

$R^3$ preferably represents optionally substituted $C_1$-$C_{12}$-alkyl, phenyl-$C_1$-$C_4$-alkyl, biphenyl-$C_1$-$C_4$-alkyl or naphthyl-$C_1$-$C_4$-alkyl;

$R^4$ preferably represents optionally substituted $C_1$-$C_{12}$-alkandiyl, $C_2$-$C_{12}$-alkendiyl, $C_2$-$C_{12}$-alkyndiyl, $C_3$-$C_7$-cycloalkyldiyl, $C_1$-$C_6$-alkyl-$C_3$-$C_7$-cycloalkyl, $C_1$-$C_6$-alkyl-$C_3$-$C_7$-cycloalkyl-$C_1$-$C_6$-alkyl, $C_1$-$C_6$-alkyl-phenyl or $C_1$-$C_6$-alkyl-naphthyl;

n preferably is 1, 2 or 3; and m preferably is 1.

$R^1$ more preferably represents hydrogen, $C_1$-$C_{16}$-alkyl-CO—, $C_2$-$C_{16}$-alkenyl-CO—, $C_1$-$C_{16}$-alkyl-NH—CO—, or ($C_1$-$C_{16}$-alkyl)$_2$-N—CO—.

$R^2$ more preferably represents optionally halogen substituted $C_1$-$C_{12}$-alkyl, phenyl-$C_1$-$C_2$-alkyl, biphenyl-$C_1$-$C_2$-alkyl or naphthyl-$C_1$-$C_2$-alkyl;

$R^3$ more preferably represents optionally halogen substituted $C_1$-$C_{12}$-alkyl, phenyl-$C_1$-$C_2$-alkyl, biphenyl-$C_1$-$C_2$-alkyl or naphthyl-$C_1$-$C_2$-alkyl;

$R^4$ more preferably represents $C_2$-$C_6$-alkandiyl, $C_2$-$C_6$-alkendiyl, $C_2$-$C_6$-alkyndiyl, $C_3$-$C_7$-cycloalkyldiyl, $C_1$-$C_6$-alkyl-$C_3$-$C_7$-cycloalkyl, $C_1$-$C_6$-alkyl-$C_3$-$C_7$-cycloalkyl-$C_1$-$C_6$-alkyl, —CH(COOH)—$C_1$-$C_6$-alkyl-, —CH(CONH$_2$)—$C_3H_6$— or $C_1$-$C_6$-alkyl;

n more preferably is 1, 2 or 3; and m more preferably is 1.

$R^1$ most preferably represents hydrogen or methylcarbonyl, with hydrogen being particularly being preferred;

$R^2$ most preferably represents optionally halogen substituted benzyl, biphenylmethyl or naphthylmethyl;

$R^3$ most preferably represents optionally halogen substituted benzyl, biphenylmethyl or naphthylmethyl;

$R^4$ most preferably propandiyl, butandiyl, pentandiyl, butendiyl, butyndiyl, cyclohexyl, —CH(COOH)—$C_3H_6$—, —CH(CONH$_2$)—$C_3H_6$— or —CH$_2$-Phenyl;

n most preferably is 2 or 3.

The process for making the compounds of formula (I') is described now in more detail.

In a first reaction step known and commercially available diamines of the formula (VIII') are reacted with N,N'-Di-Boc-S-methylisothiourea in the presence of a base. This reagent is commercially available from Sigma/Aldrich. Bases can be customary acid acceptors such as tertiary amines, preferably N,N-disopropylethylamine. Suitable solvents include inert organic solvents such as hydrocarbons, preferably methylene dichloride (dichloromethane).

The reaction temperatures in this process step can be varied in a relatively wide range. In general the process is carried out at temperatures of 0 to 100° C., preferably 15 to 60° C., most preferably at room temperature.

When carrying out this process step the starting materials of formula (VIII') and the reagent are generally each employed in approximately equal amount. It may be beneficial to use the diamine of formula (VIII') in excess to the reagent.

Work up is done by customary separation methods, preferably flash chromatography and evaporation of the solvents.

In a second reaction step the obtained compounds of the formula (VI') are reacted with a compound of the formula (VII'). Compounds of the formula (VII') are known or can be prepared according to known methods. For instance one of such compounds is commercially available from Merck Millipore and GL Biochem China as "Fmoc-4-phenyl-Phe-OH", "Fmoc-4-phenyl-L-Phe-OH" or "Fmoc-Bip-OH".

The amide/peptide coupling reagent can be customary coupling reagents such as 2-(1H-Benzotriazole-1-yl)-1,1,3,3-tetramethyluronium hexafluorophosphate (HBTU). Other suitable coupling reagents include N,N'-Dicyclohexylcarbodiimide (DCC), (N,N'-Diisopropylcarbodiimide (DIC), (1-[Bis(dimethylamino)methylene]-1H-1,2,3-triazolo[4,5-b]pyridinium 3-oxid hexafluorophosphate (HATU), 2-(6-

Chloro-1H-benzotriazole-1-yl)-1,1,3,3-tetramethylaminium hexafluorophosphate (HCTU), benzotriazol-1-yl-oxytripyrrolidinophosphonium hexafluorophosphate (PyBop), 6-Chloro-benzotriazole-1-yloxy-tris-pyrrolidinophosphonium hexafluorophosphate (Pyclock) or Ethyl 2-Cyano-2-(hydroxyimino)acetate (Oxyma). Preferably these coupling reagents are used in the presence of a base such as for instance a tertiary amine, preferably N, N-Diisopropylamine.

The reaction temperatures in this process step can be varied in a relatively wide range. In general the process is carried out at temperatures of 0 to 100° C., preferably 15 to 60° C., most preferably at room temperature.

When carrying out this process step the starting materials of formula (VI') and the compound of formula (VII') are generally each employed in approximately equal amount. It may be beneficial to use the compound of formula (VII') in small excess.

Work up is done by customary separation methods, preferably by washing steps and an evaporation of the solvent. Dissolution and further post-reaction with a base, such as 1,8-Diazabicyclo[5.4.0]undec-7-ene (DBU), at room temperature and flash chromatography is possible.

In a third reaction step the obtained compounds of the formula (IV') are reacted with a compound of the formula (V'). Compounds of the formula (V') are known or can be prepared according to known methods. For instance one of such compounds is commercially available from Merck Millipore or GL Biochem as "Fmoc-Arg(Pbf)-OH" or Fmoc-Arg(Boc)$_2$-OH.

The amide/peptide coupling reagent can be customary coupling reagents such as 2-(1H-Benzotriazole-1-yl)-1,1,3,3-tetramethyluronium hexafluorophosphate (HBTU). Other suitable coupling reagents include N,N'-Dicyclohexylcarbodiimide (DCC), (N,N'-Diisopropylcarbodiimide (DIC), (1-[Bis(dimethylamino)methylene]-1H-1,2,3-triazolo[4,5-b]pyridinium 3-oxid hexafluorophosphate (HATU), 2-(6-Chloro-1H-benzotriazole-1-yl)-1,1,3,3-tetramethylaminium hexafluorophosphate (HCTU), benzotriazol-1-yl-oxytripyrrolidinophosphonium hexafluorophosphate (PyBop), 6-Chloro-benzotriazole-1-yloxy-tris-pyrrolidinophosphonium hexafluorophosphate (Pyclock) or Ethyl 2-Cyano-2-(hydroxyimino)acetate (Oxyma). Preferably these coupling reagents are used in the presence of a base such as for instance a tertiary amine, preferably N, N-Diisopropylamine.

Suitable solvents include inert organic solvents such as dimethylformamide.

The reaction temperatures in this process step can be varied in a relatively wide range. In general the process is carried out at temperatures of 0 to 100° C., preferably 15 to 60° C., most preferably at room temperature.

When carrying out this process step the starting materials of formula (IV') and the compound of formula (V') are generally each employed in approximately equal amount. It may be beneficial to use the compound of formula (V') in excess.

Work up is done by customary separation methods, preferably by washing steps and an evaporation of the solvent. Dissolution and further post reaction with a base, such as 1,8-Diazabicyclo[5.4.0]undec-7-ene (DBU) or piperidine, at room temperature and flash chromatography is possible.

In a fourth reaction step the obtained compounds of the formula (II') are reacted with a compound of the formula (III'). Compounds of the formula (III') are known or can be prepared according to known methods. For instance one of such compounds is commercially available from Merck Millipore or GL Biochem as "Fmoc-4-phenyl-Phe-OH" or "Fmoc-Bip-OH". It can also be bought from Creosalus Advanced ChemTech.

The amide/peptide coupling reagent can be customary coupling reagents such as 2-(1H-Benzotriazole-1-yl)-1,1,3,3-tetramethyluronium hexafluorophosphate (HBTU). Other suitable coupling reagents include N,N'-Dicyclohexylcarbodiimide (DCC), (N,N'-Diisopropylcarbodiimide (DIC), (1-[Bis(dimethylamino)methylene]-1H-1,2,3-triazolo[4,5-b]pyridinium 3-oxid hexafluorophosphate (HATU), 2-(6-Chloro-1H-benzotriazole-1-yl)-1,1,3,3-tetramethylaminium hexafluorophosphate (HCTU), benzotriazol-1-yl-oxytripyrrolidinophosphonium hexafluorophosphate (PyBop), 6-Chloro-benzotriazole-1-yloxy-tris-pyrrolidinophosphonium hexafluorophosphate (Pyclock) or Ethyl 2-Cyano-2-(hydroxyimino)acetate (Oxyma). Preferably these coupling reagents are used in the presence of a base such as for instance a tertiary amine, preferably N, N-Diisopropylamine.

Suitable solvents include inert organic solvents such as dimethylformamide.

The reaction temperatures in this process step can be varied in a relatively wide range. In general the process is carried out at temperatures of 0 to 100° C., preferably 15 to 60° C., most preferably at room temperature.

When carrying out this process step the starting materials of formula (IV') and the compound of formula (V') are generally each employed in approximately equal amount. It may be beneficial to use the compound of formula (V') in excess.

Work up is done by customary separation methods, preferably by washing steps and an evaporation of the solvent. Dissolution and further post-reaction with a base, such as diazabicycloundecene (DBU) or piperidine, at room temperature and flash chromatography is possible.

The compounds of the formula (I') can be obtained from their precursors by reaction with a strong organic acid such as trifluoroacetic acid. Such organic acids must be able to remove the Pbf and Boc moieties.

The reaction temperatures in this process step can be varied in a relatively wide range. In general the process is carried out at temperatures of 0 to 100° C., preferably 15 to 60° C., most preferably at room temperature.

Work up is done by customary separation methods, preferably by evaporation of the solvent, re-dissolution, chromatography and HPLC.

Other compounds disclosed herein also can be synthesized analogous to the compounds of Formula (I') or can be synthesized utilizing known methodologies disclosed in texts well known to those skilled in the art such as Amino acids, Peptides and Proteins in Organic Chemistry, Ed. A. B. Hughes, vol. 4; Wiley-VCH, Germany, 2011.

EXAMPLES

Materials and Methods

In the examples described below, unless otherwise indicated, all temperatures in the following description are in degrees Celsius and all parts and percentages are by weight, unless indicated otherwise. Reagents useful for synthesizing compounds may be purchased from commercial suppliers, such as Sigma-Aldrich Pte Ltd (Singapore 117528, Singapore), Merck Millipore, GL Biochem China or Creosalus Advanced Chemtech and others, and used without further purification, unless otherwise indicated, or obtained or prepared according to techniques known in the art.

HPLC was conducted on a Shimadzu Prominence system. Mass spectrometry was conducted using a Shimadsu LC-MS system.

All the NMR experiments for $^1H$ (400.13 MHz) and $^{13}C$ (100.61 MHz) nuclei were performed on a Bruker Ultrashield 400+ NMR spectrometer. NMR spectra are reported in ppm with reference to an internal tetramethylsilane standard (0.00 ppm for $^1H$ and $^{13}C$) or solvent peak(s) of $CD_3OD$ (3.31 and 49.0 ppm). When peak multiplicities are reported, the following abbreviations are used: s=singlet, d=doublet, t=triplet, q=quartet, m=multiplet, br=broadened, dd=doublet of doublets, dt=doublet of triplets, bs=broadened singlet. Coupling constants, when given, are reported in hertz.

Example 1: Preparation of Compound 1a (Bip-Arg-Bip-agmantine)

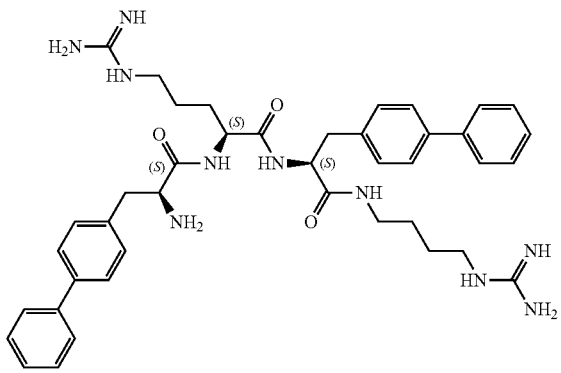

Chemical Formula: $C_{41}H_{52}N_{10}O_3$
Exact Mass: 732.4224
Molecular Weight: 732.9168

Step 1:

1,4-Diaminobutane (0.5 mmol, 44 mg), N,N-di-(t-butoxycarbonyl)-S-methylisothiourea (0.4 mmol, 116 mg) and N,N-diisopropylethylamine (DIPEA; 1 mmol, 175 µL) were dissolved in anhydrous $CH_2Cl_2$ (6 mL). The mixture was stirred at 25° C., 16 h under $N_2$ atmosphere and the resulting guanylated amine was purified by flash chromatography using a $CH_2Cl_2$/methanol gradient and monitored using MS. The solvent was removed in vacuo to give a colourless oil (79 mg, 0.24 mmol, 60%).

Step 2:

Fmoc-Bip-OH (0.264 mmol), HBTU (0.48 mmol), DIPEA (0.72 mmol) and dimethylformamide (DMF, 10 mL) were added to the oil and the mixture was stirred at 25° C. for 1 h.

Step 3:

The contents were dissolved in ethyl acetate (30 mL) and washed with brine (50 mL) thrice. The organic phase was removed in vacuum to give a yellow gel which was dissolved in $CH_2Cl_2$ (10 mL).

Step 4:

DBU (0.36 mmol, 54 µL) was added to the mixture and stirred at 25° C. for 1 h. The intermediate was purified by flash chromatography using a $CH_2Cl_2$/methanol gradient monitored using MS. The solvent was removed in vacuo to give a colourless oil (0.20 mmol, 83%).

Step 5:

Fmoc-Arg(Pbf)-OH (0.264 mmol), HBTU (0.48 mmol), DIPEA (0.72 mmol) and dimethylformamide (DMF, 10 mL) were added to the oil and the mixture was stirred at 25° C. for 1 h.

Step 6:

Steps 3 and 4 were repeated for Fmoc removal.

Step 7:

Step 2 was repeated.

Step 8:

Steps 3 and 4 were repeated for Fmoc removal.

Step 9:

$TFA:CH_2Cl_2$ (1.5 mL, 95:5 v/v) was added to Bip-Arg(Pbf)-Bip-agmatine$(Boc)_2$ and stirred for 1 h at room temperature.

Step 10:

Excess $TFA:CH_2Cl_2$ was blown off using a gentle $N_2(g)$ stream to yield a yellow oil. The oil was re-dissolved in MeOH and purified by HPLC (water and acetonitrile solvent), retention time ~16.5 min, to give the target product (Bip-Arg-Bip-agmatine; BRB-Ag; ETC-2016975) as a white powder (4.1 mg, 0.006 mmol, 6% overall yield).

The electrospray ionization-mass spectrum (ESI-MS) shows three characteristic peaks at 367.5 $[M+2H]^{2+}$, 733.4 $[M+H]^+$ and 755.4 $[M+Na]^+$.

The mass spectrum is shown in FIG. 1a.

NMR Spectral data: $^1H$ NMR (400 MHz, $CD_3OD$) δ 1.20-1.77 (8H, m), 2.75-3.24 (10H, m), 4.07, 4.33, 4.49 (1H, m, α-Hs), 7.10-7.52 (18H, m, aromatics); $^{13}C$ NMR (100 MHz, $CD_3OD$) δ 24.6, 25.6, 26.0, 28.9, 36.9, 37.5, 38.3, 40.5, 40.7 (methylene Cs), 52.9, 54.0, 54.8 (α-Cs), 126.3 (×2), 126.5 (×2), 126.6 (×2), 126.9, 127.1, 127.2 (×2), 128.4 (×2), 128.5 (×2), 129.5 (×2), 129.7 (×2), 132.9, 135.8, 139.6, 140.3, 140.4, 140.6 (aromatics), 157.2, 157.3 (guanidinium), 168.3, 171.4, 171.9 (C=O).

Figure 1B:
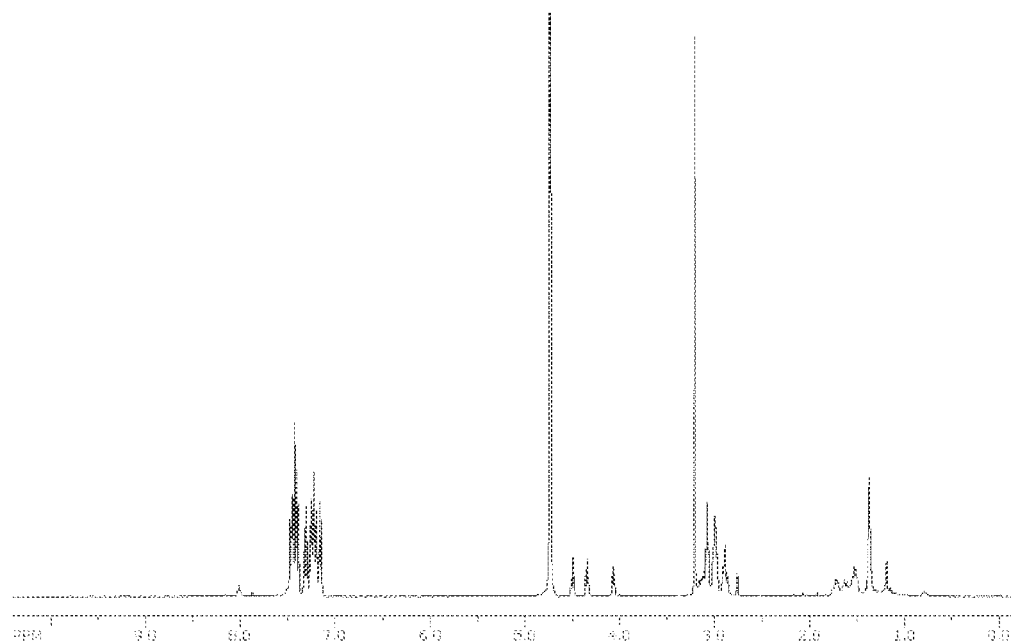
FIG. 1b shows the $^1$H NMR spectra mass spectrum of compound 1a (Bip-Arg-Bip-agmantine).
Figure 1C:
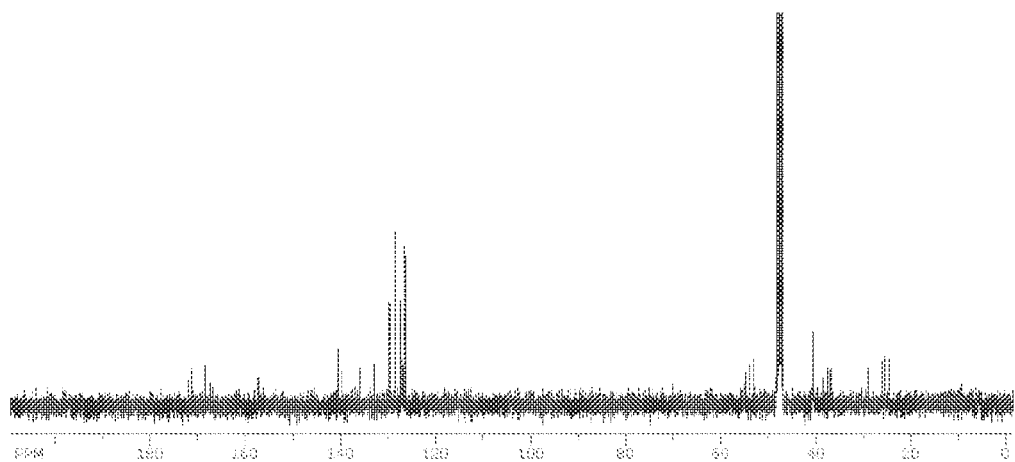
FIG. 1c shows the $^{13}$C NMR spectra mass spectrum of compound 1a (Bip-Arg-Bip-agmantine).

The $^1H$ and $^{13}C$ NMR spectra are shown in FIGS. 1b and 1c respectively.

Example 1b: Proposed Scheme for Solid-Phase Synthesis (24 Step)

1. Anchor Fmoc-Bip-OH (5.0 mmol, 5 eq.) to 2-chlorotrityl chloride resin (1.0 mmol scale) with DIPEA (5.0 mmol, 5 eq.) in $CH_2Cl_2$ (10 mL) for 60 minutes.
2. Filter off excess solvent/reagents and wash resin with $CH_2Cl_2$ (~10 mL×2), $CH_3OH$ (~10 mL×2) followed by DMF (~10 mL×2).
3. Remove Fmoc using piperidine:DMF (20% v/v) with stirring and microwave (40 W, 65° C., 5 min).
4. Filter off excess solvent/reagents and wash resin with DMF (~10 mL×2), $CH_3OH$ (~10 mL×2) followed by DMF (~10 mL×2).
5. Dissolve Fmoc-Arg(Pbf)-OH (5.0 mmol, 5 eq.), HBTU (5.0 mmol, 5 eq.), DIPEA (5.0 mmol, 5 eq.) in DMF (10 mL) and allow this mixture to react with the resin and microwave (40 W, 65° C., 10 min).
6. Filter off excess solvent/reagents and wash resin with DMF (~10 mL×2), $CH_3OH$ (~10 mL×2) followed by DMF (~10 mL×2).
7. Repeat step 3.
8. Repeat step 4.
9. Dissolve Fmoc-Bip-OH (5.0 mmol, 5 eq.), HBTU (5.0 mmol, 5 eq.), DIPEA (5.0 mmol, 5 eq.) in DMF (10 mL) and allow this mixture to react with the resin and microwave (40 W, 65° C., 10 min).
10. Repeat step 4.
11. Repeat step 3.
12. Repeat step 4.

13. Dissolve Boc$_2$O (Boc-anhydride; 5.0 mmol, 5 eq.) and DIPEA (5.0 mmol, 5 eq.) in DMF (10 mL) and allow this mixture to react with the resin and microwave (40 W, 65° C., 10 min).

14. Filter off excess solvent/reagents and wash resin with DMF (~10 mL×2), CH$_3$OH (~10 mL×2) followed by CH$_2$Cl$_2$ (~10 mL×2).

15. Add 10% acetic acid in CH$_2$Cl$_2$ (v/v) to the resin and stir (room temperature, 60 minutes)

16. Filter the mixture and neutralise the solution with NaHCO$_3$ until no effervescence is seen.

17. Add CH$_2$Cl$_2$ and brine. The organic layer was concentrated in vacuo to yield crude Bip-Arg(Pbf)-Bip-OH as a yellow oil.

18. React 1,4-diaminobutane (2 mmol, 2 eq) with 1,3-bis(tert-butoxycarbonyl)-2-methyl-2-thiopseudourea (obtainable from Sigma, 1 mmol) and DIPEA (6 mmol, 6 eq.) in CH$_2$Cl$_2$ for 60 minutes.

19. Purify the mixture with flash chromatography using hexane, EtOAc, CH$_2$Cl$_2$ and CH$_3$OH to obtain NH$_2$—(CH$_2$)$_4$-guanidine(Boc)$_2$ as a white solid.

20. Mix crude Bip-Arg(Pbf)-Bip-OH with NH$_2$—(CH$_2$)$_4$-guanidine(Boc)$_2$, EDC (1.2 mmol) and HOBt (1.2 mmol) in DMF (5 mL) and allow this mixture to react overnight at room temperature.

21. The reaction mixture was extracted using ethyl acetate/brine and the organic layer was concentrated in vacuo to yield a yellow oil.

22. Remove the Boc and Pbf with TFA and two drops of water using microwave (40 W, 65° C., 10 min).

23. Excess TFA was blown off with a N$_2$ gas stream (~20 min for 1 mL) to yield the crude target as yellow oil.

24. Purify the yellow oil with C$_{18}$ Reverse Phase HPLC.

kept at 5%. 100 µL of the antibacterial solution are dispensed into the first well of a row. 50 µL of medium containing 0.5% of DMSO are dispensed to the rest of the wells. A 2-fold serial dilution is achieved by transferring 50 µL from the first well (containing the highest concentration of antibacterial) into the second well, and continuing like this until the 10th well in the row. The final 50 µL are discarded so that every well has 50 µL of each antibacterial dilution.

The 11th well was used as the growth control well (medium with bacterial inoculums, no antibacterial) while the 12th well was the sterility control well (medium only). Table 1 illustrates a typical sample layout.

The bacterial suspension prepared above is mixed thoroughly, and diluted by a factor of 1:100 in the sterile medium. Each well and the growth control well is inoculated with 50 µL of the bacterial suspension. This resulted in the final desired inoculums of 5×10$^5$ cfu/mL in each well. To the sterility control well 50 µL of sterile medium are added in place of the bacterial suspension. 10 µL aliquot from the growth control well is removed immediately after inoculating the plate and pipetted it into a sterile Eppendorf tube holding 990 µL of sterile broth. It is mixed well by vortexing. This suspension is further diluted (1:10) by pipetting 100 µL into 900 µL of sterile broth and mixing it well. 100 µL of each of the two dilutions are plated onto two different antibacterial-free agar plates. A sterile cell spreader is used to spread the liquid. Then the plate is sealed with a transparent adhesive film.

The microtiter plate and agar plates are incubated at 37° C. for 16-20 hours or until satisfactory growth is obtained. The colonies on the agar plate are counted the next day to verify that the right number of cfu was inoculated. The plate is agitated in the SpectraMax spectrophotometer for 90 s and the OD$_{600}$ for all the wells in the plate is recorded.

TABLE 1

Typical plate layout for the setup of a 96-well plate for the cell-based assay.

| | Conc.(µg/mL) | 1 | 2 | 3 | 4 | 5 | 6 | 7 | 8 | 9 | 10 | 11 | 12 |
|---|---|---|---|---|---|---|---|---|---|---|---|---|---|
| A | Linezolid | 125.00 | 62.50 | 31.25 | 15.63 | 7.81 | 3.91 | 1.95 | 0.98 | 0.49 | 0.24 | GC | SC |
| B | Linezolid | 125.00 | 62.50 | 31.25 | 15.63 | 7.81 | 3.91 | 1.95 | 0.98 | 0.49 | 0.24 | GC | SC |
| C | | | | | | | | | | | | GC | SC |
| D | | | | | | | | | | | | GC | SC |
| E | | | | | | | | | | | | GC | SC |
| F | | | | | | | | | | | | | |
| G | | | | | | | | | | | | | |
| H | | | | | | | | | | | | GC | SC |

GC: Growth control
SC: Sterility control

Example 2: Biological Activity Measurement

The compounds of the working examples have been tested for biological activity in the following assay:

Using a sterile loop, 3 to 5 isolated colonies of bacteria of the same morphological appearance are selected from the overnight agar plate. The colonies are transferred into a conical flask containing 5 mL of liquid medium (i.e. Mueller-Hinton broth). The broth is incubated at 37° C. in a shaker at 220 rpm until it reaches a turbidity that is equal to the turbidity of a McFarland Standard 0.5 (correspond to 1×10$^8$ cfu/mL). This culture growth step will require 1-2 hours depending on the bacteria tested.

During this pause period, an antibacterial dilution is prepared. Therefore an antibacterial stock solution is diluted in Mueller-Hinton broth. The concentration of DMSO is The compound of example 1 (compound 1a) showed an MIC value of 3.125 µM vs. MRSA (ATCC 33591), S. aureus (RN 4220) and S. aureus (ATCC 29123) and 6.25 µM vs. Strep. pneumoniae (ATCC 49619) and Strep. pyogenes (ARC 838). In the S. aureus tests the compound had a lower MIC value than commercially available antibacterial compounds Linezolid and Daptomycin. In the Strep. tests it showed at least improvement over Daptomycin.

The compound also showed activity on E. faecalis.

Figure 2:
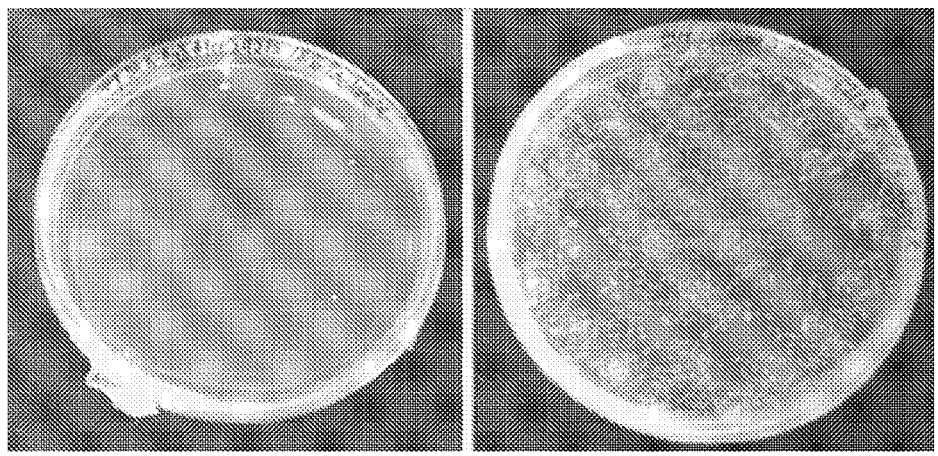
FIG. 2 shows the bactericidal activity vs. *S. aureus* at MIC after dilution of the antibacterial. The left panel shows an image following treatment with compound 1a (Bip-Arg-Bip-agmantine) at its MIC. The right panel shows an image following treatment with Linezolid at its MIC.
Figure 3A:
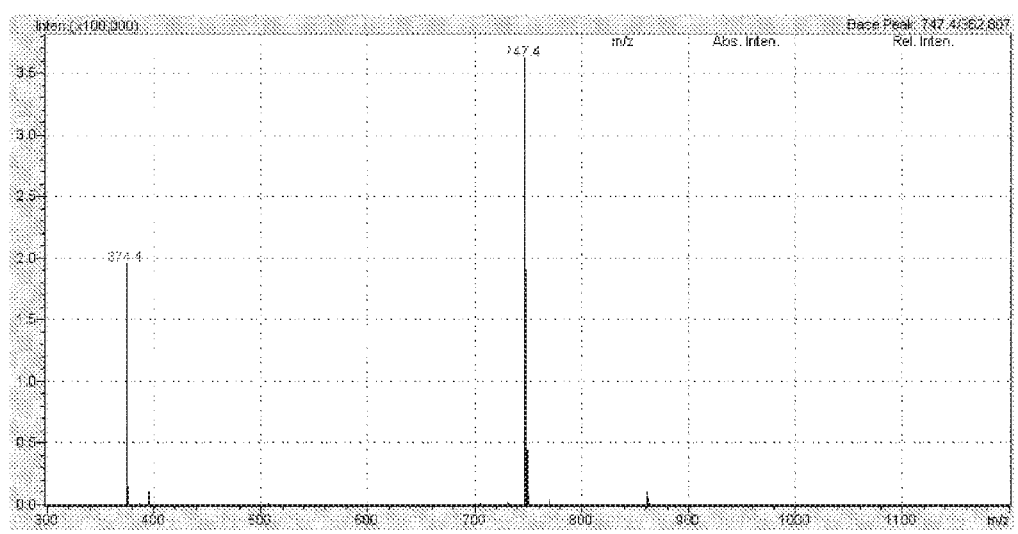
Figure 3B:
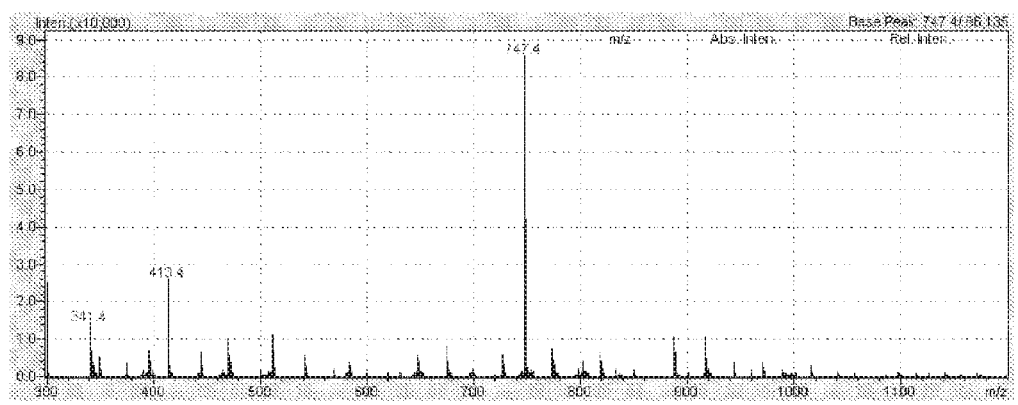
Figure 3C:
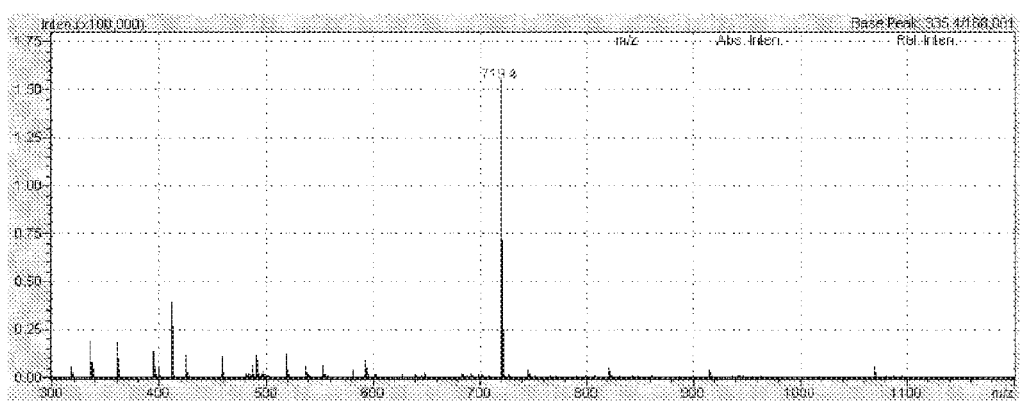
Figure 3D:
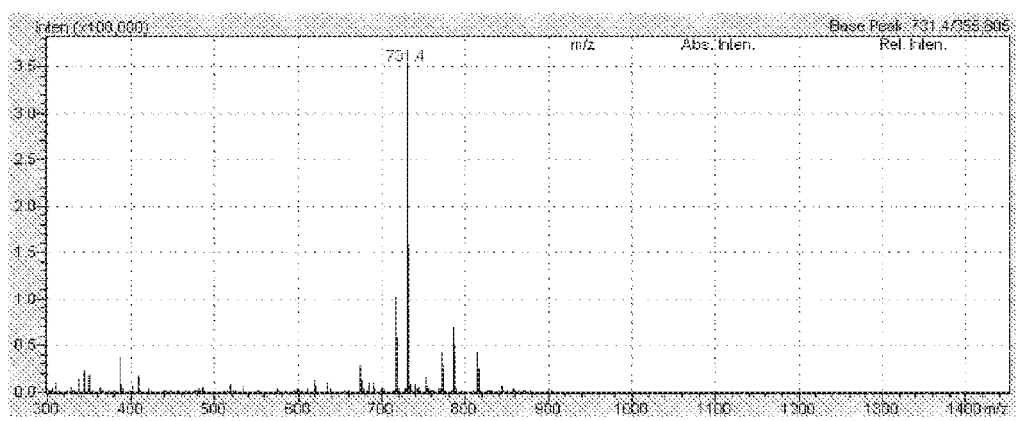
Figure 3E:
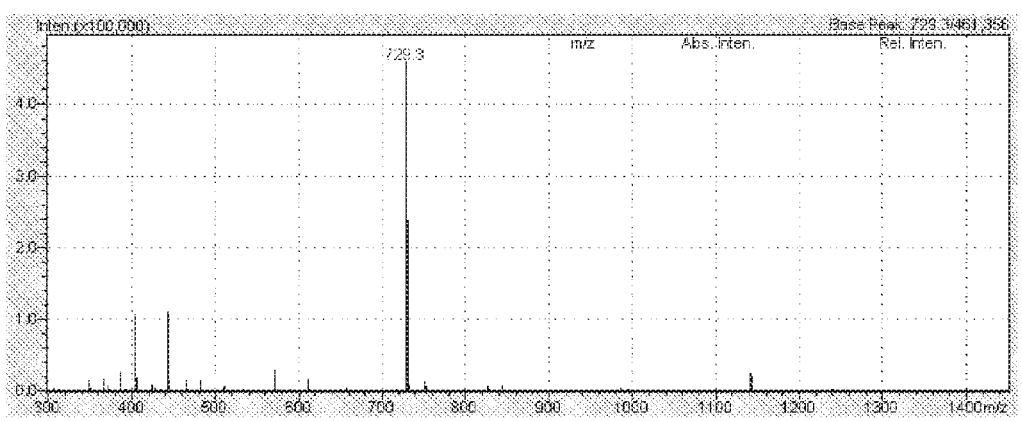
Figure 3F:
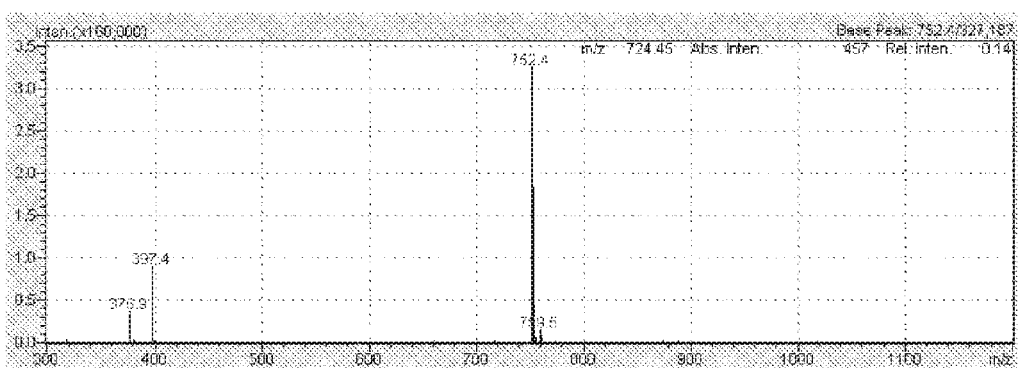
Figure 3G:
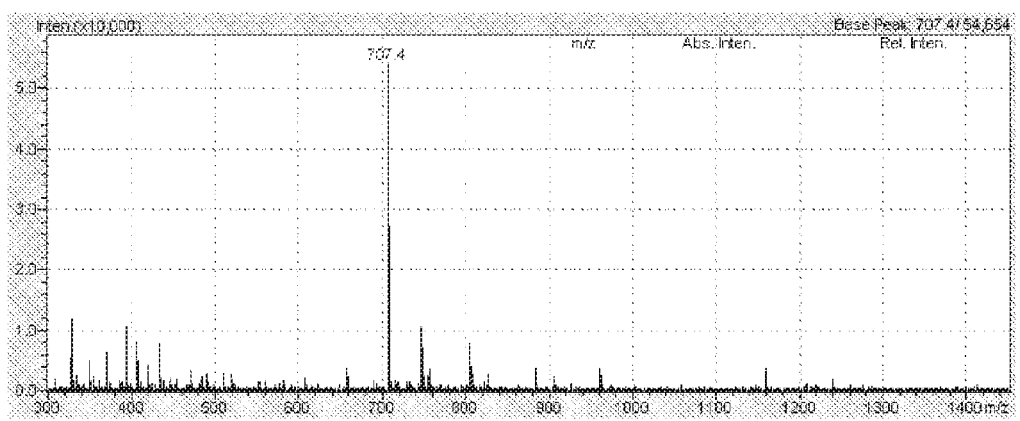
Figure 3H:
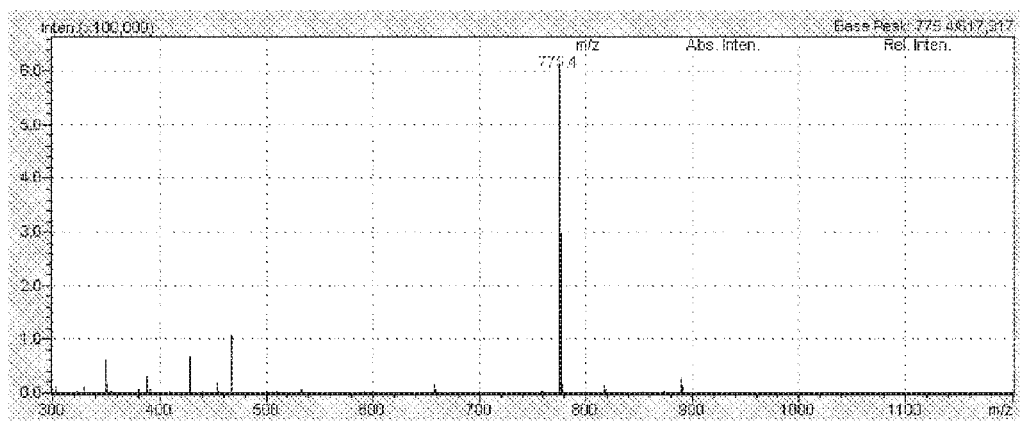
Figure 3I:
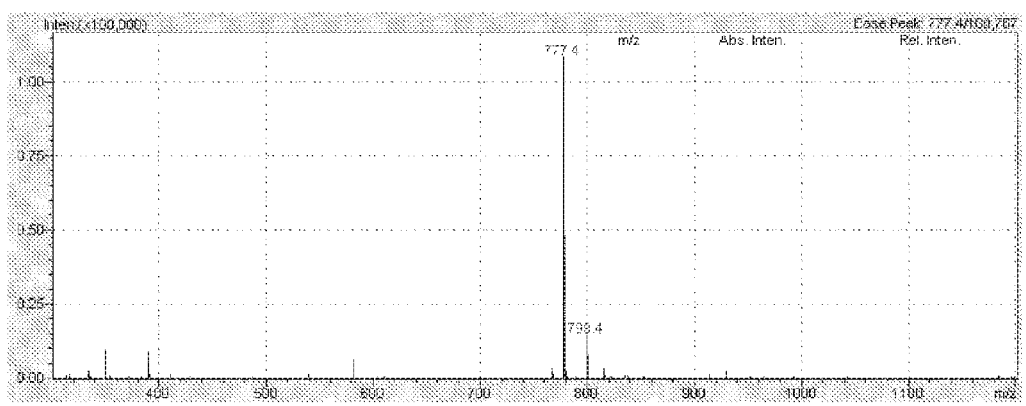
Figure 3J:
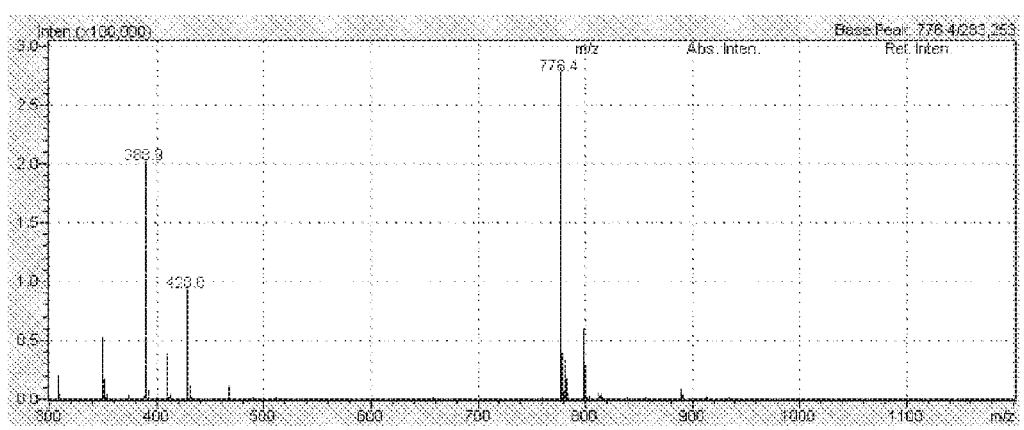

FIG. 2 shows the bactericidal activity vs. S. aureus (ATCC 29213) at its respective MIC (compound of Example 1a on the left, Linezolid on the right) after dilution of the antibacterial. The picture on the left shows that upon treatment with the compound of Example 1 at its MIC, the bacteria remains dead even after the antibacterial was diluted, suggesting that it possessed a bactericidal mode of action. The picture on the right shows that upon treatment with Linezolid at its MIC, after the drug was diluted, the bacteria was able to re-grow, suggesting that Linezolid is bacteriostatic.

Example 3: Synthesized Compounds of Formula (Ia)

According to the processes of the invention or known methods the following other compounds of the formula (Ia) have been synthesized and their MIC value vs. MRSA (ATCC 33591) and *S. aureus* (ATCC 29213) determined:

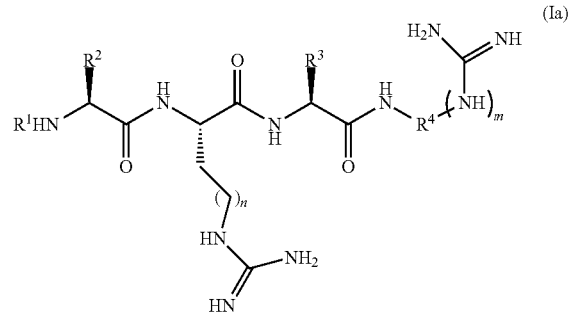

Bip stands for

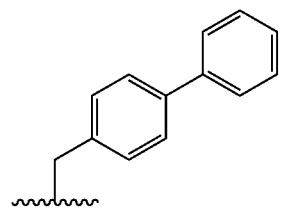 [SMILES: *Cc1ccc(-c2ccccc2)cc1]

Naph stands for

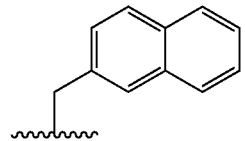 [SMILES: *Cc1ccc2ccccc2c1]

FIGS. 3*a* to 3*j* show the mass spectra for the compounds 2a to 11a.

Example 4: Preparation of Compound (A)

The compound of the formula (A) has been prepared according to the following process.

| No. | R¹ | R² | R³ | R⁴ | m | n | MIC(μM) (ATCC 33591) | MIC(μM) (ATCC 29213) |
|---|---|---|---|---|---|---|---|---|
| 1a | H | Bip | Bip | —C₄H₈— | 1 | 2 | 3.125 | 3.125 |
| 2a | H | Bip | Bip | —C₄H₈— | 1 | 3 | 6.25 | not determined |
| 3a | H | Bip | Bip | —C₅H₁₀— | 1 | 2 | 6.25 | 12.5 |
| 4a | H | Bip | Bip | —C₃H₆— | 1 | 2 | 50 | 50 |
| 5a | H | Bip | Bip | —CH₂—CH=CH—CH₂— (trans) | 1 | 2 | 100 | 12.5 |
| 6a | H | Bip | Bip | —CH₂—C≡C—CH₂— | 1 | 2 | 6.25 | 6.25 |
| 7a | H | Bip | Bip | —CH₂—C₆H₄— | 0 | 2 | 6.25 | 6.25 |
| 8a | H | Naph | Bip | —C₄H₈— | 1 | 2 | 12.5 | 12.5 |
| 9a | CH₃—CO— | Bip | Bip | —C₄H₈— | 1 | 2 | 12.5 | 6.25 |
| 10a | H | Bip | Bip | 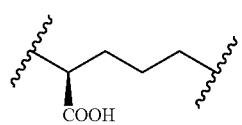 | 1 | 2 | 25 | 25 |
| 11a | H | Bip | Bip |  | 1 | 2 | 12.5 | 12.5 |

(A)

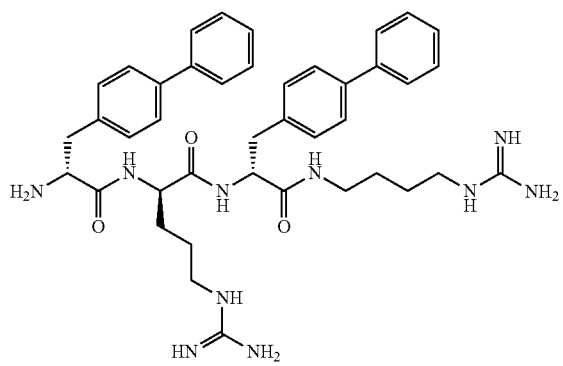

In a first reaction step known and commercially available 1,4-diaminobutane was reacted with N,N'-Di-Boc-S-methylisothiourea in the presence of a base. This reagent is commercially available from Sigma/Aldrich. Bases can be customary acid acceptors such as tertiary amines, preferably N,N-disopropylethylamine. Suitable solvents include inert organic solvents such as hydrocarbons, preferably methylene dichloride (dichloromethane).

The reaction temperatures in this process step can be varied in a relatively wide range. In general the process is carried out at temperatures of 0 to 100° C., preferably 15 to 60° C., most preferably at room temperature.

When carrying out this process step the starting materials and the reagents are generally each employed in approximately equal amount. It may be beneficial to use the diamine in excess to the reagent.

Work up is done by customary separation methods, preferably flash chromatography and evaporation of the solvents.

In a second reaction step the obtained compounds of the formula:

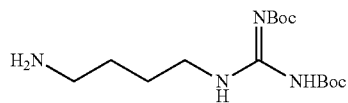

were reacted with the compound of the formula:

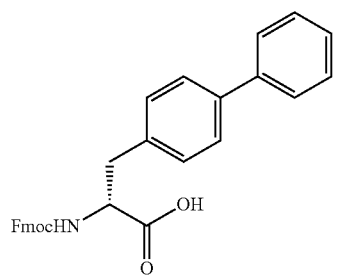

which can be prepared according to known methods. For instance one of such compounds is commercially available from Merck Millipore, GL Biochem China or Creosalus Advanced Chemtech as "Fmoc-4-phenyl-D-Phe-OH", "Fmoc-4-phenyl-D-Phe-OH" or "Fmoc-D-Bip-OH".

The amide/peptide coupling reagent can be customary coupling reagents such as 2-(1H-Benzotriazole-1-yl)-1,1,3,3-tetramethyluronium hexafluorophosphate (HBTU). Other suitable coupling reagents include N,N'-Dicyclohexylcarbodiimide (DCC), (N,N'-Diisopropylcarbodiimide (DIC), (1-[Bis(dimethylamino)methylene]-1H-1,2,3-triazolo[4,5-b]pyridinium 3-oxid hexafluorophosphate (HATU), 2-(6-Chloro-1H-benzotriazole-1-yl)-1,1,3,3-tetramethylaminium hexafluorophosphate (HCTU), benzotriazol-1-yl-oxytripyrrolidinophosphonium hexafluorophosphate (PyBop), 6-Chloro-benzotriazole-1-yloxy-tris-pyrrolidinophosphonium hexafluorophosphate (Pyclock) or Ethyl 2-Cyano-2-(hydroxyimino)acetate (Oxyma). Preferably these coupling reagents are used in the presence of a base such as for instance a tertiary amine, preferably N, N-Diisopropylamine.

The reaction temperatures in this process step can be varied in a relatively wide range. In general the process is carried out at temperatures of 0 to 100° C., preferably 15 to 60° C., most preferably at room temperature.

When carrying out this process step the starting materials are generally each employed in approximately equal amount. It may be beneficial to use the compound Fmoc-4-phenyl-Phe-OH in small excess.

Work up is done by customary separation methods, preferably by washing steps and an evaporation of the solvent. Dissolution and further post-reaction with a base, such as 1,8-Diazabicyclo[5.4.0]undec-7-ene (DBU), at room temperature and flash chromatography is possible.

In a third reaction step the obtained compound of the formula:

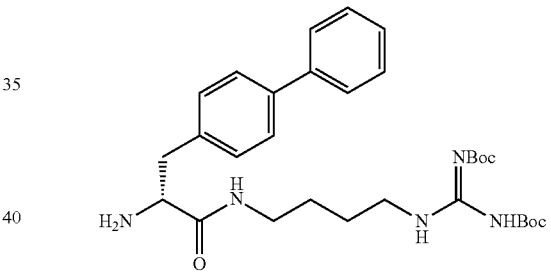

was reacted with a compound of one of the formulae:

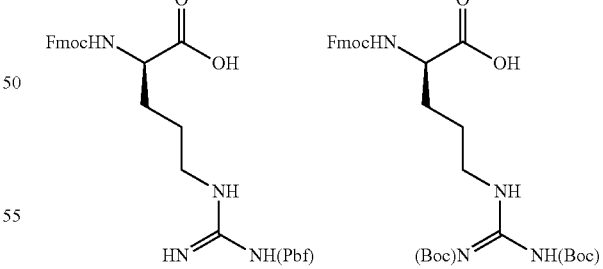

Such compounds are known or can be prepared according to known methods. For instance one of such compounds is commercially available from Merck Millipore, GL Biochem, or Creosalus Advanced Chemtech as "Fmoc-D-Arg(Pbf)-OH" or "Fmoc-D-Arg(Boc)$_2$-OH".

The amide/peptide coupling reagent can be customary coupling reagents such as 2-(1H-Benzotriazole-1-yl)-1,1,3,3-tetramethyluronium hexafluorophosphate (HBTU). Other suitable coupling reagents include N,N'-Dicyclohexylcarbodiimide (DCC), (N,N'-Diisopropylcarbodiimide (DIC), (1-[Bis(dimethylamino)methylene]-1H-1,2,3-triazolo[4,5-b]pyridinium 3-oxid hexafluorophosphate (HATU), 2-(6-Chloro-1H-benzotriazole-1-yl)-1,1,3,3-tetramethylaminium hexafluorophosphate (HCTU), benzotriazol-1-yl-oxytripyrrolidinophosphonium hexafluorophosphate (PyBop), 6-Chloro-benzotriazole-1-yloxy-tris-pyrrolidinophosphonium hexafluorophosphate (Pyclock) or Ethyl 2-Cyano-2-(hydroxyimino)acetate (Oxyma). Preferably these coupling reagents are used in the presence of a base such as for instance a tertiary amine, preferably N, N-Diisopropylamine.

Suitable solvents include inert organic solvents such as dimethylformamide.

The reaction temperatures in this process step can be varied in a relatively wide range. In general the process is carried out at temperatures of 0 to 100° C., preferably 15 to 60° C., most preferably at room temperature.

When carrying out this process step the starting materials and the compound of formula are generally each employed in approximately equal amount. It may be beneficial to use Fmoc-D-Arg(Pbf)-OH or Fmoc-D-Arg(Boc)$_2$-OH in excess.

Work up is done by customary separation methods, preferably by washing steps and an evaporation of the solvent. Dissolution and further post reaction with a base, such as 1,8-Diazabicyclo[5.4.0]undec-7-ene (DBU), at room temperature and flash chromatography is possible.

In a fourth reaction step the obtained compound of the formula

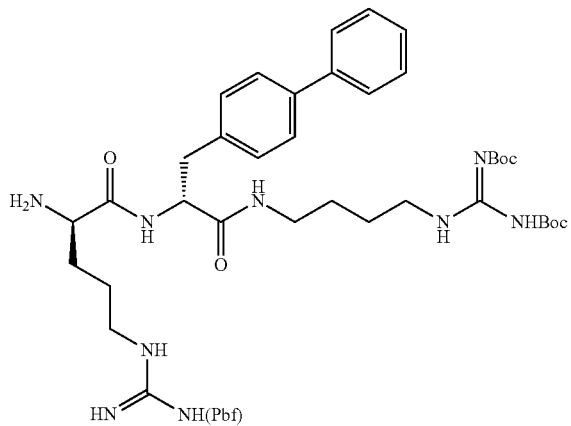

was reacted with a compound of the formula:

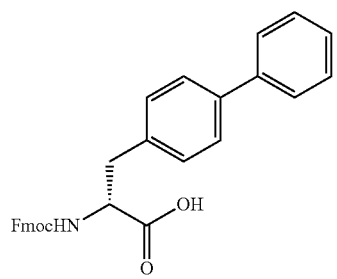

which is known or can be prepared according to known methods.

For instance one of such compounds is commercially available from Merck Millipore, GL Biochem China or Creosalus Advanced Chemtech as "Fmoc-4-phenyl-D-Phe-OH", "Fmoc-4-phenyl-D-Phe-OH" or "Fmoc-D-Bip-OH".

The amide/peptide coupling reagent can be customary coupling reagents such as 2-(1H-Benzotriazole-1-yl)-1,1,3,3-tetramethyluronium hexafluorophosphate (HBTU). Other suitable coupling reagents include N,N'-Dicyclohexylcarbodiimide (DCC), (N,N'-Diisopropylcarbodiimide (DIC), (1-[Bis(dimethylamino)methylene]-1H-1,2,3-triazolo[4,5-b]pyridinium 3-oxid hexafluorophosphate (HATU), 2-(6-Chloro-1H-benzotriazole-1-yl)-1,1,3,3-tetramethylaminium hexafluorophosphate (HCTU), benzotriazol-1-yl-oxytripyrrolidinophosphonium hexafluorophosphate (PyBop), 6-Chloro-benzotriazole-1-yloxy-tris-pyrrolidinophosphonium hexafluorophosphate (Pyclock) or Ethyl 2-Cyano-2-(hydroxyimino)acetate (Oxyma). Preferably these coupling reagents are used in the presence of a base such as for instance a tertiary amine, preferably N, N-Diisopropylamine.

Suitable solvents include inert organic solvents such as dimethylformamide.

The reaction temperatures in this process step can be varied in a relatively wide range. In general the process is carried out at temperatures of 0 to 100° C., preferably 15 to 60° C., most preferably at room temperature.

When carrying out this process step the reaction materials are generally each employed in approximately equal amount. It may be beneficial to use the compound Fmoc-4-phenyl-D-Phe-OH in excess.

Work up is done by customary separation methods, preferably by washing steps and an evaporation of the solvent. Dissolution and further post-reaction with a base, such as diazabicycloundecene (DBU), at room temperature and flash chromatography is possible.

Finally a precursor of the compound is obtained of the formula:

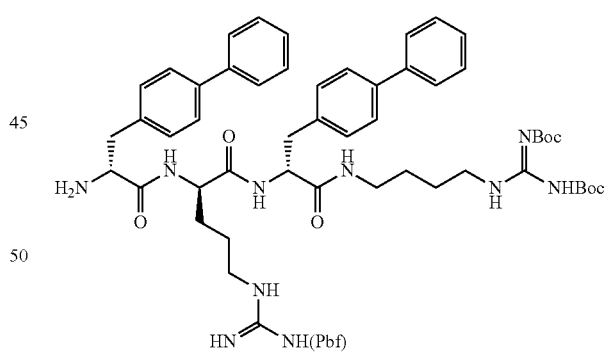

The compound of the formula (A) was obtained from the precursor by reaction with a strong organic acid such as trifluoroacetic acid. Such organic acids must be able to remove the Pbf and Boc moieties.

The reaction temperatures in this process step can be varied in a relatively wide range. In general the process is carried out at temperatures of 0 to 100° C., preferably 15 to 60° C., most preferably at room temperature.

Work up is done by customary separation methods, preferably by evaporation of the solvent, re-dissolution, chromatography and HPLC.

Example 4a: Additional Preparation Example: Synthetic Protocol for Making of the Compound of Formula (A)

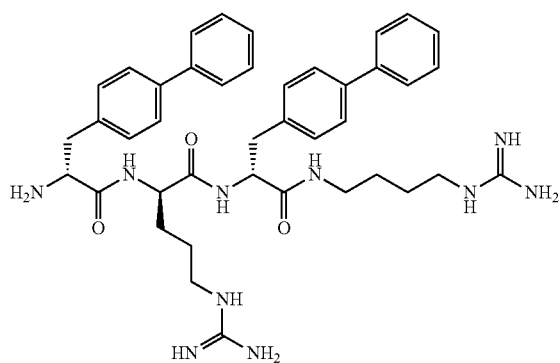

(A)

1. Anchor Fmoc-(D-Bip)-OH (1 mmol, 463.5 mg, 2 eq.) to 2-chlorotrityl chloride resin (510 mg, 0.5 mmol scale) with DIPEA (1 mmol, 0.174 mL, 2 eq.) in $CH_2Cl_2$ (10 mL) for 60 minutes.
2. Filter off excess solvent/reagents and wash resin with $CH_2Cl_2$ (~10 mL×2), $CH_3OH$ (~10 mL×2) followed by DMF (~10 mL×2).
3. Remove Fmoc using piperidine:DMF (20% v/v) with stirring for 30 minutes at room temperature.
4. Filter off excess solvent/reagents and wash resin with DMF (~10 mL×2), $CH_3OH$ (~10 mL×2) followed by DMF (~10 mL×2).
5. Dissolve Fmoc-(D-Arg)-OH (1 mmol, 648.7 mg, 2 eq.), HBTU (1 mmol, 380 mg, 2 eq.), DIPEA (1 mmol, 0.174 mL, 2 eq.) in DMF (10 mL) and allow this mixture to react with the resin for 60 minutes at room temperature.
6. Repeat step 4.
7. Repeat step 3.
8. Repeat step 4.
9. Dissolve Fmoc-(D-Bip)-OH (1 mmol, 463.5 mg, 2 eq.), HBTU (1 mmol, 380 mg, 2 eq.), DIPEA (1 mmol, 0.174 mL, 2 eq.) in DMF (10 mL) and allow this mixture to react with the resin for 60 minutes at room temperature.
10. Repeat step 4.
11. Repeat step 3.
12. Repeat step 4.
13. Dissolve $Boc_2O$ (1 mmol, 218.3 mg, 2 eq.) and DIPEA (1 mmol, 0.174 mL, 2 eq.) in DMF (10 mL) and allow this mixture to react with the resin for 60 minutes at room temperature.
14. Filter off excess solvent/reagents and wash resin with DMF (~10 mL×2), $CH_3OH$ (~10 mL×2) followed by $CH_2Cl_2$ (~10 mL×2).
15. Add 10% acetic acid in $CH_2Cl_2$ (v/v) to the resin and stir (room temperature, 60 minutes)
16. Filter the mixture and neutralise the solution with $NaHCO_3$ until no effervescence is seen.
17. Extract with $CH_2Cl_2$ and brine. The organic layer was concentrated in vacuo to yield crude Boc-brb-OH as a yellow oil.
18. Mix crude Boc-brb-OH with $NH_2$—$(CH_2)_4$-guanidine $(Boc)_2$ (0.6 mmol, 199 mg, 1.2 eq.), DIC (1.0 mmol, 0.157 mL) and HOAt (1-Hydroxy-7-azabenzotriazole obtained from GL Biochem, 1.0 mmol, 136 mg) in DMF (5 mL) and allow this mixture to react overnight at room temperature.
19. The reaction mixture was extracted using EtOAc/brine and the organic layer was concentrated in vacuo to yield a yellow oil.
20. Remove the Boc and Pbf with TFA and two drops of water at room temperature for 60 minutes.
21. Excess TFA was blown off with a $N_2$ gas stream (~20 min for 1 mL) to yield the crude target as a yellow oil.
22. Purify the yellow oil with C18 Reverse Phase HPLC (18% initial acetonitrile concentration) to obtain the target as a white powder (86.6 mg, 23% overall yield).

Example 4b: Biological Activity of Compound (A)

According to the biological examples the MIC values (µM) of compound (A) for a panel of MRSA strains are:

| | |
|---|---|
| ATCC-BAA-44 | 3.125 |
| ATCC-1720 | 3.125 |
| ATCC-2094 | 3.125 |
| ATCC-33591 | 1.5625 |
| ATCC-BAA-1680 | 1.5625 |
| ATCC-BAA-1681 | 3.125 |
| ATCC-700699 | 3.125 |

Example 5: Synthetic Protocol for Making Compounds 10 and 11

Figure 4:
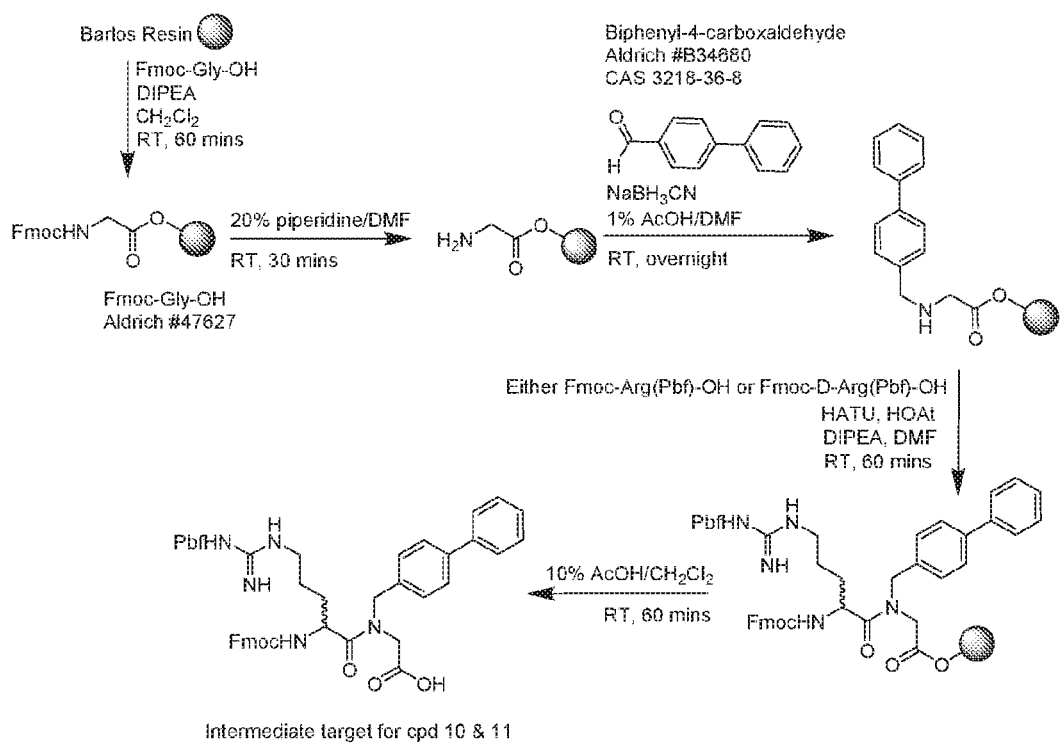
FIG. 4 shows a synthetic route of making an intermediate target, (Fmoc-Arg-(B-peptoid)-OH), of compounds 10 and 11.

For making the compounds 10 and 11 (see below) an intermediate target has been obtained as shown by the synthetic route of FIG. 4.
This translated in the following synthetic protocol:
1. Stir Fmoc-Gly-OH (commercially available from Anaspec, Sigma/Aldrich, Bachem, Creosalus AdvancedChemTech, GL Biochem China, Novabiochem), DIPEA and Barlos resin (commercially available from Anaspec, Sigma/Aldrich, Bachem, Creosalus AdvancedChemTech, GL Biochem China, Novabiochem) in $CH_2Cl_2$ at room temperature for 1 h.
2. Drain solvent and excess reagents from resin.
3. Wash resin with $CH_2Cl_2$ followed by DMF.
4. Introduce 20% piperidine/DMF (v/v) to the resin and stir at room temperature for 30 minutes.
5. Repeat step 2.
6. Wash resin with DMF, $CH_3OH$ followed by DMF.
7. Introduce Biphenyl-4-carboxaldehyde (purchased from Sigma/Aldrich), $NaBH_3CN$ and 1% AcOH/DMF (v/v) to the resin and stir at room temperature overnight.
8. Repeat steps 2 and 6.
9. Introduce either Fmoc-Arg(Pbf)-OH or Fmoc-D-Arg(Pbf)-OH, HATU, DIPEA and HOAt dissolved in DMF to the resin and stir at room temperature for 1 h.
10. Repeat step 2.
11. Wash resin with DMF, $CH_3OH$ followed by $CH_2Cl_2$.
12. Add 10% $AcOH/CH_2Cl_2$ (v/v) to the resin and stir at room temperature for 1 h.
13. Filter and collect the solvent containing the intermediate target (Fmoc-Arg-(B-peptoid)-OH), neutralise excess AcOH with $NaHCO_3$ and extract with $CH_2Cl_2$ before flash chromatography purification.

From this intermediate the compounds 10 and 11 have been synthesized:

Synthetic Protocol for Compound 10

1. Anchor Fmoc-Arg-(B-peptoid)-OH (1.0 mmol, 2 eq.) to 2-chlorotrityl chloride resin (0.5 mmol scale) with DIPEA (1.0 mmol, 2 eq.) in $CH_2Cl_2$ (10 mL) for 60 minutes.
2. Filter off excess solvent/reagents and wash resin with $CH_2Cl_2$ (~10 mL×2), $CH_3OH$ (~10 mL×2) followed by DMF (~10 mL×2).
3. Remove Fmoc using piperidine:DMF (20% v/v) with stirring for 30 minutes at room temperature.
4. Filter off excess solvent/reagents and wash resin with DMF (~10 mL×2), $CH_3OH$ (~10 mL×2) followed by DMF (~10 mL×2).
5. Dissolve Fmoc-Bip-OH (1.0 mmol, 2 eq.), HBTU (1.0 mmol, 2 eq.), DIPEA (1.0 mmol, 2 eq.) in DMF (10 mL) and allow this mixture to react with the resin for 60 minutes at room temperature.
6. Repeat step 4.
7. Repeat step 3.
8. Repeat step 4.
9. Dissolve $Boc_2O$ (1.0 mmol, 2 eq.) and DIPEA (1.0 mmol, 2 eq.) in DMF (10 mL) and allow this mixture to react with the resin for 60 minutes at room temperature.
10. Filter off excess solvent/reagents and wash resin with DMF (~10 mL×2), $CH_3OH$ (~10 mL×2) followed by $CH_2Cl_2$ (~10 mL×2).
11. Add 10% acetic acid in $CH_2Cl_2$ (v/v) to the resin and stir (room temperature, 60 minutes)
12. Filter the mixture and neutralise the solution with $NaHCO_3$ until no effervescence is seen.
13. Extract with $CH_2Cl_2$ and brine. The organic layer was concentrated in vacuo to yield crude Boc-Bip-Arg-(B-peptoid)-OH as a yellow oil.
14. React 1,4-diaminobutane (0.8 mmol, 2 eq) with 1,3-bis(tert-butoxycarbonyl)-2-methyl-2-thiopseudourea (0.4 mmol) and DIPEA (2.4 mmol, 6 eq.) in $CH_2Cl_2$ (10 mL) for 60 minutes.
15. Purify the mixture with flash chromatography using hexane, EtOAc, $CH_2Cl_2$ and $CH_3OH$ to obtain $NH_2$—$(CH_2)_4$-guanidine$(Boc)_2$ as a white solid.
16. Mix crude Boc-Bip-Arg-(B-peptoid)-OH with $NH_2$—$(CH_2)_4$-guanidine$(Boc)_2$, DIC (1.0 mmol) and HOAt (1.0 mmol) in DMF (5 mL) and allow this mixture to react overnight at room temperature.
17. The reaction mixture was extracted using EtOAc/brine and the organic layer was concentrated in vacuo to yield a yellow oil.
18. Remove the Boc and Pbf with TFA and two drops of water at room temperature for 60 minutes.
19. Excess TFA was blown off with a $N_2$ gas stream (~20 min for 1 mL) to yield the crude target as a yellow oil.
20. Purify the yellow oil with C18 Reverse Phase HPLC (18% initial acetonitrile concentration) to obtain target as a colourless oil (24 mg, 6.5%).

Synthetic Protocol for Compound 11

1. Anchor Fmoc-(D-Arg)-(B-peptoid)-OH (1.0 mmol, 2 eq.) to 2-chlorotrityl chloride resin (0.5 mmol scale) with DIPEA (1.0 mmol, 2 eq.) in $CH_2Cl_2$ (10 mL) for 60 minutes.
2. Filter off excess solvent/reagents and wash resin with $CH_2Cl_2$ (~10 mL×2), $CH_3OH$ (~10 mL×2) followed by DMF (~10 mL×2).
3. Remove Fmoc using piperidine:DMF (20% v/v) with stirring for 30 minutes at room temperature.
4. Filter off excess solvent/reagents and wash resin with DMF (~10 mL×2), $CH_3OH$ (~10 mL×2) followed by DMF (~10 mL×2).
5. Dissolve Fmoc-(D-Bip)-OH (1.0 mmol, 2 eq.), HBTU (1.0 mmol, 2 eq.), DIPEA (1.0 mmol, 2 eq.) in DMF (10 mL) and allow this mixture to react with the resin for 60 minutes at room temperature.
6. Repeat step 4.
7. Repeat step 3.
8. Repeat step 4.
9. Dissolve $Boc_2O$ (1.0 mmol, 2 eq.) and DIPEA (1.0 mmol, 2 eq.) in DMF (10 mL) and allow this mixture to react with the resin for 60 minutes at room temperature.
10. Filter off excess solvent/reagents and wash resin with DMF (~10 mL×2), $CH_3OH$ (~10 mL×2) followed by $CH_2Cl_2$ (~10 mL×2).
11. Add 10% acetic acid in $CH_2Cl_2$ (v/v) to the resin and stir (room temperature, 60 minutes)
12. Filter the mixture and neutralise the solution with $NaHCO_3$ until no effervescence is seen.
13. Extract with $CH_2Cl_2$ and brine. The organic layer was concentrated in vacuo to yield crude Boc-bip-arg-(B-peptoid)-OH as a yellow oil.
14. React 1,4-diaminobutane (0.4 mmol, 2 eq) with 1,3-bis(tert-butoxycarbonyl)-2-methyl-2-thiopseudourea (0.2 mmol) and DIPEA (1.2 mmol, 6 eq.) in $CH_2Cl_2$ (10 mL) for 60 minutes.
15. Purify the mixture with flash chromatography using hexane, EtOAc, $CH_2Cl_2$ and $CH_3OH$ to obtain $NH_2$—$(CH_2)_4$-guanidine$(Boc)_2$ as a white solid.
16. React crude Boc-bip-arg-(B-peptoid)-OH with $NH_2$—$(CH_2)4$-guanidine$(Boc)_2$, DIC (1.2 mmol) and HOAt in DMF (5 mL) and allow this mixture to react overnight at room temperature.
17. The reaction mixture was extracted using EtOAc/brine and the organic layer was concentrated in vacuo to yield a yellow oil.
18. Remove the Boc and Pbf with TFA and two drops of water at room temperature for 60 minutes.
19. Excess TFA was blown off with a $N_2$ gas stream (~20 min for 1 mL) to yield the crude target as a yellow oil.
20. Purify the yellow oil with C18 Reverse Phase HPLC (18% initial acetonitrile concentration) to obtain target as a yellow oil (0.8 mg, 0.4%).

Synthetic Protocol for Compounds 13 to 22

1. Anchor the first Fmoc-protected amino acid (1.0 mmol, 2 eq.) to 2-chlorotrityl chloride resin (0.5 mmol scale) with diisopropylamine (DIPEA) (1.0 mmol, 2 eq.) in $CH_2Cl_2$ (10 mL) and stir for 60 minutes at room temperature.
2. Filter off excess solvent/reagents and wash resin with $CH_2Cl_2$ (~10 mL×2), $CH_3OH$ (~10 mL×2) followed by DMF (~10 mL×2).
3. Remove Fmoc protecting group using piperidine:DMF (20% v/v) by stirring for 30 minutes at room temperature.
4. Filter off excess solvent/reagents and wash resin with DMF (~10 mL×2), $CH_3OH$ (~10 mL×2) followed by DMF (~10 mL×2).
5. Dissolve the second Fmoc-protected amino acid (1.0 mmol, 2 eq.), HBTU (1.0 mmol, 2 eq.), DIPEA (1.0 mmol, 2 eq.) in DMF (10 mL) and allow this mixture to react with the resin for 60 minutes at room temperature.
6. Repeat step 4.
7. Repeat step 3.
8. Repeat step 4.
9. Dissolve the third Fmoc-protected amino acid (1.0 mmol, 2 eq.), HBTU (1.0 mmol, 2 eq.), DIPEA (1.0 mmol, 2 eq.) in DMF (10 mL) and allow this mixture to react with the resin for 60 minutes at room temperature.
10. Repeat step 4.
11. Repeat step 3.

12. Repeat step 4.

13. Dissolve Boc$_2$O (1.0 mmol, 2 eq.) and DIPEA (1.0 mmol, 2 eq.) in DMF (10 mL) and allow this mixture to cap the on-resin peptide for 60 minutes at room temperature.

14. Filter off excess solvent/reagents and wash resin with DMF (~10 mL×2), CH$_3$OH (~10 mL×2) followed by CH$_2$Cl$_2$ (~10 mL×2).

15. Separate the Boc-protected peptide intermediate from the resin by adding 10% acetic acid in CH$_2$Cl$_2$ (v/v) to the resin and stir for 60 minutes at room temperature.

16. Filter the mixture and neutralise the solution with NaHCO$_3$ until no effervescence observed.

17. Extract with CH$_2$Cl$_2$ and brine. The organic layer was concentrated in vacuo to yield crude Boc-protected peptide intermediate as an oily liquid.

18. React 1,4-diaminobutane (0.4 mmol, 2 eq) with 1,3-bis(tert-butoxycarbonyl)-2-methyl-2-thiopseudourea (0.2 mmol) and DIPEA (1.2 mmol, 6 eq.) in CH$_2$Cl$_2$ (10 mL) for 60 minutes at room temperature.

19. Purify the mixture with flash chromatography using hexane, ethyl acetate, CH$_2$Cl$_2$ and CH$_3$OH to obtain NH$_2$—(CH$_2$)$_4$-guanidine(Boc)$_2$ as a white solid.

20. Couple the crude Boc-protected peptide intermediate with NH$_2$—(CH$_2$)$_4$-guanidine(Boc)$_2$, DIC (1.2 mmol) and HOAt in DMF (5 mL) overnight at room temperature.

21. The reaction mixture was extracted using ethyl acetate/brine and the organic layer was concentrated in vacuo to yield a yellow oil.

22. Remove the Boc and Pbf with TFA mixed with two drops of water for 60 minutes at room temperature.

23. Excess TFA was blown off with a N$_2$(g) stream (~20 min for 1 mL) to yield the crude target as a yellow oil.

24. Purify the yellow oil by Reverse Phase HPLC to obtain target as a yellow oil (~1 mg, ~0.4% overall yield).

Synthetic Protocol Compounds 23 to 25

1. Anchor the first Fmoc-protected amino acid (1.0 mmol, 2 eq.) to 2-chlorotrityl chloride resin (0.5 mmol scale) with diisopropylamine (DIPEA) (1.0 mmol, 2 eq.) in CH$_2$Cl$_2$ (10 mL) and stir for 60 minutes at room temperature (room temperature).

2. Filter off excess solvent/reagents and wash resin with CH$_2$Cl$_2$ (~10 mL×2), CH$_3$OH (~10 mL×2) followed by DMF (~10 mL×2). 3. Remove Fmoc protecting group using piperidine:DMF (20% v/v) by stirring for 30 minutes at room temperature.

4. Filter off excess solvent/reagents and wash resin with DMF (~10 mL×2), CH$_3$OH (~10 mL×2) followed by DMF (~10 mL×2).

5. Dissolve the second Fmoc-protected amino acid (1.0 mmol, 2 eq.), HBTU (1.0 mmol, 2 eq.), DIPEA (1.0 mmol, 2 eq.) in DMF (10 mL) and allow this mixture to react with the resin for 60 minutes at room temperature.

6. Repeat step 4.

7. Repeat step 3.

8. Repeat step 4.

9. Dissolve the third Fmoc-protected amino acid (1.0 mmol, 2 eq.), HBTU (1.0 mmol, 2 eq.), DIPEA (1.0 mmol, 2 eq.) in DMF (10 mL) and allow this mixture to react with the resin for 60 minutes at room temperature.

10. Repeat step 4.

11. Repeat step 3.

12. Repeat step 4.

13. Dissolve the appropriate organic acid, RCOOH (2.0 mmol, 2 eq.), DIC (2.0 mmol, 2 eq.) and HOAt in 1:1 CH$_2$Cl$_2$/DMF (10 mL) and allow this mixture to react with the on-resin peptide intermediate overnight at room temperature.

14. Filter off excess solvent/reagents and wash resin with DMF (~10 mL×2), CH$_3$OH (~10 mL×2) followed by CH$_2$Cl$_2$ (~10 mL×2).

15. Separate the peptide intermediate from the resin by adding 10% acetic acid in CH$_2$Cl$_2$ (v/v) to the resin and stir for 60 minutes at room temperature.

16. Filter the mixture and neutralise the solution with NaHCO3 until no effervescence observed.

17. Extract with CH$_2$Cl$_2$ and brine. The organic layer was concentrated in vacuo to yield crude Boc-protected peptide intermediate as an oily liquid.

18. React 1,4-diaminobutane (0.4 mmol, 2 eq) with 1,3-bis(tert-butoxycarbonyl)-2-methyl-2-thiopseudourea (0.2 mmol) and DIPEA (1.2 mmol, 6 eq.) in CH$_2$Cl$_2$ (10 mL) for 60 minutes at room temperature.

19. Purify the mixture with flash chromatography using hexane, ethyl acetate, CH$_2$Cl$_2$ and CH$_3$OH to obtain NH$_2$—(CH$_2$)4-guanidine(Boc)$_2$ as a white solid.

20. Couple the crude peptide intermediate with NH$_2$—(CH$_2$)$_4$-guanidine(Boc)$_2$, DIC (1.2 mmol) and HOAt in DMF (5 mL) overnight at room temperature.

21. The reaction mixture was extracted using ethyl acetate/brine and the organic layer was concentrated in vacuo to yield a yellow oil.

22. Remove any acid-labile protecting group with TFA mixed with two drops of water for 60 minutes at room temperature.

23. Excess TFA was blown off with a N$_2$(g) stream (~20 min for 1 mL) to yield the crude target as a yellow oil.

24. Purify the yellow oil by Reverse Phase HPLC to obtain target as a off-white powder (~1 mg, ~0.4% overall yield).

Synthetic Protocol Compound 27

1. Anchor Fmoc-Bip-OH (1 mmol, 2 eq.) to 2-chlorotrityl chloride resin (0.5 mmol scale) with DIPEA (1 mmol, 2 eq.) in CH$_2$Cl$_2$ (10 mL) for 60 minutes at room temperature.

2. Filter off excess solvent/reagents and wash resin with CH$_2$Cl$_2$ (~10 mL×2), CH$_3$OH (~10 mL×2) followed by DMF (~10 mL×2).

3. Remove Fmoc using piperidine:DMF (20% v/v) with stirring for 30 minutes at room temperature.

4. Filter off excess solvent/reagents and wash resin with DMF (~10 mL×2), CH$_3$OH (~10 mL×2) followed by DMF (~10 mL×2).

5. Dissolve Fmoc-Arg(Pbf)-OH (obtainable from Sigma, 1 mmol, 2 eq.), HBTU (1 mmol, 2 eq.), DIPEA (1 mmol, 2 eq.) in DMF (10 mL) and allow this mixture to react with the resin for 60 minutes at room temperature.

6. Repeat step 4.

7. Repeat step 3.

8. Repeat step 4.

9. Dissolve Fmoc-Bip-OH (1 mmol, 2 eq.), HBTU (1 mmol, 2 eq.), DIPEA (1 mmol, 2 eq.) in DMF (10 mL) and allow this mixture to react with the resin for 60 minutes at room temperature.

10. Repeat step 4.

11. Repeat step 3.

12. Repeat step 4.

13. Dissolve Boc$_2$O (1 mmol, 2 eq.) and DIPEA (1 mmol, 2 eq.) in DMF (10 mL) and allow this mixture to react with the resin for 60 minutes at room temperature.

14. Filter off excess solvent/reagents and wash resin with DMF (~10 mL×2), CH$_3$OH (~10 mL×2) followed by CH$_2$Cl$_2$ (~10 mL×2).

15. Add 10% acetic acid in CH$_2$Cl$_2$ (v/v) to the resin and stir (room temperature, 60 minutes)

16. Filter the mixture and neutralise the solution with NaHCO$_3$ until no effervescence is seen.

17. Extract with CH$_2$Cl$_2$ and brine. The organic layer was concentrated in vacuo to yield crude Boc-BRB-OH as a yellow oil.

18. React crude Boc-BRB-OH with N,O-dimethylhydroxylamine hydrochloride (obtainable from Sigma-Aldrich, 0.6 mmol, 1.2 eq.), DIC (0.6 mmol, 1.2 eq.) and DIPEA (0.6 mmol, 1.2 eq.) in DMF for 60 minutes at room temperature.

19. Extract with EtOAc/brine, concentrate in vacuo and purify by flash chromatography to obtain Boc-BRB-Weinreb.

20. Dissolve Boc-BRB-Weinreb in THF (~10 mL) and cooled the solution to −78° C. Add LiAlH$_4$ (5 eq.) dropwise and allow the mixture to react for 10 minutes Et$_2$O (~15 mL) was then added and the mixture was allowed to warm to room temperature. Add citric acid (0.1M) dropwise and stir the mixture for 30 minutes The mixture was then extracted with Et$_2$O/brine and concentrated in vacuo to yield Boc-BRB-H as a yellowish solid.

21. Mix Boc-BRB-H with NH$_2$—(CH$_2$)$_4$-guanidine (Boc)$_2$ (0.6 mmol, 1.2 eq.) and NaBH$_3$CN (3.0 mmol, 6 eq.) in 1% acetic acid/DMF (5 mL) and allow this mixture to react overnight at room temperature.

22. Extract using ethyl acetate/brine and concentrate in vacuo to yield a yellow oil.

23. Remove any acid-labile protecting groups with TFA and two drops of water for 60 minutes at room temperature.

24. Excess TFA was blown off with a N$_2$(g) stream to yield the crude target as a yellow oil.

25. Purify the yellow oil with C18 Reverse Phase HPLC (18% initial CH$_3$CN concentration) to obtain target as a colourless gel (6.2 mg, 1.7%).

Synthetic Protocol Compound 28

1. React Fmoc-Bip-OH (0.6 mmol, 1.2 eq.) with NH$_2$—(CH$_2$)$_4$-guanidine(Boc)$_2$ (0.5 mmol), DIC (0.6 mmol, 1.2 eq.) and HOAt in DMF (10 mL) for 3 h. at room temperature.

2. Extract with ethyl acetate/brine and concentrate the organic layer in vacuo.

3. Remove Fmoc using DBU (0.75 mmol, 1.5 eq.) in CH$_2$Cl$_2$ and allow the mixture to react for 30 minutes at room temperature.

4. Evaporate the solvent and purify the residue using flash chromatography to yield NH$_2$—Bip-Ag(Boc)$_2$.

5. Anchor Fmoc-Arg-OH (1 mmol, 2 eq.) to 2-chlorotrityl chloride resin (0.5 mmol scale) with DIPEA (1 mmol, 2 eq.) in CH$_2$Cl$_2$ (10 mL) for 60 minutes at room temperature.

6. Filter off excess solvent/reagents and wash resin with CH$_2$Cl$_2$ (~10 mL×2), CH$_3$OH (~10 mL×2) followed by DMF (~10 mL×2).

7. Remove Fmoc using piperidine:DMF (20% v/v) with stirring for 30 minutes at room temperature.

8. Filter off excess solvent/reagents and wash resin with DMF (~10 mL×2), CH$_3$OH (~10 mL×2) followed by DMF (~10 mL×2).

9. Dissolve Fmoc-Bip-OH (1 mmol, 2 eq.), HBTU (1 mmol, 2 eq.), DIPEA (1 mmol, 2 eq.) in DMF (10 mL) and allow this mixture to react with the resin for 60 minutes at room temperature.

10. Repeat step 8.

11. Repeat step 7.

12. Repeat step 8.

13. Dissolve Boc$_2$O (1 mmol, 2 eq.) and DIPEA (1 mmol, 2 eq.) in DMF (10 mL) and allow this mixture to react with the resin for 60 minutes at room temperature.

14. Filter off excess solvent/reagents and wash resin with DMF (~10 mL×2), CH$_3$OH (~10 mL×2) followed by CH$_2$Cl$_2$ (~10 mL×2).

15. Add 10% acetic acid in CH$_2$Cl$_2$ (v/v) to the resin and stir for 60 minutes at room temperature.

16. Filter the mixture and neutralise the solution with NaHCO$_3$ until no effervescence is seen.

17. Extract with CH$_2$Cl$_2$ and brine. The organic layer was concentrated in vacuo to yield crude Boc-BR-OH as a yellow oil.

18. React crude Boc-BR-OH with N,O-dimethylhydroxylamine hydrochloride (0.6 mmol, 1.2 eq.), DIC (0.6 mmol, 1.2 eq.) and DIPEA (0.6 mmol, 1.2 eq.) in DMF for 60 minutes at room temperature.

19. Extract with ethylacetate/brine, concentrate in vacuo and purify by flash chromatography to obtain Boc-BR-Weinreb.

20. Dissolve Boc-BR-Weinreb in THF (~10 mL) and cool the solution to −78° C. Add LiAlH$_4$ (5 eq.) dropwise and allow the mixture to react for 10 minutes Et$_2$O (~15 mL) was then added and the mixture was allowed to warm to room temperature. Add citric acid (0.1M) dropwise and stir the mixture for 30 minutes The mixture was then extracted with Et$_2$O/brine and concentrated in vacuo to yield Boc-BR-H as a yellow solid.

21. Mix Boc-BR-H with NH$_2$—Bip-(CH$_2$)$_4$-guanidine (Boc)$_2$ (0.6 mmol, 1.2 eq.) and NaBH$_3$CN (3.0 mmol, 6 eq.) in 1% acetic acid/DMF (5 mL) and allow this mixture to react overnight at room temperature.

22. Extract using ethyl acetate/brine and concentrate in vacuo to yield a yellow oil.

23. Remove any acid-labile protecting group with TFA and two drops of water for 60 minutes at room temperature.

24. Excess TFA was blown off with a N$_2$(g) stream to yield the crude target as a yellow oil.

25. Purify the yellow oil with C18 Reverse Phase HPLC (18% initial CH$_3$CN concentration) to obtain target as a white powder (11.3 mg, 3.1%).

Synthetic Protocol Compound 29

1. React Fmoc-Bip-OH with N,O-dimethylhydroxylamine hydrochloride (0.6 mmol, 1.2 eq.), DIC (0.6 mmol, 1.2 eq.) and diisopropylethylamine (DIPEA) (0.6 mmol, 1.2 eq.) in DMF for 60 minutes at room temperature.

2. Extract with ethyl acetate/brine, concentrate in vacuo and purify using flash chromatography to yield Fmoc-Bip-Weinreb.

3. Dissolve Fmoc-Bip-Weinreb in THF (~10 mL) and cool the solution to −78° C. Add LiAlH$_4$ (5 eq.) dropwise and allow the mixture to react for 10 minutes; add diethyl ether (~15 mL) was and allow the mixture to warm to room temperature. Add citric acid (0.1M) dropwise and stir the mixture for 30 minutes The mixture was then extracted with diethyl ether/brine and concentrated in vacuo to yield Fmoc-Bip-H as a yellow gel.

4. Anchor Fmoc-Bip-OH (1 mmol, 2 eq.) to 2-chlorotrityl chloride resin (0.5 mmol scale) with DIPEA (1 mmol, 2 eq.) in CH$_2$Cl$_2$ (10 mL) for 60 minutes at room temperature.

5. Filter off excess solvent/reagents and wash resin with CH$_2$Cl$_2$ (~10 mL×2), CH$_3$OH (~10 mL×2) followed by DMF (~10 mL×2).

6. Remove Fmoc using piperidine:DMF (20% v/v) with stirring for 30 minutes at room temperature.

7. Filter off excess solvent/reagents and wash resin with DMF (~10 mL×2), CH$_3$OH (~10 mL×2) followed by DMF (~10 mL×2).

8. Dissolve Fmoc-Arg-OH (1 mmol, 2 eq.), HBTU (1 mmol, 2 eq.), DIPEA (1 mmol, 2 eq.) in DMF (10 mL) and allow this mixture to react with the resin for 60 minutes at room temperature.

9. Repeat step 7.

10. Repeat step 6.

11. Repeat step 7.

12. Dissolve Fmoc-Bip-H (1.5 mmol, 3 eq.) and NaBH$_3$CN (3 mmol, 6 eq.) in 1% acetic acid/DMF (10 mL) and allow this mixture to react with the resin overnight at room temperature.

13. Filter off excess solvent/reagents and wash resin with 1% acetic acid/DMF (~10 mL), 5% DIPEA/DMF (~10 mL), DMF (~10 mL×2), CH$_3$OH (~10 mL×2) followed by DMF (~10 mL×2) again.

14. Repeat step 6.

15. Repeat step 7.

16. Dissolve Boc$_2$O (1 mmol, 2 eq.) and DIPEA (1 mmol, 2 eq.) in DMF (10 mL) and allow this mixture to react with the resin for 60 minutes at room temperature.

17. Filter off excess solvent/reagents and wash resin with DMF (~10 mL×2), CH$_3$OH (~10 mL×2) followed by CH$_2$Cl$_2$ (~10 mL×2).

18. Add 10% acetic acid in CH$_2$Cl$_2$ (v/v) to the resin and stir for 60 minutes at room temperature.

19. Filter the mixture and neutralise the solution with NaHCO$_3$ until no effervescence is seen.

20. Extract with CH$_2$Cl$_2$ and brine. The organic layer was concentrated in vacuo to yield crude Boc-BCH$_2$RB-OH as a yellow oil.

21. Mix Boc-BCH$_2$RB-OH with NH$_2$—(CH$_2$)$_4$-guanidine (Boc)$_2$ (0.6 mmol, 1.2 eq.), DIC (0.6 mmol, 1.2 eq.) and HOAt in DMF (5 mL) and allow this mixture to react overnight at room temperature.

22. Extract using ethyl acetate/brine and concentrate in vacuo to yield a yellow oil.

23. Remove any acid-labile protecting groups with TFA and two drops of water for 60 minutes at room temperature.

24. Excess TFA was blown off with a N$_2$(g) stream to yield the crude target as a yellow oil.

25. Purify the yellow oil with C18 Reverse Phase HPLC (18% initial acetonitrile concentration) to obtain target as a colourless gel (1.1 mg, 0.3%).

According to the processes of the invention mentioned, the examples or known methods the following other compounds have been synthesized and their MIC value vs. MRSA (ATCC 33591) in μM determined:

Structure:

| Compound | MIC |
|---|---|
| 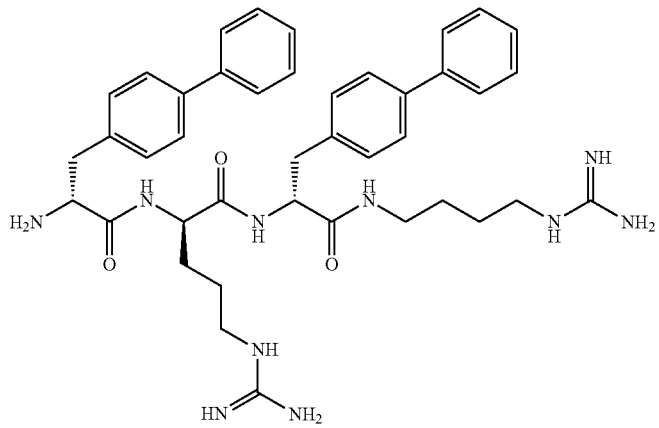 Compound 1 | 1.56 |
| 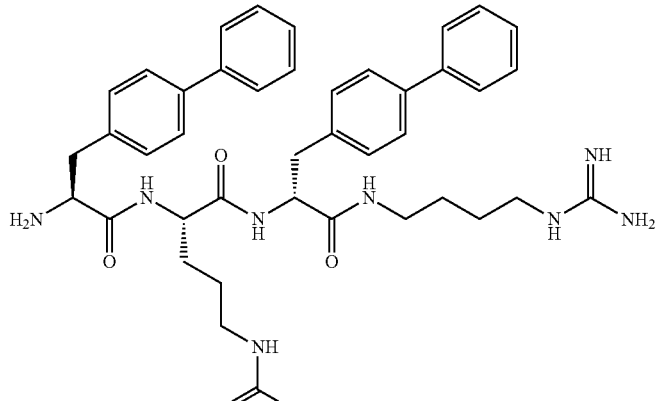 Compound 2 | 12.5 |

-continued
| Compound | MIC |
|---|---|
| 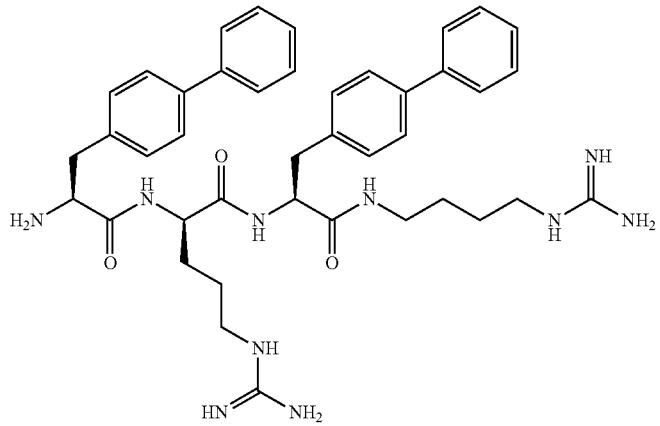<br>Compound 3 | 25 |
| 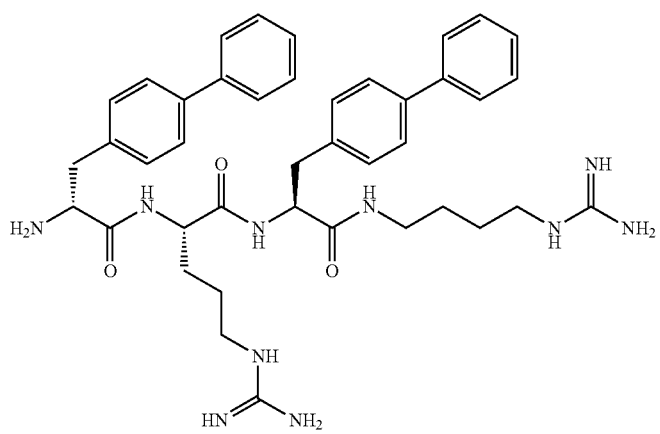<br>Compound 4 | 25 |
| 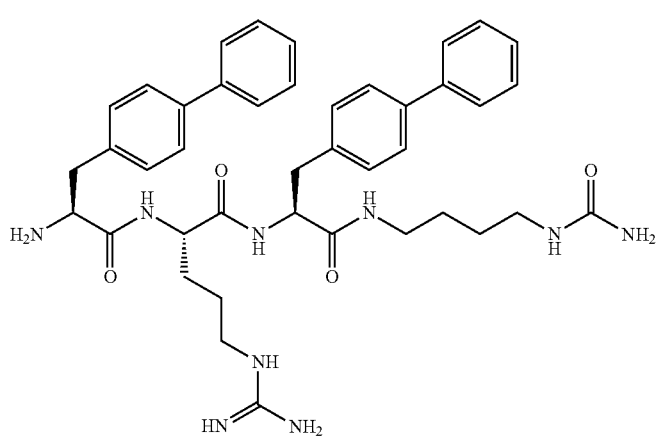<br>Compound 5 | 25 |

-continued
| Compound | MIC |
|---|---|
| 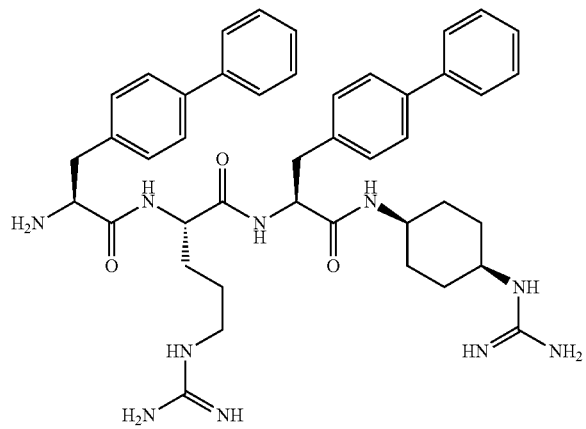<br>Compound 6 | 6.25 |
| 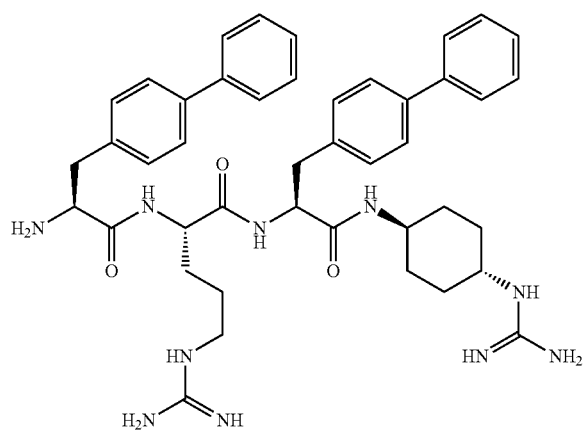<br>Compound 7 | 6.25 |
| 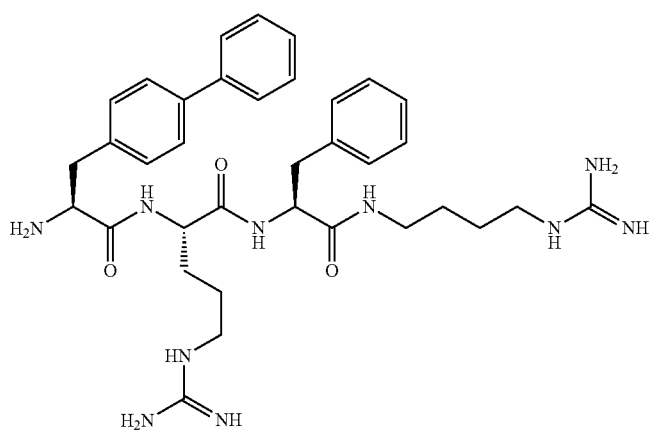<br>Compound 8 | 25 |

| Compound | MIC |
|---|---|
| 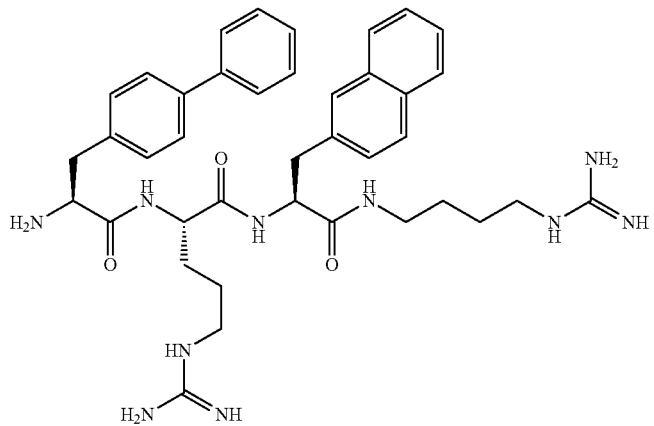
Compound 9 | 50 |
| 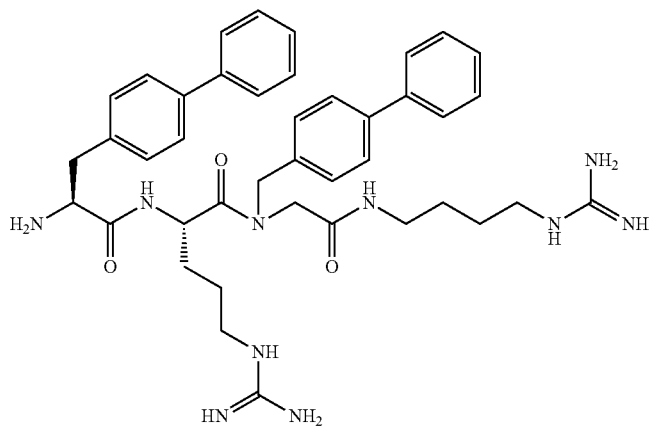
Compound 10 | 3.125 |
| 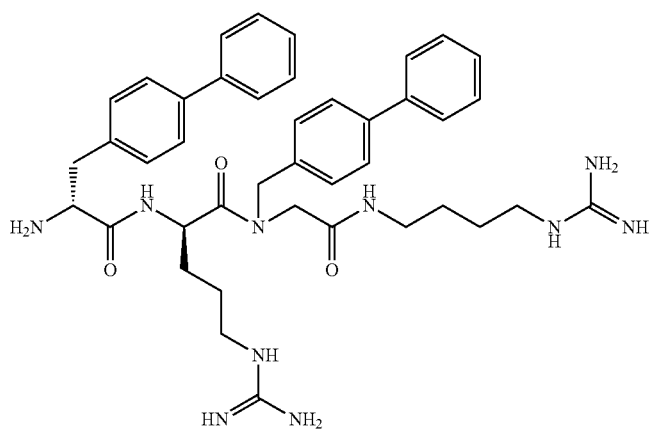
Compound 11 | 12.5 |

| Compound | MIC |
|---|---|
| | 12.5 |
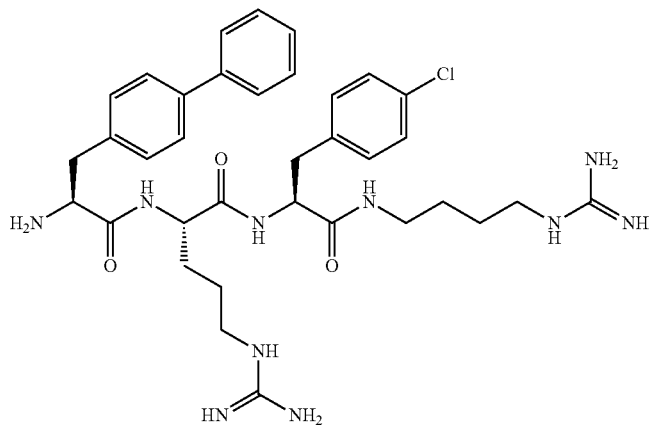
Compound 12
| | 6.25 |
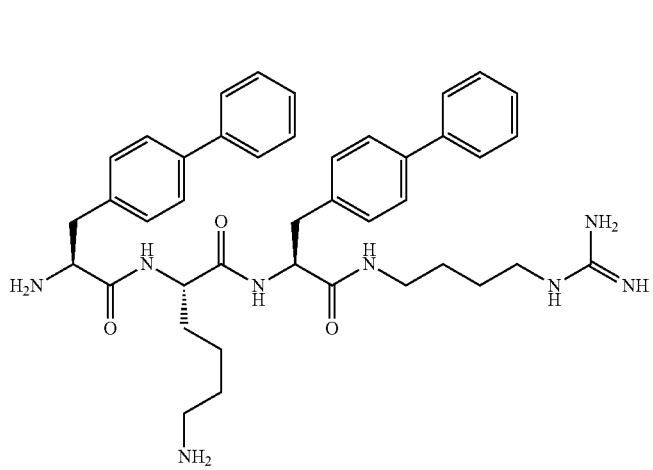 [SMILES: N=C(N)NCCCCNC(=O)[C@H](Cc1ccc(-c2ccccc2)cc1)NC(=O)[C@H](CCCN)NC(=O)[C@@H](N)Cc1ccc(-c2ccccc2)cc1]
Compound 13
| | 12.5 |
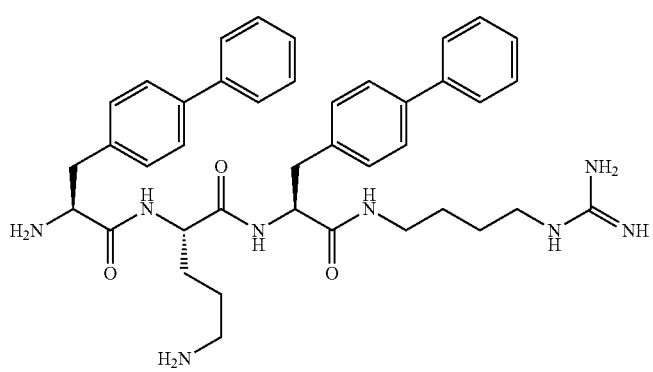
Compound 14

-continued
| Compound | MIC |
|---|---|
| | 12.5 |
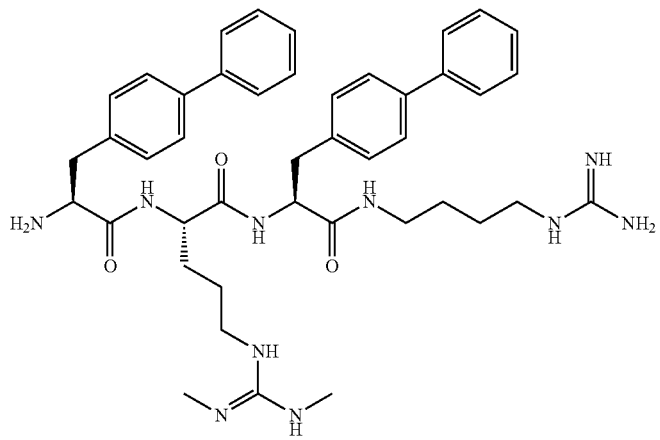
Compound 15
| | 25 |
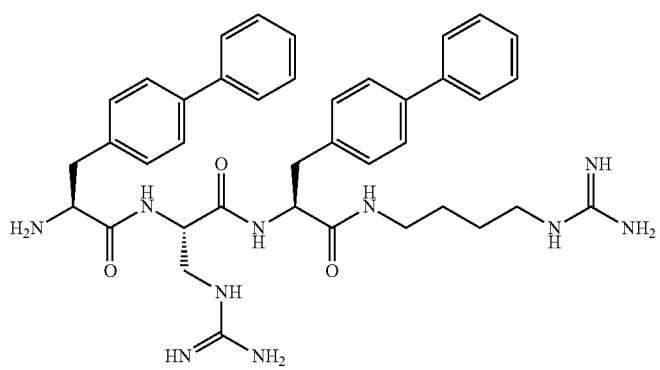
Compound 16
| | 6.25 |
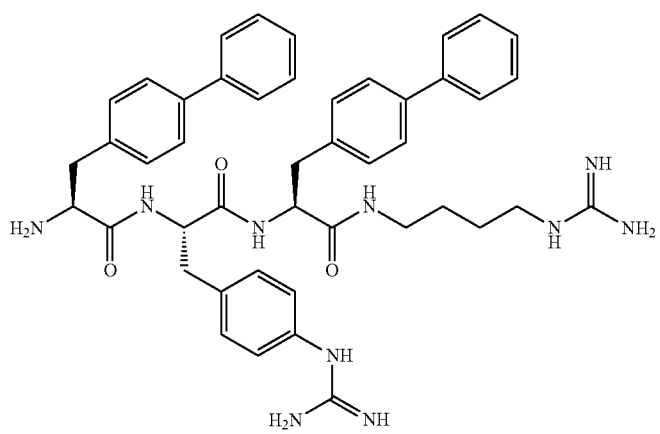
Compound 17

-continued
| Compound | MIC |
|---|---|
| 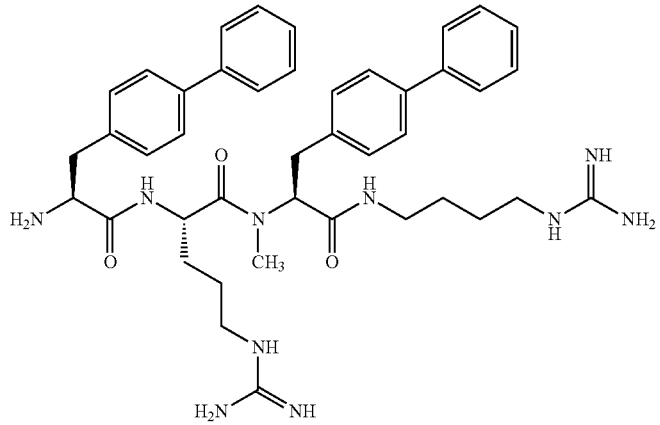<br>Compound 18 | 6.25 |
| 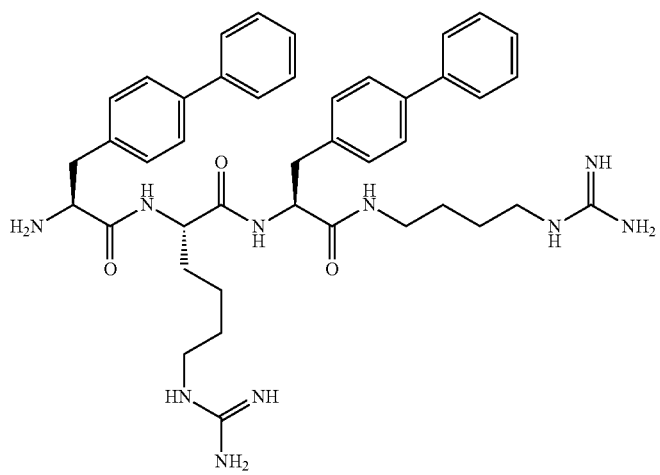<br>Compound 19 | 6.25 |
| 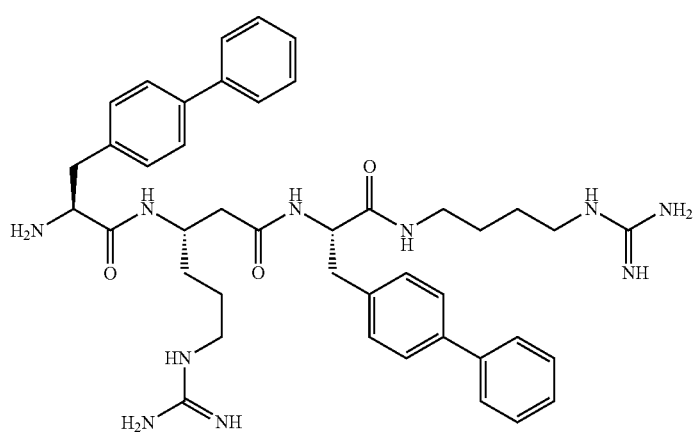<br>Compound 20 | 6.25 |

| Compound | MIC |
|---|---|
| 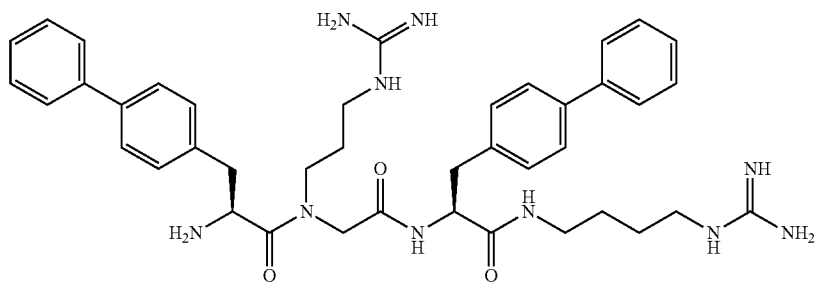
Compound 21 | 6.25 |
| 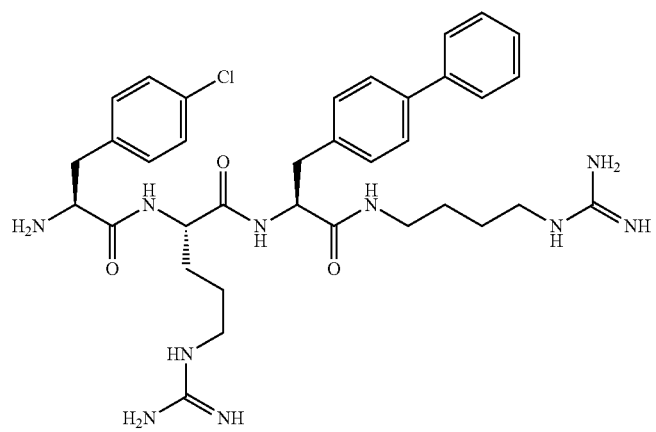
Compound 22 | 25 |
| 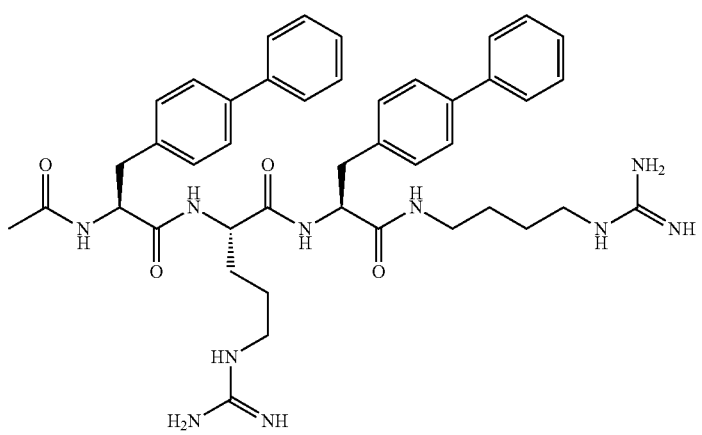
Compound 23 | 12.5 |

| Compound | MIC |
|---|---|
| | 12.5 |
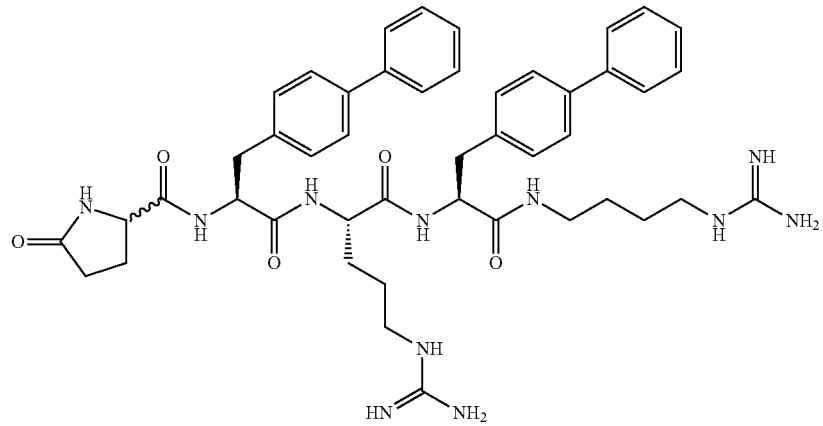
Compound 24
| | 12.5 |
|---|---|
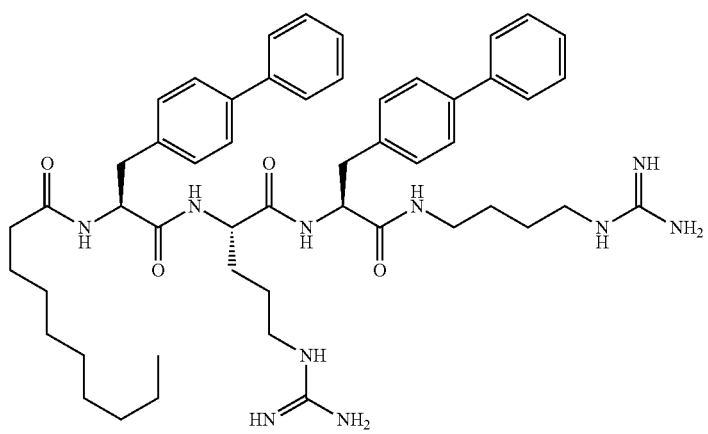
Compound 25
| | 12.5 |
|---|---|
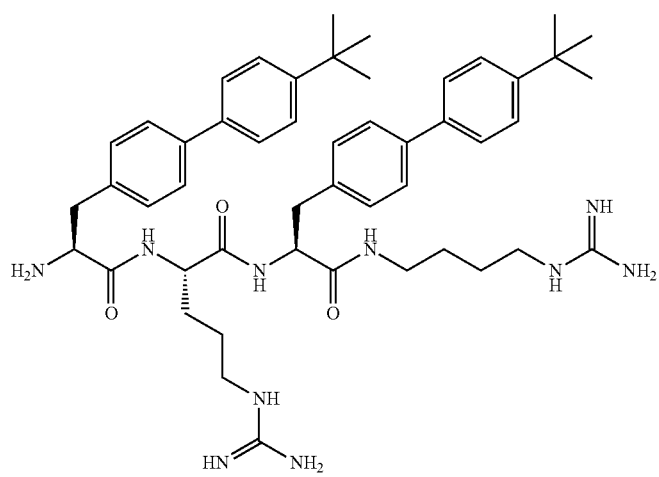
Compound 26

| Compound | MIC |
|---|---|
| Compound 27 | 6.25 |
| Compound 28 | 12.5 |
| Compound 29 | 3.125 |

The mass spectra of these compounds are shown in FIGS. 5a to 5h.

Figure 5:
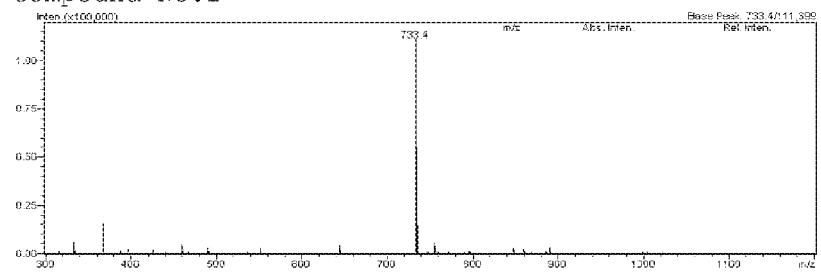
FIG. 5a shows the mass spectra of Compounds 1-4.
FIG. 5b shows the mass spectra of Compounds 5-8.
FIG. 5c shows the mass spectra of Compounds 9-12.
FIG. 5d shows the mass spectra of Compounds 13-16.
FIG. 5e shows the mass spectra of Compounds 17-19.
FIG. 5f shows the mass spectra of Compounds 20-23.
FIG. 5g shows the mass spectra of Compounds 24-27.
FIG. 5h shows the mass spectra of Compounds 28-29.
FIG. 5i shows the NMR spectra of compound (A).
Figure 5:
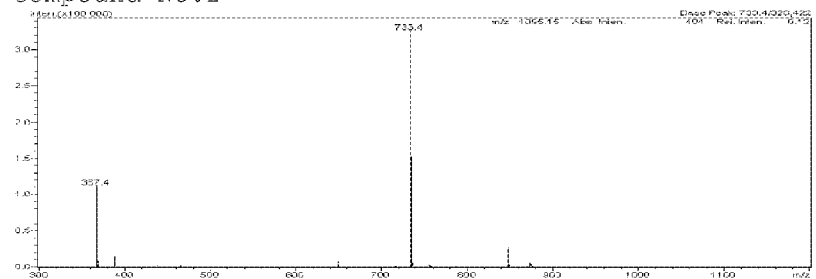
Figure 5:
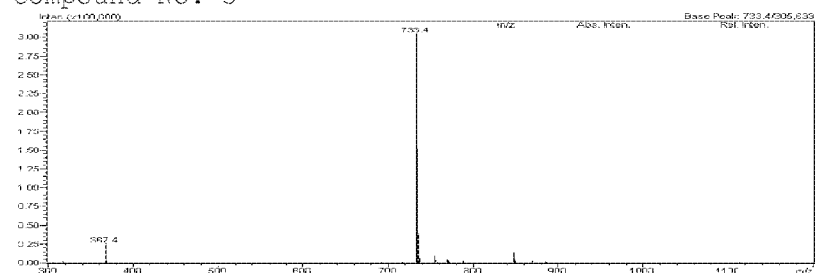
Figure 5:
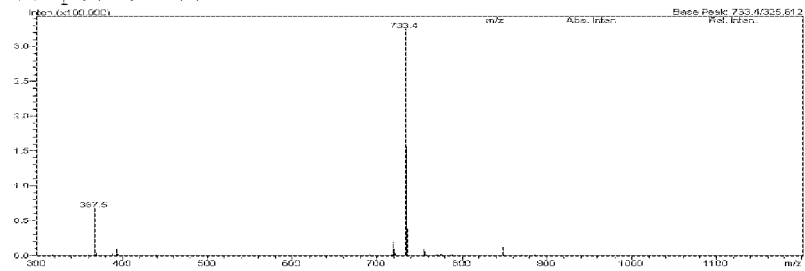
Figure 5B:
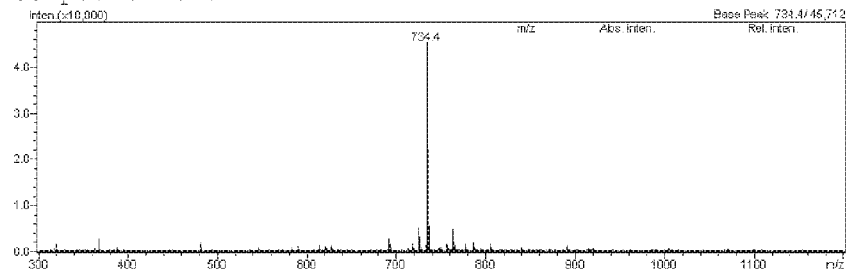
Figure 5B:
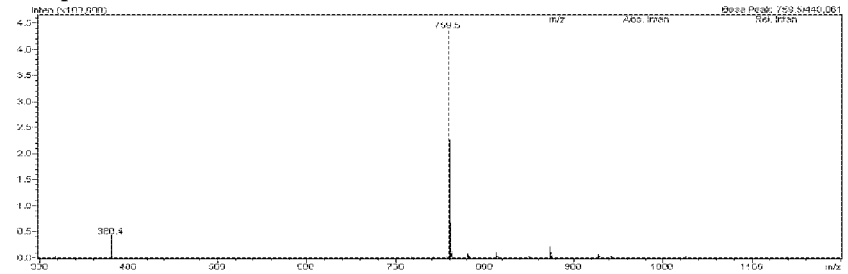
Figure 5B:
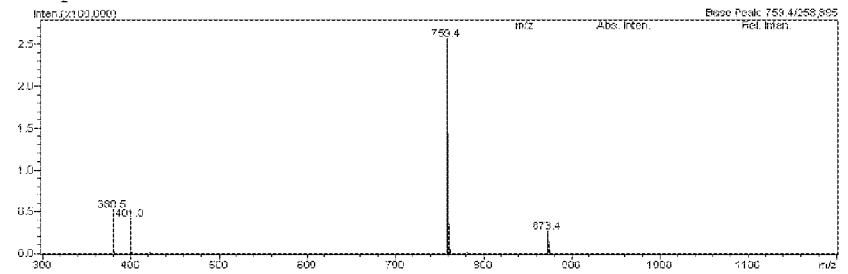
Figure 5B:
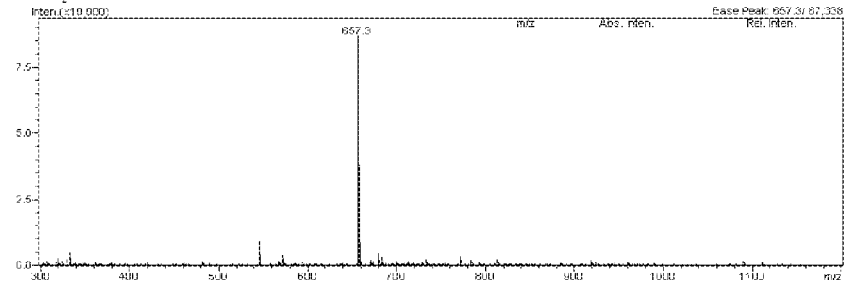
Figure 5C:
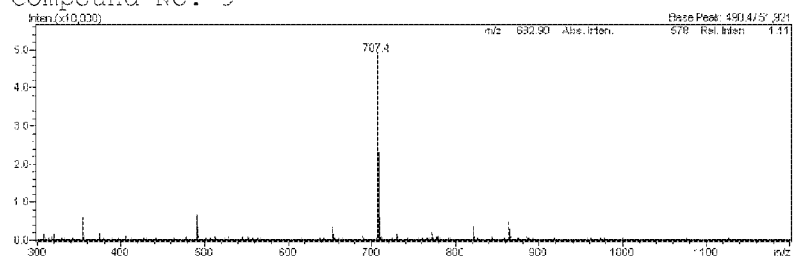
Figure 5C:
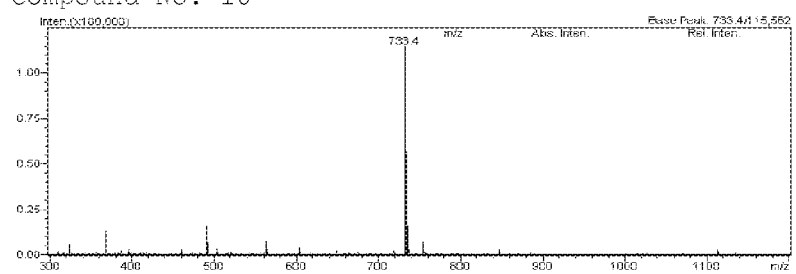
Figure 5C:
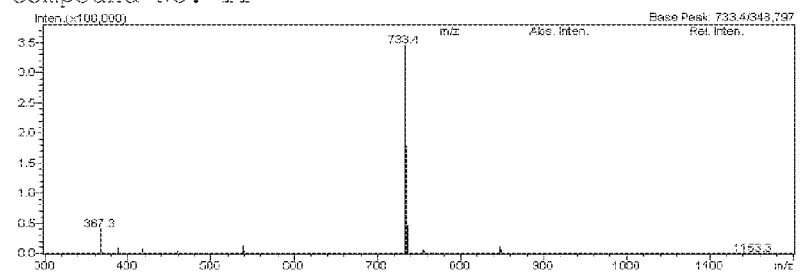
Figure 5C:
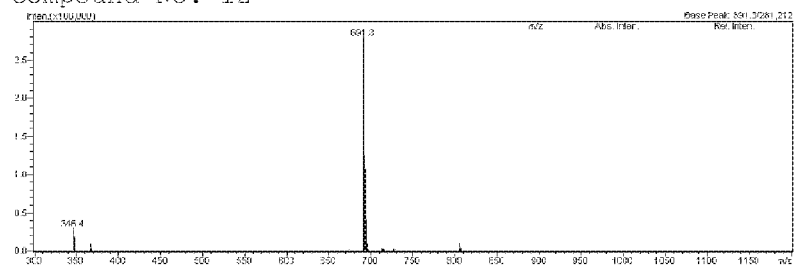
Figure 5D:
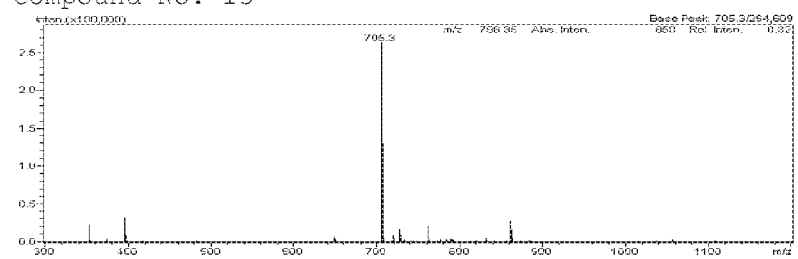
Figure 5D:
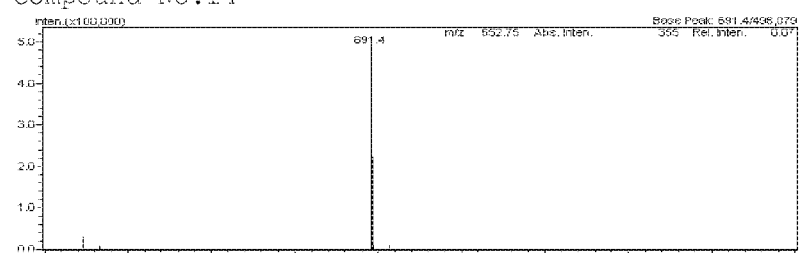
Figure 5D:
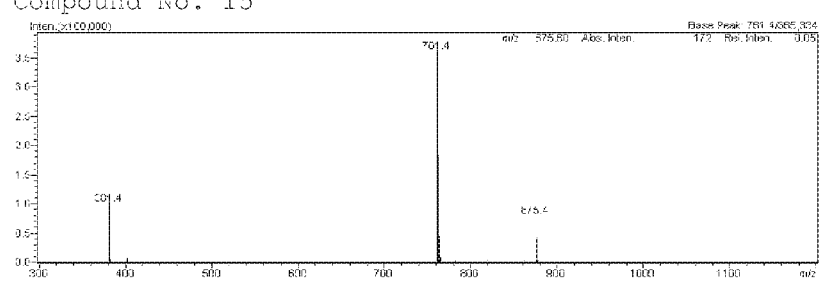
Figure 5D:
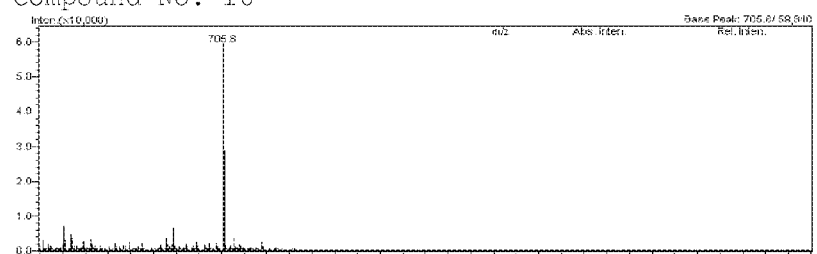
Figure 5E:
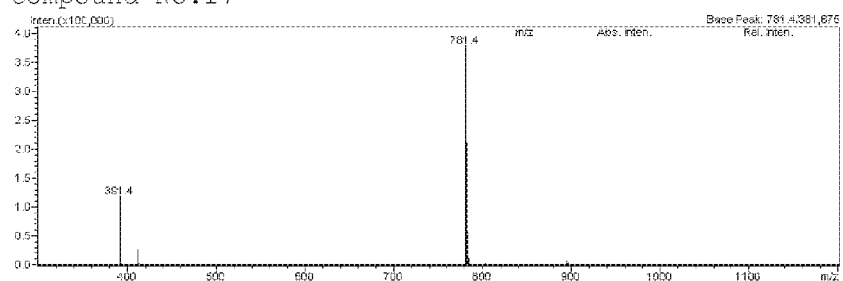
Figure 5E:
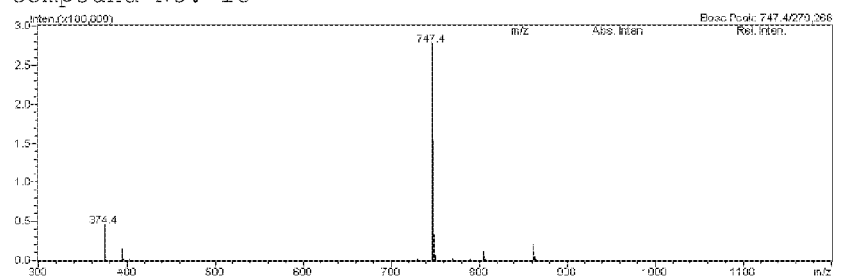
Figure 5E:
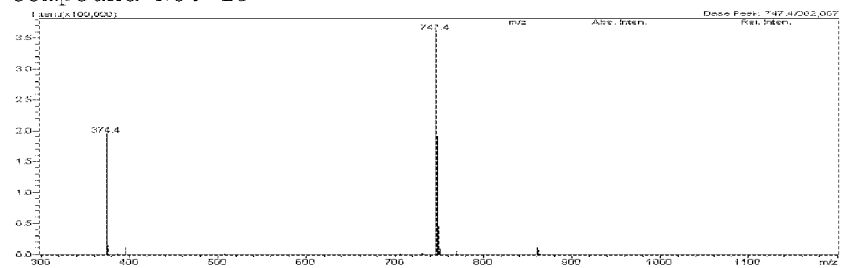
Figure 5F:
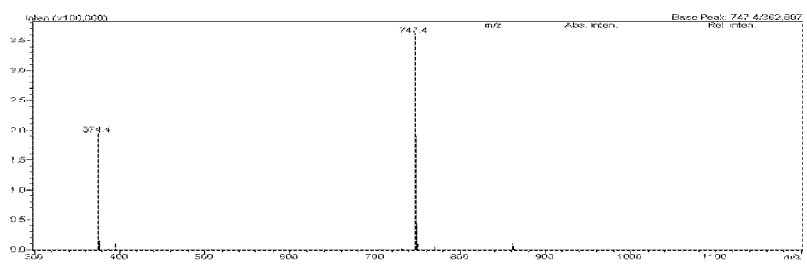
Figure 5F:
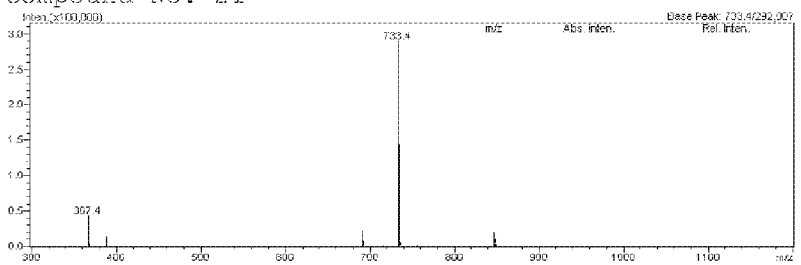
Figure 5F:
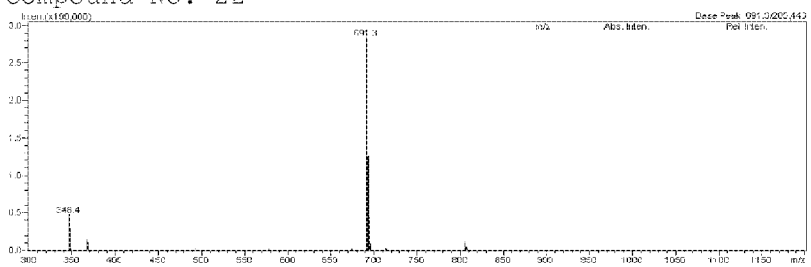
Figure 5F:
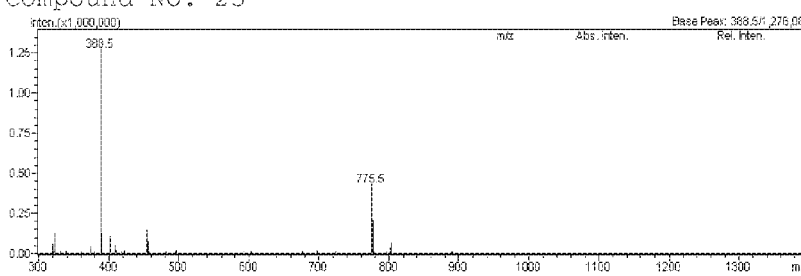
Figure 5G:
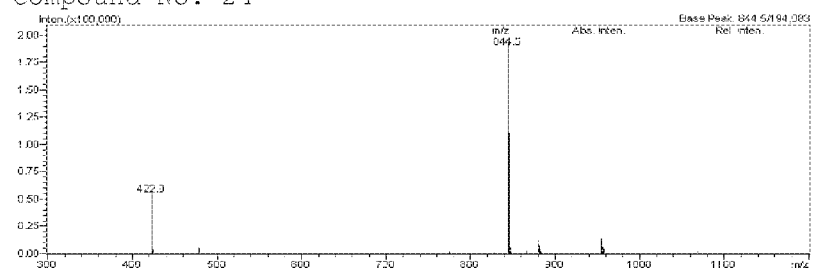
Figure 5G:
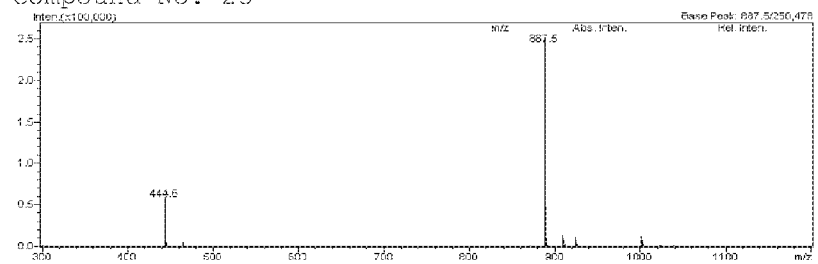
Figure 5G:
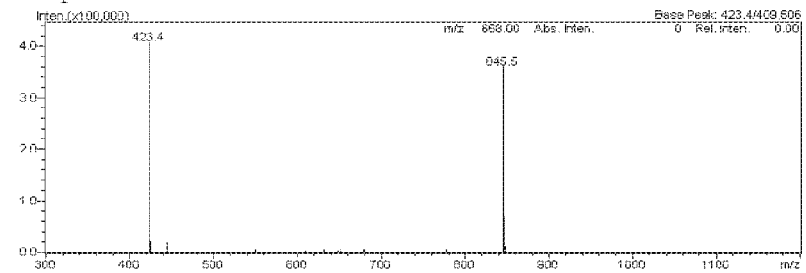
Figure 5G:
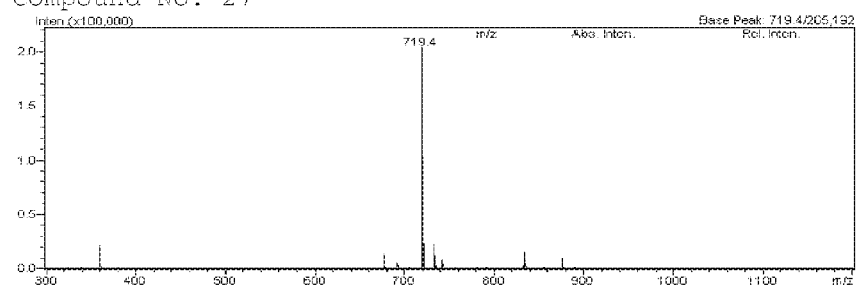
Figure 5H:
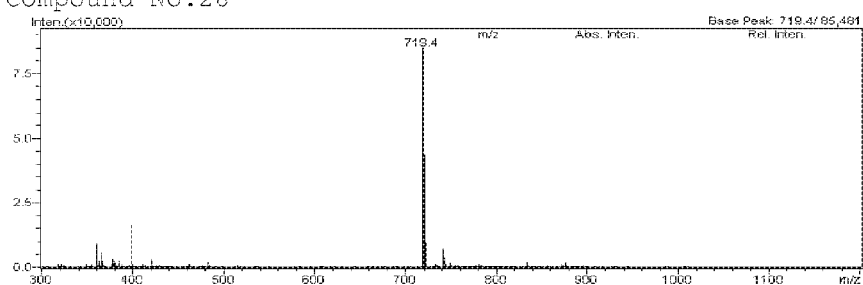
Figure 5H:
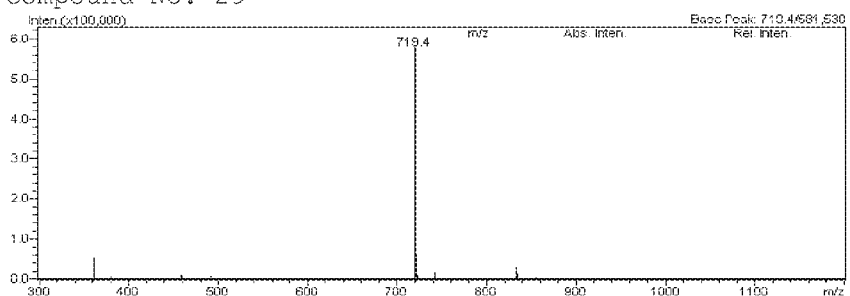
Figure 5I:
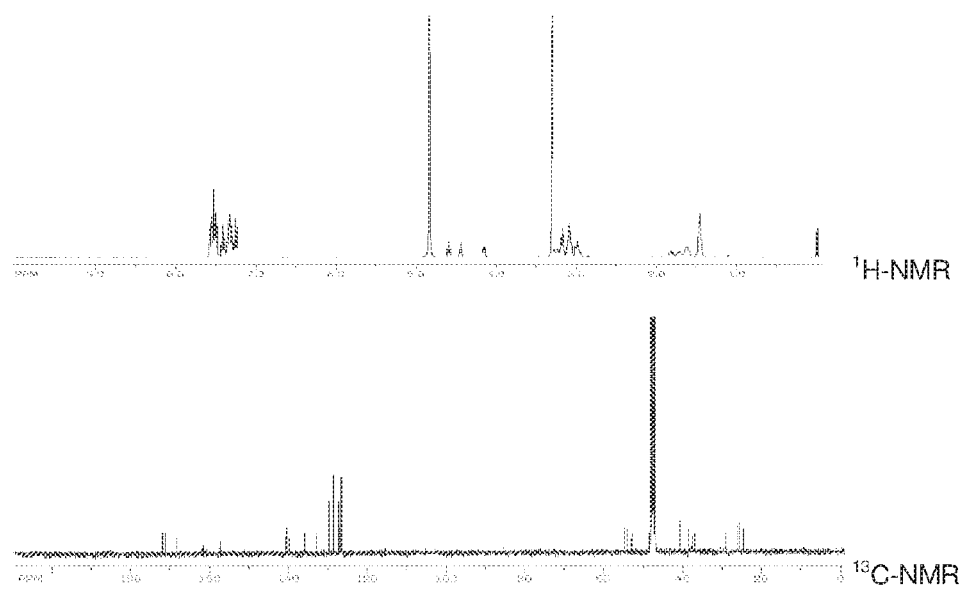

FIG. 5i shows the NMR spectra of compound (A).

The NMR data of the other compounds is as follows:

Compound 2: $^{1}$H NMR (400 MHz, CD$_3$OD) d 1.15-1.75 (8H, m), 2.85-3.30 (10H, m), 4.15 (1H, t), 4.30 (1H, t), 4.7 (1H, t), 7.25-7.60 (18H, m, aromatics).

Compound 3: $^{1}$H NMR (400 MHz, CD$_3$OD) d 0.95-1.5 (8H, m), 2.70-3.25 (10H, m), 4.10-4.20 (2H, m), 4.65 (1H, t), 7.25-7.65 (18H, m, aromatics).

Compound 4: $^{1}$H NMR (400 MHz, CD$_3$OD) d 0.95-1.6 (8H, m), 2.7-3.30 (10H, m), 4.10-4.20 (2H, m), 5.60-5.70 (1H, m), 7.25-7.70 (18H, m, aromatics).

Compound 5: insufficient compound for NMR

Compound 6: $^1$H NMR (400 MHz, CD$_3$OD) d 1.20-1.90 (13H, m), 2.90-3.25 (5H, m), 3.35-3.50 (1H, s), 4.75 (1H, s), 5.15 ((1H, t), 5.45 (1H, t), 5.65 (1H, t), 7.20-7.65 (18H, m, aromatics).

Compound 7: $^1$H NMR (400 MHz, CD$_3$OD) d 1.10-1.40 (5H, m), 1.55-2.05 (8H, m), 2.90-3.20 (6H, m), 3.55 (1H, m), 4.10 (1H, t), 4.40 (1H, t), 4.55 (1H, t), 7.20-7.60 (18H, m, aromatics).

Compound 8: $^1$H NMR (400 MHz, CD$_3$OD) d 1.41-1.71 (8H, m), 1.55-2.05 (8H, m), 2.96-3.25 (10H, m), 4.13 (1H, t), 4.41 (1H, t), 4.52 (1H, t), 7.18-7.59 (14H, m, aromatics).

Compound 9: insufficient compound for NMR

Compound 10: $^1$H NMR (400 MHz, CD$_3$OD) d 1.05-1.85 (9H, m), 2.8-3.4 (9H, m), 4.15 (1H, t), 4.4 (1H, m), 4.5 (1H, m), 7.15-7.70 (13H, m, aromatics).

Compound 11: $^1$H NMR (400 MHz, CD$_3$OD) d 1.40-2.05 (8H, m), 3.05-3.25 (8H, m), 3.70-3.95 (1H, dd), 4.20-4.60 (3H, m), 4.95 (1H, d), 5.05 (1H, t), 7.25-7.60 (18H, m, aromatics).

Compound 12: insufficient compound for NMR

Compound 13: $^1$H NMR (400 MHz, CD$_3$OD) d 1.29-1.86 (9H, m), 2.89-3.16 (10H, m), 4.10 (1H, t), 4.42 (1H, t), 4.59 (1H, t), 7.23-7.50 (18H, m, aromatics).

Compound 14: $^1$H NMR (400 MHz, CD$_3$OD) d 1.45-1.90 (8H, m), 2.65 (1H, s), 2.90-3.20 (9H, m), 4.10 (1H, t), 4.45 (1H, t), 4.60 (1H, t), 7.20-7.60 (18H, m, aromatics).

Compound 15: $^1$H NMR (400 MHz, CD$_3$OD) d 1.40-1.85 (8H, m), 2.80 (6H, s), 2.90-3.30 (10H, m), 4.20 (1H, t), 4.40 (1H, t), 4.60 (1H, t), 7.20-7.60 (18H, m, aromatics).

Compound 16: $^1$H NMR (400 MHz, CD$_3$OD) d 1.10 (1H, d), 1.40 (3H, m), 1.85 (2H, s), 2.90-3.60 (8H, m), 4.15 (1H, m), 4.55-4.70 (2H, m), 7.20-7.65 (18H, m, aromatics).

Compound 17: $^1$H NMR (400 MHz, CD$_3$OD) d 1.45 (4H, s), 2.8-3.2 (10H, m), 4.1 (1H, t), 4.50 (1H, t), 4.65 (1H, t), 7.15-7.60 (22H, m, aromatics).

Compound 18: insufficient compound for NMR

Compound 19: $^1$H NMR (400 MHz, CD$_3$OD) d 1.25-1.85 (11H, m), 2.90-3.25 (9H, m), 4.15 (1H, t), 4.40 (1H, t), 4.60 (1H, t), 7.20-7.60 (18H, m, aromatics).

Compound 20: $^1$H NMR (400 MHz, CD$_3$OD) d 1.35-1.54 (8H, m), 2.30-2.38 (2H, m), 2.85-3.19 (10H, m), 4.08 (1H, t), 4.16 (1H, t), 4.59 (1H, t), 7.30-7.62 (18H, m, aromatics).

Compound 21: $^1$H NMR (400 MHz, CD$_3$OD) d 1.40-1.70 (6H, m), 2.90-3.30 (11H, m), 3.80-4.00 (2H, q), 4.15 (1H, d), 4.40 (1H, t), 4.65 (1H, t), 7.25-7.65 (18H, m, aromatics).

Compound 22: $^1$H NMR (400 MHz, CD$_3$OD) d 1.09 (1H, m), 1.48-1.85 (8H, m), 2.86-3.19 (9H, m), 4.07 (1H, t), 4.40 (1H, t), 4.60 (1H, t), 7.09-7.57 (13H, m, aromatics).

Compound 23: $^1$H NMR (400 MHz, CD$_3$OD) d 1.52-1.80 (8H, m), 1.92 (3H, s), 2.65 (1H, s), 2.91-3.13 (9H, m), 4.32 (1H, t), 4.51-4.56 (2H, m), 7.25-7.58 (18H, m, aromatics).

Compound 24: $^1$H NMR (400 MHz, CD$_3$OD) d 1.47-2.00 (8H, m), 2.21-2.23 (2H, t), 2.35-2.45 (2H, m), 2.65 (1H, s), 2.92-3.16 (8H, m), 4.17 (1H, m), 4.35 (1H, m), 4.57 (2H, m), 7.25-7.59 (18H, m, aromatics).

Compound 25: $^1$H NMR (400 MHz, CD$_3$OD) d 0.85 (3H, t), 1.10-1.75 (23H, m), 2.14-2.17 (2H, m), 2.89-2.99 (9H, m), 4.20 (1H, t), 4.61 (2H, t), 7.28-7.59 (18H, m, aromatics).

Compound 26: $^1$H NMR (400 MHz, CD$_3$OD) d 1.09 (1H, d), 1.29-1.35 (16H, m), 1.47 (3H, s), 1.62-1.90 (4H, m), 2.65 (3H, s), 2.99-3.20 (10H, m), 4.12 (1H, s), 4.45 (1H, s), 4.61 (1H, s), 7.23-7.55 (16H, m, aromatics).

Compound 27: $^1$H NMR (400 MHz, CD$_3$OD) d 1.60-1.77 (8H, m), 3.62 (4H, s), 2.81-3.21 (11H, m), 7.32-7.64 (18H, m, aromatics).

Compound 28: $^1$H NMR (400 MHz, CD$_3$OD) d 1.30-1.52 (8H, m), 2.66 (1H, s), 2.93-3.00 (6H, m), 3.08-3.24 (5H, m), 4.13-4.20 (2H, m), 4.26 (1H, s), 7.33-7.67 (18H, m, aromatics).

Compound 29: $^1$H NMR (400 MHz, CD$_3$OD) d 1.44-1.62 (8H, m), 2.56-2.60 (2H, m), 2.84-3.16 (13H, m), 3.38-3.49 (2H, m), 4.70 (1H, m), 7.22-7.59 (18H, m, aromatics).

It will be apparent that this and various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method of treating a bacterial infection caused disease, disorder or condition in a subject in need of such treatment, comprising administering to said subject a compound of formula (I) or (Ic):

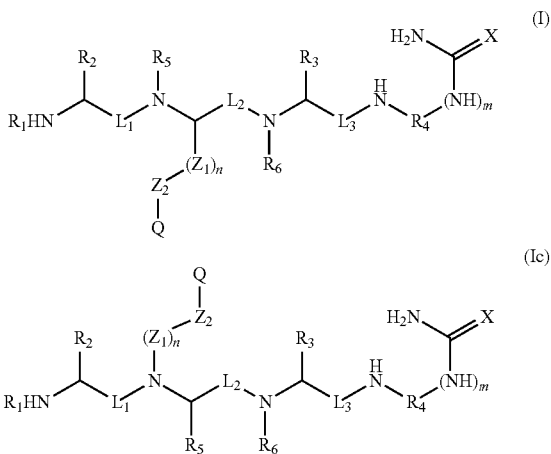

wherein $L_1$ represents —CO—, alkandiyl, -alkyl-CO— or —CO-alkyl-;

$L_2$ represents —CO—, alkandiyl, -alkyl-CO— or —CO-alkyl-;

$L_3$ represents —CO—, alkandiyl, -alkyl-CO— or —CO-alkyl-;

$R_1$ represents hydrogen, acyl, carbamoyl, alkylaminocarbonyl, dialkylaminocarbonyl, arylcarbonyl, cycloalkylcarbonyl or heterocyclylcarbonyl;

$R_2$ represents optionally substituted alkyl, aralkyl or heteroaralkyl;

$R_3$ represents hydrogen, or represents optionally substituted alkyl, aralkyl or heteroaralkyl;

$R_4$ represents optionally substituted alkandiyl, alkendiyl, alkyndiyl, cycloalkyldiyl, alkylcycloalkyldiyl, alkylcycloalkylalkyldiyl, aryldiyl, alkylaryldiyl or alkylarylalkyldiyl;

$R_5$ represents hydrogen, or represents optionally substituted alkyl, aralkyl or heteroaralkyl;

$R_6$ represents hydrogen, or represents optionally substituted alkyl, aralkyl or heteroaralkyl;

provided that at least two of the substituents $R_2$, $R_3$, $R_5$ and $R_6$ are optionally substituted aralkyl or heteroaralkyl;

wherein at least one of $R_2$ or $R_3$ is an optionally substituted biphenyl-$C_1$-$C_4$-alkyl;

n is 0, 1, 2, 3 or 4; and m is 0 or 1;
Q is —NH$_2$, —NH—C(NH)—NH$_2$ or —NH—C(N-alkyl)-NH-alkyl;
X is NH, O or S;
Z$_1$ is —CH$_2$—;
Z$_2$ is a direct bond, alkandiyl, cycloalkyldiyl or aryldiyl;
or pharmaceutically acceptable salts thereof.

2. The method of claim 1, wherein the bacterial infection is caused by bacteria that have gained a resistance against the penicillin-type antibiotics or vancomycin.

3. The method of claim 1, wherein the bacterial infection is caused by a Gram-positive bacteria.

4. The method of claim 1, wherein the bacterial infection is caused by a bacteria selected from *Staphylococcus aureus*, *Streptococcus pyogenes* and *Streptococcus pneumoniae*.

5. The method of claim 1, wherein the disease, disorder or condition is a skin infection, a respiratory disease, food poisoning or any other life-threatening systemic disease.

6. The method of claim 1, wherein the disease, disorder or condition is boils, sinusitis, pneumonia or food poisoning.

7. The method of claim 1, wherein the bacterial infection is treated by topical use of the compound of formula (I) or (Ic).

8. The method according to claim 1, wherein the compound is a compound of formula (I):

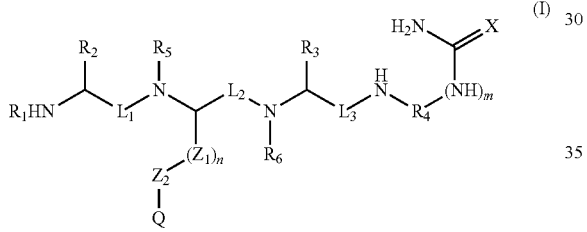

wherein
L$_1$ represents —CO—, alkandiyl, -alkyl-CO— or —CO-alkyl-;
L$_2$ represents —CO—, alkandiyl, -alkyl-CO— or —CO-alkyl-;
L$_3$ represents —CO—, alkandiyl, -alkyl-CO— or —CO-alkyl-;
R$_1$ represents hydrogen, acyl, carbamoyl, alkylaminocarbonyl, dialkylaminocarbonyl, arylcarbonyl, cycloalkylcarbonyl or heterocyclylcarbonyl;
R$_2$ represents optionally substituted alkyl, aralkyl or heteroaralkyl;
R$_3$ represents hydrogen, or represents optionally substituted alkyl, aralkyl or heteroaralkyl;
R$_4$ represents optionally substituted alkandiyl, alkendiyl, alkyndiyl, cycloalkyldiyl, alkylcycloalkyldiyl, alkylcycloalkylalkyldiyl, aryldiyl, alkylaryldiyl or alkylarylalkyldiyl;
R$_5$ represents hydrogen, or represents optionally substituted alkyl, aralkyl or heteroaralkyl;
R$_6$ represents hydrogen, or represents optionally substituted alkyl, aralkyl or heteroaralkyl;
provided that at least two of the substituents R$_2$, R$_3$, R$_5$ and R$_6$ are optionally substituted aralkyl or heteroaralkyl;
wherein at least one of R$_2$ or R$_3$ is an optionally substituted biphenyl-C$_1$-C$_4$-alkyl;
n is 0, 1, 2, 3 or 4; and m is 0 or 1;
Q is —NH$_2$, —NH—C(NH)—NH$_2$ or —NH—C(N-alkyl)-NH-alkyl;
X is NH, O or S;
Z$_1$ is —CH$_2$—;
Z$_2$ is a direct bond, alkandiyl, cycloalkyldiyl or aryldiyl;
or a pharmaceutically acceptable salt of such compound.

9. The method according to claim 1, wherein the compound is a compound of formula (I):

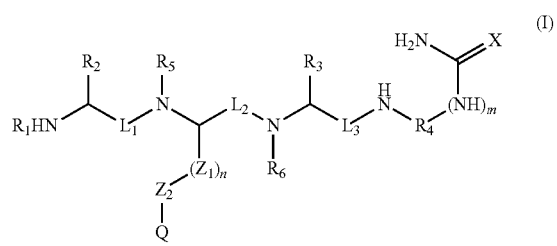

wherein
L$_1$ represents —CO—, C$_1$-C$_3$-alkandiyl, —C$_1$-C$_2$-alkyl-CO— or —CO—C$_1$-C$_2$-alkyl-;
L$_2$ represents —CO—, C$_1$-C$_3$-alkandiyl, —C$_1$-C$_2$-alkyl-CO— or —CO—C$_1$-C$_2$-alkyl-;
L$_3$ represents —CO—, C$_1$-C$_3$-alkandiyl, —C$_1$-C$_2$-alkyl-CO— or —CO—C$_1$-C$_2$-alkyl-;
R$^1$ represents hydrogen, C$_1$-C$_{20}$-alkyl-CO—, C$_2$-C$_{20}$-alkenyl-CO—, C$_1$-C$_{20}$-alkyl-NH—CO—, (C$_1$-C$_{20}$-alkyl)$_2$-N—CO—, arylcarbonyl having 6 or 10 carbon atoms in the aryl moiety, heterocyclylcarbonyl having 1 to 3 hetero atoms selected from N, O and S in a 3 to 6 membered ring, or C$_3$-C$_7$-cycloalkylcarbonyl;
R$^2$ represents optionally substituted C$_1$-C$_{12}$-alkyl, phenyl-C$_1$-C$_4$-alkyl, biphenyl-C$_1$-C$_4$-alkyl or naphthyl-C$_1$-C$_4$-alkyl;
R$^3$ represents hydrogen or represents optionally substituted C$_1$-C$_{12}$-alkyl, phenyl-C$_1$-C$_4$-alkyl, biphenyl-C$_1$-C$_4$-alkyl or naphthyl-C$_1$-C$_4$-alkyl;
R$^4$ represents optionally substituted C$_1$-C$_{12}$-alkandiyl, C$_2$-C$_{12}$-alkendiyl, C$_2$-C$_{12}$-alkyndiyl, C$_3$-C$_7$-cycloalkyldiyl, —C$_1$-C$_6$-alkyl-C$_3$-C$_7$-cycloalkyl-, —C$_1$-C$_6$-alkyl-C$_3$-C$_7$-cycloalkyl-C$_1$-C$_6$-alkyl-, —C$_1$-C$_6$-alkyl-phenyl- or —C$_1$-C$_6$-alkyl-naphthyl-;
R$^5$ represents hydrogen or represents optionally substituted C$_1$-C$_{12}$-alkyl, phenyl-C$_1$-C$_4$-alkyl, biphenyl-C$_1$-C$_4$-alkyl or naphthyl-C$_1$-C$_4$-alkyl;
R$^6$ represents hydrogen or represents optionally substituted C$_1$-C$_{12}$-alkyl, phenyl-C$_1$-C$_4$-alkyl, biphenyl-C$_1$-C$_4$-alkyl or naphthyl-C$_1$-C$_4$-alkyl;
wherein at least one of R$_2$ or R$_3$ is an optionally substituted biphenyl-C$_1$-C$_4$-alkyl;
n is 0, 1, 2 or 3;
m is 0 or 1;
Q is —NH$_2$, —NH—C(NH)—NH$_2$ or —NH—C(N—C$_1$-C$_2$-alkyl)-NH—C$_1$-C$_2$-alkyl;
X is NH or O;
Z$_1$ is —CH$_2$—;
Z$_2$ is a direct bond, C$_1$-C$_3$-alkandiyl, cyclohexyldiyl or phenyldiyl;
or a pharmaceutically acceptable salt of such compound.

10. The method according to claim 1, wherein the compound is a compound of formula (I):

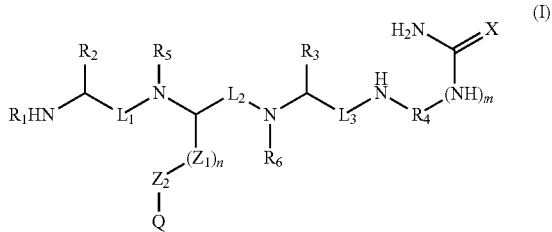

(I)

wherein
L₁ represents —CO—, —CH₂—, —CH₂—CH₂—, —CH₂—CO— or —CO—CH₂—;
L₂ represents —CO—, —CH₂—, —CH₂—CH₂—, —CH₂—CO— or —CO—CH₂—;
L₃ represents —CO—, —CH₂—, —CH₂—CH₂—, —CH₂—CO— or —CO—CH₂—;
R¹ represents hydrogen, C₁-C₁₆-alkyl-CO—, C₂-C₁₆-alkenyl-CO—, C₁-C₁₆-alkyl-NH—CO—, (C₁-C₁₆-alkyl)₂-N—CO—, heterocyclylcarbonyl having 1 to 2 hetero atoms selected from N, O and S in a 3 to 6 membered ring, or phenylcarbonyl;
R² represents optionally halogen substituted or optionally C₁-C₄-alkyl substituted C₁-C₁₂-alkyl, phenyl-C₁-C₂-alkyl, biphenyl-C₁-C₂-alkyl or naphthyl-C₁-C₂-alkyl;
R³ represents hydrogen or represents optionally halogen substituted or optionally C₁-C₄-alkyl substituted C₁-C₁₂-alkyl, phenyl-C₁-C₂-alkyl, biphenyl-C₁-C₂-alkyl or naphthyl-C₁-C₂-alkyl;
R⁴ represents C₂-C₆-alkandiyl, C₂-C₆-alkendiyl, C₂-C₆-alkyndiyl, C₃-C₇-cycloalkyldiyl, —C₁-C₆-alkyl-C₃-C₇-cycloalkyl-, —C₁-C₆-alkyl-C₃-C₇-cycloalkyl-C₁-C₆-alkyl-, —CH(COOH)—C₁-C₆-alkyl-, —CH(CONH₂)—C₃H₆— or —C₁-C₆-alkyl-phenyl-;
R⁵ represents hydrogen or represents optionally halogen substituted or optionally C₁-C₄-alkyl substituted C₁-C₁₂-alkyl, phenyl-C₁-C₂-alkyl, biphenyl-C₁-C₂-alkyl or naphthyl-C₁-C₂-alkyl;
R⁶ represents hydrogen or represents optionally halogen substituted or optionally C₁-C₄-alkyl substituted C₁-C₁₂-alkyl, phenyl-C₁-C₂-alkyl, biphenyl-C₁-C₂-alkyl or naphthyl-C₁-C₂-alkyl;
wherein at least one of R₂ or R₃ is an optionally halogen substituted or optionally C₁-C₄-alkyl substituted biphenyl-C₁-C₂-alkyl;
n is 0, 1, 2 or 3;
m is 0 or 1;
Q is —NH₂, —NH—C(NH)—NH₂ or —NH—C(N—CH₃)—NH—CH₃;
X is NH or O;
Z₁ is —CH₂—;
Z₂ is a direct bond, —CH₂—, cyclohexyldiyl or phenyldiyl;
or a pharmaceutically acceptable salt of such compound.

11. The method according to claim 1, wherein the compound is a compound of formula (I):

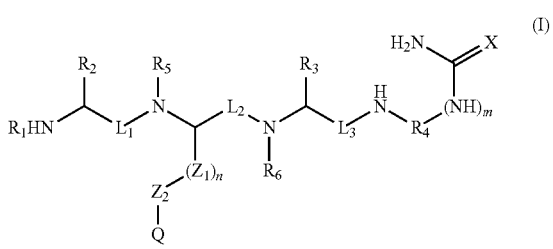

(I)

wherein
L₁ represents —CO— or —CH₂—;
L₂ represents —CO—, —CH₂— or —CH₂—CO—;
L₃ represents —CO— or —CH₂—;
R¹ represents hydrogen, methylcarbonyl, ethylcarbonyl, nonylcarbonyl or heterocyclylcarbonyl having 1 to 2 hetero atoms selected from N and O in a 3 to 6 membered ring;
R² represents optionally halogen substituted or optionally C₁-C₄-alkyl substituted benzyl, biphenylmethyl or naphthylmethyl;
R³ represents hydrogen or represents optionally halogen substituted or optionally C₁-C₄-alkyl substituted benzyl, biphenylmethyl or naphthylylmethyl;
R⁴ represents propandiyl, butandiyl, pentandiyl, butendiyl, butyndiyl, cyclohexyldiyl, —CH(COOH)—C₃H₆—, —CH(CONH₂)—C₃H₆— or —CH₂-phenyl;
R⁵ represents hydrogen or represents optionally halogen substituted or optionally C₁-C₄-alkyl substituted benzyl, biphenylmethyl or naphthylmethyl;
R⁶ represents hydrogen or represents optionally halogen substituted or optionally C₁-C₄-alkyl substituted methyl, benzyl, biphenylmethyl or naphthylmethyl;
wherein at least one of R₂ or R₃ is an optionally halogen substituted or optionally C₁-C₄-alkyl substituted biphenylmethyl;
n is 0, 1, 2 or 3;
m is 0 or 1;
Q is —NH₂, —NH—C(NH)—NH₂ or —NH—C(N—CH₃)—NH—CH₃;
X is NH or O;
Z₁ is —CH₂—;
Z₂ is a direct bond, —CH₂— or phenyldiyl;
or a pharmaceutically acceptable salt of such compound.

* * * * *